United States Patent
Li et al.

(10) Patent No.: US 7,256,187 B2
(45) Date of Patent: Aug. 14, 2007

(54) RIFAMYCIN C-11 OXIME DERIVATIVES EFFECTIVE AGAINST DRUG-RESISTANT MICROBES

(75) Inventors: Jing Li, Dallas, TX (US); Charles Z. Ding, Plano, TX (US); Zhenkun Ma, Dallas, TX (US)

(73) Assignee: Cumbre Pharmaceuticals Inc., Dallas, TX (US)

( * ) Notice: Subject to any disclaimer, the term of this patent is extended or adjusted under 35 U.S.C. 154(b) by 125 days.

(21) Appl. No.: 11/076,172

(22) Filed: Mar. 9, 2005

(65) Prior Publication Data

US 2005/0203076 A1    Sep. 15, 2005

Related U.S. Application Data

(60) Provisional application No. 60/551,684, filed on Mar. 10, 2004.

(51) Int. Cl.
  *C07D 498/18*  (2006.01)
  *C07D 513/18*  (2006.01)
  *A61K 31/535* (2006.01)
  *A61K 31/395* (2006.01)
  *A61P 31/04*  (2006.01)

(52) U.S. Cl. .............................. 514/232.8; 514/253.01; 514/253.05; 514/253.08; 514/254.02; 514/254.11; 514/300; 514/321; 514/339; 540/456

(58) Field of Classification Search ................ 540/456; 514/232.8, 468, 254.11, 339, 253.08, 300, 514/254.02, 253.01, 253.05, 321
See application file for complete search history.

(56) References Cited

U.S. PATENT DOCUMENTS 4,002,754 A    1/1977    Cricchio et al.
4,164,499 A    8/1979    Rossetti et al.
4,341,785 A    7/1982    Marchi et al.

FOREIGN PATENT DOCUMENTS

EP    0190709 B1    12/1989
EP    0228606 B1    2/1991
WO    WO94/28002 A1    12/1994
WO    WO93/051299 A2    6/2003

OTHER PUBLICATIONS

Bartolucci, C., et al.,Synthesis, Reactivity Studies, and X-Ray Crystal Structure of (11R)-25-O-Deacetyl-11-deoxo-11-hydroxy-21 ,23-O-isopropylidenerifamycin S; Helvetica Chimica Acta, 1990, vol. 73, pp. 185-190.
Brufani, M., et al., Rifamycins: an Insight into Biological Activity Based on Structural Investigations, 1974, vol. 87, pp. 409-435.
Bundgaard, H., et al., (c) Means to Enhance Penetration (1) Prodrugs as a Means to improve the delivery of peptide drugs, Advanced Drug Delivery Reviews, 8 (1992) pp. 1-38.
Farr, B. M., Rifamycins, in Principles and Practices of Infectious Diseases; Mandell, Douglas, and Bennett's Principles and Practices of Infectious Diseases, Churchill Livingstone, Philadelphia, pp. 348-361, (2000).
Kakeya, N., et al., Studies on Prodrugs of Cephalosporins. I. Synthesis and Biological Properties of Glycyloxybenzoyloxymethyl and Glycylaminobenzoyloxymethyl Esters of 7b-[2-(2-Aminothiazol-4-yl)-(Z)-2-methoxyiminoacetamido]-3-methyl-3-cephem-4-carboxylic Acid, Chem Phar Bull, 1984, vol. 32, pp. 692-698.
Neilsen, N.M, et al.; Glycolamide Esters as Biolabile Prodrugs of Carboxylic Acid Agents: Synthesis, Stability, Bioconversion, and Physiochemcial Properties; Journal of Pharmaceutical Sciences; Apr. 1988; vol. 77, pp. 285-298.
Bundgaard, H.; Design and Application of Prodrugs; A Textbook of Drug Design and Development; Krosgaard-Larsen and Bundgaard, H., eds.; 1991, Chapter 5, pp. 113-191.

*Primary Examiner*—Bruck Kifle
(74) *Attorney, Agent, or Firm*—Jackson Walker L.L.P.

(57) ABSTRACT

The invention relates to rifamycin derivatives having antimicrobial activities, including activities against drug-resistant microorganisms, specifically, the rifamycin derivatives having an oxime group at the C-11 position.

45 Claims, 8 Drawing Sheets

Scheme 1

(a) NH$_2$OH·HCl, pyridine, MeOH; (b) SnCl$_2$, NH$_4$OAc, 6N HCl, THF/MeOH/H$_2$O; (c) SnCl$_2$, NH$_4$OAc, 6N HCl, THF/MeOH/H$_2$O.

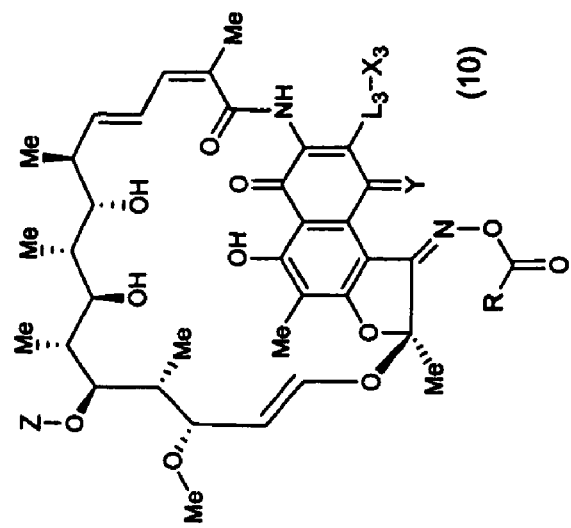
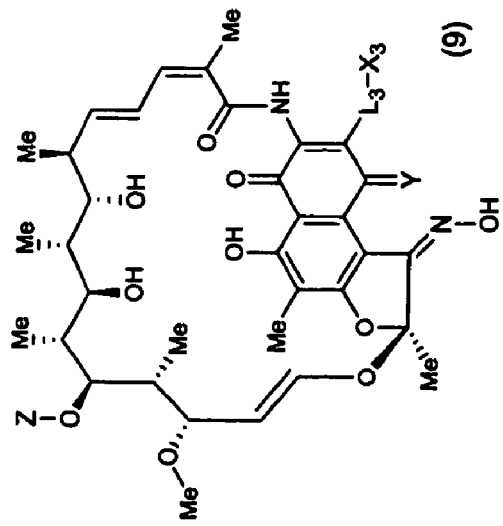
Scheme 4
(f) (RCO)₂O or RCOCl, Et₃N, CH₂Cl₂
Figure 5

RIFAMYCIN C-11 OXIME DERIVATIVES EFFECTIVE AGAINST DRUG-RESISTANT MICROBES

BACKGROUND

This application claims priority to U.S. Provisional Patent Application, Ser. No. 60/551,684, entitled "RIFAMYCIN C-11 OXIME DERIVATIVES EFFECTIVE AGAINST DRUG-RESISTANT MICROBES" filed on March 10, 2004, having Jing Li, Charles Z. Ding, and Zhenkun Ma listed as the inventors, the entire content of which is hereby incorporated by reference.

This invention relates to rifamycin C-11 oxime derivatives having antimicrobial activity, their compositions, and methods for treatment and prevention of microbial infections. More particularly, the current invention comprises rifamycin derivatives, in which the natural rifamycin C-11 keto group is converted to the C-11 oxime group. The compounds of the current invention demonstrate improved antimicrobial and antibacterial activity against resistant pathogens.

Rifamycins are natural products with potent antimicrobial activity. Examples of the naturally-occurring rifamycins are rifamycin B, rifamycin O, rifamycin R, rifamycin U, rifamycin S, rifamycin SV and rifamycin Y (Brufani et al., 1974). The therapeutic applications of the naturally-occurring rifamycins are limited due to their poor oral bioavailability, weak activity against Gram-negative pathogens and low distribution into the infected tissues. Progress has been made toward identifying semi-synthetic rifamycin derivatives to address the deficiencies. Many semi-synthetic rifamycin derivatives with improved spectrums and pharmacological profiles have been identified. Among the semi-synthetic compounds, rifampin, rifabutin and rifapetine have been developed into therapeutic agents and are widely used for the treatment of tuberculosis and other microbial infections (Farr, Rifamycins).

At present, one of the major problems associated with the rifamycin class of antimicrobial agents is the rapid development of microbial resistance. Mutations in the RpoB gene of RNA polymerase are mainly responsible for the high frequency of microbial resistance to rifamycins. Consequently, rifamycins are currently used only in combination therapies to minimize the development of resistance to this class of drug. Compounds of the current invention possess an oxyiminogroup (O—N=C) at the C-11 position of rifamycin in contrast to a keto (O=C) group at C-11 of the natural form of rifamycin. The inventive compounds exhibit potent activities against microbes including some rifampin resistant organisms.

References are made to rifamycin derivatives with chemical modifications on the C3 and/or C4 position of the naphthalene ring core, especially the therapeutic agents such as rifampin (U.S. Pat. No. 4,002,754), rifalazil (European Patent No. 0190709B1 and International Patent Application No. WO 03/051299 A2), rifabutin (U.S. Pat. No. 4,164,499), rifamycin P (European Patent No. 0228606 B1), rifaximin (U.S. Pat. No. 4,341,785). Modifications of the ansa chain frequently resulted in rifamycins with reduced antibacterial activity. Modifications on the C-36 position have also been reported (International Patent Application No. WO 94/28002).

Reference is also made to the simple reduction of the C-11 ketone to its alcohol (Bartolucci et al., 1990). There have been no other reported chemical modifications on the C-11 position of rifamycin. Compounds of the current invention are 11-deoxy-11-iminorifamycin derivatives, where the C-11 carbonyl oxygen was replaced by a nitrogen atom. Because of the trivalent nature of the nitrogen atom, extensive modifications on the C-11 position are now possible. The current invention constitutes novel compounds having C-11 modifications through preparation of imino derivatives at the C-11 position.

SUMMARY

One aspect of the current invention is a compound having Formula I, in quinone form, or Formula II, in hydroquinone form:

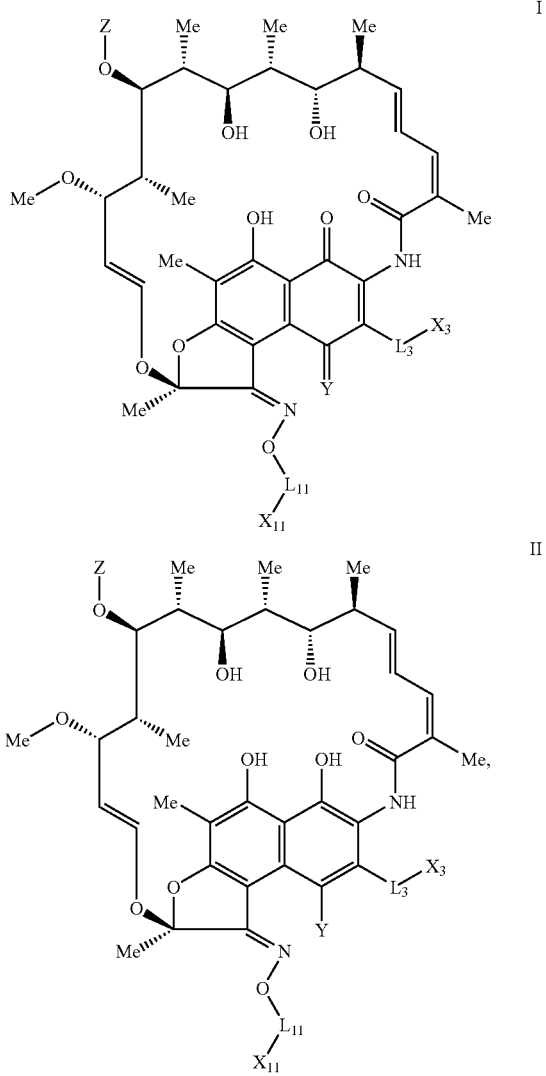

or salts, hydrates, prodrugs, and mixtures thereof.

A preferred $L_3$ and $L_{11}$, in the above structures independently represent a linker group comprising any combination of 0 to 5 groups which may be the same or different and are selected from —$CR_1R_2$—, —$NR_3$—, —O—, —C(=O)—, —S(=O)$_{0-2}$—, —C=N—, alkylene, alkenylene, alkynylene, and a bivalent ring containing 0 to 3 heteroatoms.

A preferred $X_3$ in the above structures represents —H, —OH, —$NH_2$, —$CO_2H$, halo, haloalkyl, —CN, alkyl, substituted alkyl, aryl, cycloalkyl, heteroaryl, heterocyclo, or -$Q_3$, wherein $Q_3$ is a structure associated with a therapeutic agent. Examples of therapeutic agents include macrolides, quinolones, beta-lactams, oxazolidinones, tetracyclines, and aminoglycosides.

A preferred $X_{11}$ in the above structures represents —H, —OH, —$NH_2$, —$CO_2H$, halo, haloalkyl, —CN, alkyl, substituted alkyl, aryl, cycloalkyl, heteroaryl, heterocyclo, or -$Q_{11}$, wherein $Q_{11}$ is a structure associated with a therapeutic agent. Examples of therapeutic agents include macrolides, quinolones, beta-lactams, oxazolidinones, tetracyclines, and aminoglycosides.

In Formula I above, a preferred Y comprises =O or =$NR_4$. In Formula II above, a preferred Y comprises —OH, —$NHR_4$, —$OR_5$, —$OCH_2CO_2H$, or —$OCH_2CONR_6R_7$.

A preferred Z in the above structures comprises —H or —$COCH_2R_8$, wherein $R_8$ represents —H, —OH, halo, —CN, —$CO_2H$, —$CONR_9R_{10}$, —$NR_{11}R_{12}$, —$OR_{13}$, —$S(=O)_{0-2}R_{14}$, or —$L_{25}Q_{25}$, wherein $L_{25}$ is absent or represents a heterocyclo group, and wherein $Q_{25}$ is a structure associated with a therapeutic agent. Examples of therapeutic agents include macrolides, quinolones, beta-lactams, oxazolidinones, tetracyclines, and animoglycosides.

In the above structures, $R_1$, $R_2$, $R_3$, $R_4$, $R_5$, $R_6$, $R_7$, $R_9$, $R_{10}$, $R_{11}$, $R_{12}$, $R_{13}$, and $R_{14}$ independently are the same or different and are H, alkyl, substituted alkyl, cycloalkyl, aryl, heteroaryl, or a heterocyclo group. In addition, $R_1$ may also be —OH, —SH, alkoxy, alkylthio, alkylamino, or dialkylamino. When appropriate, one or more of the following pairs: (i) $R_1$ and $R_2$, (ii) $R_6$ and $R_7$, (iii) $R_9$ and $R_{10}$, and (iv) $R_{11}$ and $R_{12}$ may join together with their respectively attached atoms to form a ring.

$Q_3$, $Q_{11}$, and $Q_{25}$ may be the same or different and may be any of the preferred structures shown in Formula III to IX:

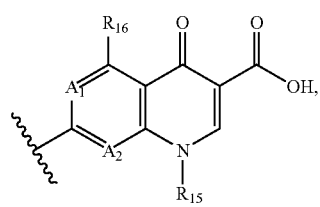

VII

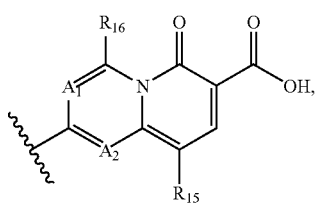

VIII

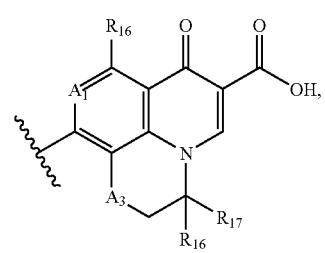

IX

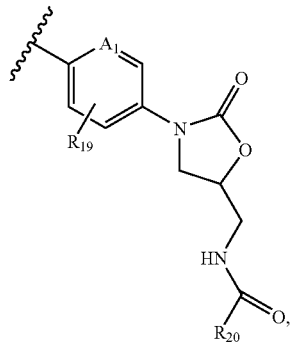

X

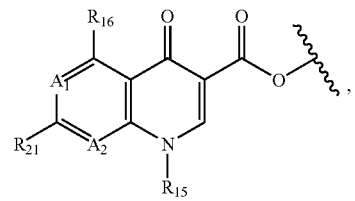

XI

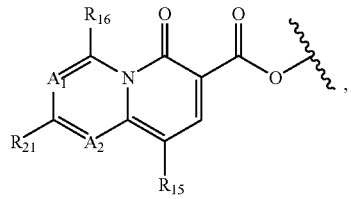

XII

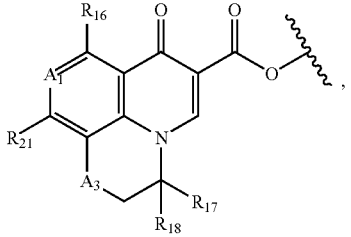

XIII wherein, $A_1$ is CH, CF, or N; $A_2$ is CH, CF, N, C—$CH_3$, C—$OCH_3$, C—$OCH_2F$, C—$OCHF_2$, or C—Cl; $A_3$ is —$CH_2$—, —O—, —S—, or —$NR_{22}$—; and $R_{15}$, $R_{17}$, $R_{18}$, $R_{20}$ and $R_{22}$ independently are the same or different and are H, alkyl, substituted alkyl, cycloalkyl, aryl, heteroaryl, or a heterocyclo group. In addition, $R_{17}$ and $R_{18}$, together with the carbon to which they are attached, may form a 3-6 membered cycloalkyl ring. $R_{16}$ is —H, —$NH_2$, —$NO_2$, —F, or a $C_{1-6}$ alkyl; $R_{19}$ is —H, halo, or an alkyl group; and $R_{21}$, is a heterocyclo group.

Even more preferably, therapeutic agent $Q_3$, $Q_{11}$, and $Q_{25}$ independently may be the same or different and may be any of the structures shown in FIG. 1.

Another aspect of the current invention comprises a method of treating microbial infection in a subject, wherein the subject is any species of the animal kingdom. The microbial infection can be caused by a bacterium or microorganism. The term "subject" refers more specifically to human and animals, wherein the animals can be used for: pets (e.g. cats, dogs, etc.); work (e.g. horses, cows, etc.); food (e.g. chicken, fish, lambs, pigs, etc); and all others known in the art. The method comprises administering an effective amount of one or more compounds of the present invention to the subject suffering from a microbial infection. The compounds of the present invention are effective against drug-resistant microbes and, in particular, rifamycin-resistant microbes.

BRIEF DESCRIPTION OF THE DRAWINGS

FIG. 5 shows a general synthetic procedure entitled Scheme 4;

DETAILED DESCRIPTION

Figure 1:
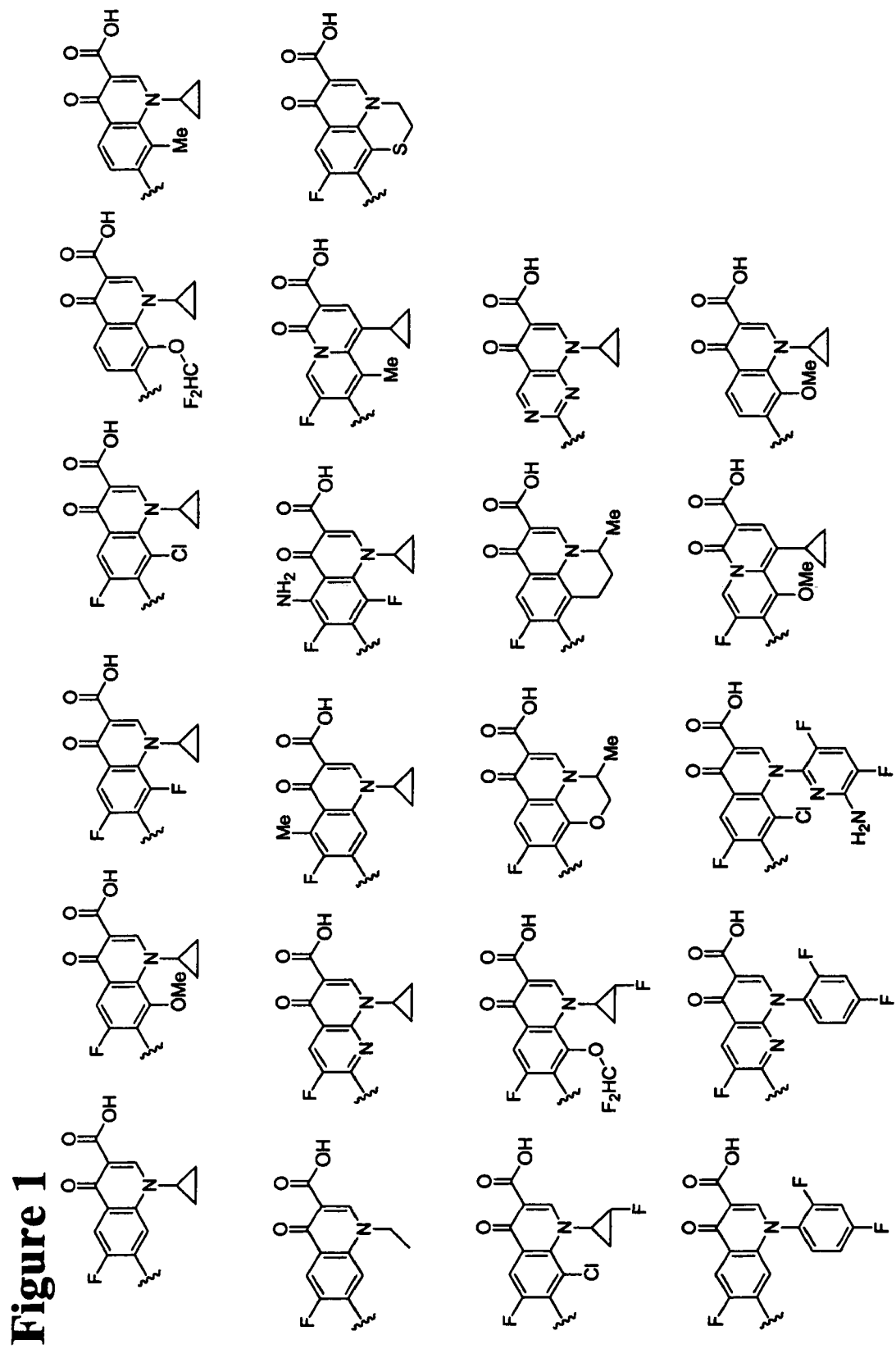
FIG. 1 shows a group of structures associated with quinolone class antibacterial agents.

Terms:

The following are definitions of terms used in this specification. The initial definition provided for a group or term herein applies to that group or term throughout the present specification, individually or as part of another group, unless otherwise indicated.

The term "acyl" as used herein, refers to a carbonyl (C=O) linked to an organic group, i.e., $R_d$—C=O, wherein $R_d$ may be selected from H, alkyl, alkenyl, substituted alkyl, substituted alkenyl, aryl, heterocyclo, cycloalkyl, or heteroaryl, as defined herein.

The term "alkenyl," as used herein, refers to a monovalent straight or branched chain group having 2 to 12 carbon atoms and containing at least one carbon-carbon double bond. Alkenyl groups of 2 to 6 carbon atoms and having one double bond are most preferred. The alkenyl groups of this invention can be optionally substituted.

The term "alkenylene," as used herein, refers to a bivalent straight or branched chain group containing at least one carbon-carbon double bond. The alkenylene groups of this invention can be optionally substituted.

The term "alkyl," as used herein, refers to a monovalent, saturated, straight or branched chain hydrocarbon group having 1 to 12 carbon atoms, preferably 1 to 8 carbons. Examples of alkyl group include methyl, ethyl, propyl, iso-propyl, n-butyl, iso-butyl, tert-butyl, neo-pentyl, and n-hexyl. Lower alkyl groups, that is, alkyl groups of 1 to 4 carbons, are most preferred. The alkyl groups of this invention can be optionally substituted. The term "alkyl" when used in conjunction with another group, such as in arylalkyl, refers to a substituted alkyl in which at least one of the substituents is the specifically-named group. For example, the term arylalkyl includes benzyl, phenethyl, or any other straight or branched chain alkyl having at least one aryl group attached at any point of the alkyl chain. As a further example, the term carbamylalkyl includes the group —(CH$_2$)$_n$—NH—C(=O)alkyl, wherein n is 1 to 12.

The term "alkylene," as used herein, refers to bivalent saturated, straight or branched chain hydrocarbon groups having 1 to 12 carbon atoms with substituents, preferably 1 to 8 carbon atoms, e.g., {—CH$_2$—}$_n$, wherein n is 1 to 12, preferably 1-8. Lower alkylene groups, that is, alkylene groups of 1 to 4 carbon atoms, are most preferred. The terms "alkenylene", "alkynylene", "arylene" and "heteroarylene" refer to bivalent radicals of alkenyl, alkynyl, aryl and heteroaryl groups, respectively, as defined in this specification. Examples of alkylene groups include methylene, ethylene, propylene, iso-propylene, n-butylene, isobutylene, and n-hexylene. When reference is made to a substituted alkylene, alkenylene, alkynylene, arylene, or heteroarylene group, these groups are substituted with one to four substitutents as defined above for alkyl groups.

The term "alkylamino," as used herein, refers to an amino group (—NH$_2$), wherein one hydrogen atom is replaced by an alkyl group. Examples of alkylamino include methylamino, ethylamino, propylamino, and isopropylamino.

The term "alkylthio," as used herein, refers to an alkyl or alkenyl or substituted alkyl or alkenyl group bonded through a nitrogen (—NR'—) group. For example, the term "aminoalkyl" includes the groups —NR'—C$_{1-12}$alkyl and —NR'—CH$_2$-aryl. (where R' is hydrogen, alkyl or substituted alkyl as defined above.) "Amino" refers to the group —NH$_2$.

The term "alkoxy," as used herein, refers to an alkyl, alkenyl, or substituted alkyl or alkenyl group bonded through an oxygen atom (—O—). For example, the term "alkoxy" includes the groups —O—C$_{1-12}$alkyl, —O—C$_{2-8}$alkenyl, —O—CH$_2$aryl, and so forth.

The term "alkoxycarbonyl" refers to a group having a carboxy or ester group (—CO$_2$) linked to an organic radical, i.e., (—CO$_2$-R$_d$), wherein R$_d$ is as defined above for acyl.

The term "alkynyl," as used herein, refers to a monovalent straight or branched chain group of 2 to 12 carbon atoms containing at least one carbon-carbon triple bond. Examples of alkynyl include ethynyl, propynyl, and butynyl. Alkynyl groups of 2 to 6 carbon atoms and having one triple bond are most preferred. The alkynyl groups of this invention can be optionally substituted.

The term "alkynylene," as used herein, refers to a bivalent straight or branched chain group of two to six carbon atoms containing at least one carbon-carbon triple bond. Examples of alkynylene include ethynylene, propynylene, and butynylene. The alkynylene groups of this invention can be optionally substituted.

The term "aprotic solvent," as used herein, refers to a solvent that is relatively inert to protonic activity, i.e., not acting as a proton donor. Examples include hexane, toluene, dichloromethane, ethylene dichloride, chloroform, tetrahydrofuran, N-methylpyrrolidinone, and diethyl ether.

The term "aryl" as used herein refers to phenyl, biphenyl, 1-naphthyl, 2-naphthyl, and anthracenyl, with phenyl being preferred. The term "aryl" includes such rings having zero to five substituents (preferably 0-2 substituents), selected from the group consisting of halo, alkyl, substituted alkyl (e.g., trifluoromethyl), alkenyl, substituted alkenyl, alkynyl, nitro, cyano, OH, OR$_d$, SR$_d$, NR$_d$R$_e$, NR$_d$SO$_2$R$_c$, C(=O)H, acyl, —CO$_2$H, alkoxycarbonyl, carbamyl, sulfonyl, sulfonamide, —OC(=O)R$_d$, heteroaryl, heterocyclo, cycloalkyl, phenyl, benzyl, napthyl, including phenylethyl, phenyloxy, and phenylthio, wherein R$_c$, R$_d$ and R$_e$ are defined as above. Additionally, two substituents attached to an aryl, particularly a phenyl group, may join to form a further ring such as a fused or spiro-ring, e.g., cyclopentyl or cyclohexyl or fused heterocycle or heteroaryl. When an aryl is substituted with a further ring, such ring in turn may be substituted with one to two of C$_{0-4}$alkyl optionally substituted with halogen, trifluoromethyl, alkenyl, alkynyl, nitro, cyano, OH, O(alkyl), phenyloxy, benzyloxy, SH, S(alkyl), $NH_2$, NH(alkyl), $N(alkyl)_2$, $NHSO_2$, $NHSO_2(alkyl)$, $SO_2(alkyl)$, $SO_2NH_2$, $SO_2NH(alkyl)$, $CO_2H$, $CO_2(alkyl)$, C(=O)H, C(=O)alkyl, $C(=O)NH_2$, C(=O)NH(alkyl), $C(=O)N(alkyl)_2$, OC(=O)alkyl, $OC(=O)NH_2$, OC(=O)NH(alkyl), NHC(=O)alkyl, and $NHCO_2(alkyl)$.

The term "arylene" as used herein refers to bivalent carbocyclic aromatic groups which can be optionally substituted.

The term "benzyl," as used herein, refers to $-CH_2C_6H_5$.

The term "carbamyl" refers to a functional group in which a nitrogen atom is directly bonded to a carbonyl, i.e., as in $-NR_eC(=O)R_f$ or $-C(=O)NR_eR_f$, wherein $R_e$ and $R_f$ can be hydrogen, alkyl, substituted alkyl, alkenyl, substituted alkenyl, alkoxy, cycloalkyl, aryl, heterocyclo, or heteroaryl, or they may join to form a ring.

The term "cycloalkyl," as used herein, refers to fully saturated and partially unsaturated hydrocarbon rings of 3 to 9 member in size, preferably 3 to 7 carbon atoms. The term "cycloalkyl" includes such rings having zero to four substituents (preferably 0-2 substituents), selected from the group consisting of halogen, alkyl, substituted alkyl (e.g., trifluoromethyl), alkenyl, substituted alkenyl, alkynyl, nitro, cyano, OH, oxo (=O), $OR_d$, $SR_d$, $NR_dR_e$, $NR_cSO_2$, $NR_cSO_2R_c$, C(=O)H, acyl, $-CO_2H$, alkoxycarbonyl, carbamyl, sulfonyl, sulfonamide, $-OC(=O)R_d$, =N-OH, =N-O-alkyl, aryl, heteroaryl, heterocyclo, a 4 to 7 membered carbocyclic ring, and a five or six membered ketal, e.g., 1,3-dioxolane or 1,3-dioxane, wherein $R_c$, $R_d$ and $R_e$ are defined as above. The term "cycloalkyl" also includes such rings having a phenyl ring fused thereto or having a carbon-carbon bridge of 3 to 4 carbon atoms. Additionally, when a cycloalkyl is substituted with a ring, i.e., aryl, arylalkyl, heteroaryl, heteroarylalkyl, heterocyclo, heterocycloalkyl, cycloalkylalkyl, or a further cycloalkyl ring, such ring in turn may be substituted with one to two of $C_{0-4}$alkyl optionally substituted with halogen, trifluoromethyl, alkenyl, alkynyl, nitro, cyano, oxo (=O), OH, O(alkyl), phenyloxy, benzyloxy, SH, S(alkyl), $NH_2$, NH(alkyl), $N(alkyl)_2$, $NHSO_2(alkyl)$, $SO_2(alkyl)$, $SO_2NH_2$, $SO_2NH(alkyl)$, $CO_2H$, $CO_2(alkyl)$, C(=O)H, C(=O)alkyl, $C(=O)NH_2$, C(=O)NH(alkyl), $C(=O)N(alkyl)_2$, OC(=O)alkyl, $OC(=O)NH_2$, OC(=O)NH(alkyl), NHC(=O)alkyl, and $NHCO_2(alkyl)$.

The term "cycloalkylene," as used herein, refers to bivalent saturated carbocyclic groups having three to eight carbons. The cycloalkylene groups can be optionally substituted.

The term "formyl," as used herein, refers to $-CH(=O)$.

The term "halogen," as used herein, refers to fluorine, chlorine, bromine and iodine atoms and the term "halo" refers to $-F$, $-Cl$, $-Br$, and $-I$ as substituent.

The term "haloalkyl" as used herein, refers to a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $-OCF_3$.

The term "heteroaryl," as used herein, refers to substituted and unsubstituted aromatic 5 to 7 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero to four substituents (preferably 0-2 substituents), selected from the group consisting of halo, alkyl, substituted alkyl (e.g., trifluoromethyl), alkenyl, substituted alkenyl, alkynyl, nitro, cyano, $OR_d$, $SR_d$, $NR_dR_e$, $NR_dSO_2R_c$, $SO_2R_d$, C(=O)H, acyl, $-CO_2H$, alkoxycarbonyl, carbamyl, sulfonyl, sulfonamide, $-OC(=O)R_d$, heterocyclo, cycloalkyl, aryl, or a monocyclic 4 to 7 membered aromatic ring having one to four heteroatoms, including phenylethyl, phenyloxy, and phenylthio, wherein $R_c$, $R_d$ and $R_e$ are defined as above. Additionally, when a heteroaryl is substituted with a further ring, i.e., aryl, arylalkyl, heterocyclo, heterocycloalkyl, cycloalkyl, cycloalkylalkyl, heteroarylalkyl, or a further heteroaryl ring, such ring in turn may be substituted with one to two of $C_{0-4}$alkyl optionally substituted with halogen, trifluoromethyl, alkenyl, alkynyl, nitro, cyano, oxo (=O), OH, O(alkyl), phenyloxy, benzyloxy, SH, S(alkyl), $NH_2$, NH(alkyl), $N(alkyl)_2$, $NHSO_2(alkyl)$, $SO_2(alkyl)$, $SO_2NH_2$, $SO_2NH(alkyl)$, $CO_2H$, $CO_2(alkyl)$, C(=O)H, C(=O)alkyl, $C(=O)NH_2$, C(=O)NH(alkyl), $C(=O)N(alkyl)_2$, OC(=O)alkyl, $OC(=O)NH_2$, OC(=O)NH(alkyl), NHC(=O)alkyl, and $NHCO_2(alkyl)$.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolylbenzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "heteroarylene," as used herein, refers to a bivalent cyclic aromatic group having five or six ring atoms wherein at least one ring atom is selected from the group consisting of oxygen, sulfur, and nitrogen, and the remaining ring atoms are carbon. The heteroarylene group can be optionally substituted.

The term "heteroatom," as used herein, refers to oxygen, nitrogen or sulfur atom.

The term "heterocyclo", "heterocycle" or "heterocyclyl" refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S or N). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero to four substituents (preferably 0-2 substituents), selected from the group consisting of halo, alkyl, substituted alkyl (e.g., trifluoromethyl), alkenyl, substituted alkenyl, alkynyl, nitro, cyano, oxo (=O), $OR_d$, $SR_d$, $NR_dR_e$, $NR_dSO_2R_c$, $SO_2R_d$, C(=O)H, acyl, —$CO_2H$, alkoxycarbonyl, carbamyl, sulfonyl, sulfonamide, —OC(=O)$R_d$, =N—OH, =N—O-alkyl, aryl, heteroaryl, cycloalkyl, a five or six membered ketal, e.g., 1,3-dioxolane or 1,3-dioxane, or a monocyclic 4 to 7 membered non-aromatic ring having one to four heteroatoms, wherein $R_c$, $R_d$ and $R_e$ are defined as above. The term "heterocyclo" also includes such rings having a phenyl ring fused thereto or having a carbon-carbon bridge of 3 to 4 carbon atoms. Additionally, when a heterocyclo is substituted with a further ring, i.e., aryl, arylalkyl, heteroaryl, heteroarylalkyl, cycloalkyl, cycloalkylalkyl, heterocycloalkyl, or a further heterocyclo ring, such ring in turn may be substituted with one to two of $C_{0-4}$ alkyl optionally substituted with halogen, trifluoromethyl, alkenyl, alkynyl, nitro, cyano, oxo (=O), OH, O(alkyl), phenyloxy, benzyloxy, SH, S(alkyl), $NH_2$, NH(alkyl), N(alkyl)$_2$, $NHSO_2$(alkyl), $SO_2$(alkyl), $SO_2NH_2$, $SO_2NH$(alkyl), $CO_2H$, $CO_2$(alkyl), C(=O)H, C(=O)alkyl, C(=O)$NH_2$, C(=O)NH(alkyl), C(=O)N(alkyl)$_2$, OC(=O)alkyl, OC(=O)$NH_2$, OC(=O)NH(alkyl), NHC(=O)alkyl, and $NHCO_2$(alkyl).

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include diazabicyclooctanes.

The term "heterocycloalkyl" as used herein, refers to a non-aromatic five-, six- or seven-membered ring or a bi- or tri-cyclic group having one or more heteroatoms independently selected from oxygen, sulfur, and nitrogen, wherein each 5-membered ring has zero to one double bonds and each six-membered ring has zero to 2 double bonds. The nitrogen and sulfur heteroatoms can optionally be oxidized, the nitrogen heteroatom can optionally be quaternized, and any of the above heterocyclic rings can be fused to an aryl or heteroaryl ring. Representative heterocycles include, but are not limited to: pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, morpholinyl, isothiazolidinyl, and tetrahydrofurranyl. The heterocycloalkyl groups of this invention can be optionally substituted with one, two, or three substituents independently selected from —F, —Cl, —OH, —$NO_2$, —CN, —C(O)-alkyl, —C(O)-aryl, —C(O)-heteroaryl, —$CO_2$-alkyl, —$CO_2$-aryl, —$CO_2$-heteroaryl, —C(O)$NH_2$, —C(O)NH-alkyl, —C(O)NH-aryl, —C(O)NH-heteroaryl, —OC(O)-alkyl, —OC(O)-aryl, —OC(O)-heteroaryl, —OC(O)$NH_2$, —OC(O)NH-alkyl, —OC(O)NH-aryl, —OCONH-heteroaryl, —NHC(O)-alkyl, —NHC(O)-aryl, —NHC(O)-heteroaryl, —$NHCO_2$-alkyl, —$NHCO_2$-aryl, —$NHCO_2$-heteroaryl, —NHC(O)$NH_2$, —NHC(O)NH-alkyl, —NHC(O)NH-aryl, —NHC(O)NH-heteroaryl, —$SO_2$-alkyl, —$SO_2$-aryl, —$SO_2$-heteroaryl, —$SO_2NH_2$, —$SO_2$NH-alkyl, —$SO_2$NH-aryl, —$SO_2$NH-heteroaryl, -alkyl, cycloalkyl, -cycloheteroalkyl, —$CF_3$, —$CH_2OH$, —$CH_2NH_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, and -methylthiomethyl.

The term "heterocycloalkylene" as used herein, refers to a bivalent non-aromatic five-, six- or seven-membered ring having one or more heteroatoms independently selected from oxygen, sulfur and nitrogen wherein each 5-membered ring has zero to one double bonds and each six-membered ring has zero to 2 double bonds. The heterocycloalkylene groups of this invention can be optionally substituted.

The term "hydroxyl," as used herein, refers to —OH.

The term "protecting group," as used herein, refers to an easily removable group to which are known in the art to protect a functional group, such as hydroxyl and amino, against undesirable reaction during synthetic procedures and to be selectively removable. The use of protecting groups is well-known in the art for protecting groups against undesirable reactions during a synthetic procedure and many such protecting groups are known (T. H. Greene and P. G. M. Wuts, Protective Groups in Organic Synthesis, 2nd edition, John Wiley & Sons, New York, 1991).

The term "pharmaceutically acceptable prodrugs," as used herein refers to the prodrugs of the compounds of the current invention which are suitable for use in humans and animals with acceptable toxicity, irritation, allergic response, and the like, commensurate with a reasonable benefit to risk ratio, and effective for their intended use.

The term "pharmaceutically acceptable salt," as used herein refers to those salts which are suitable for use in humans and animals with acceptable toxicity, irritation, and allergic response, etc., and are commensurate with a reasonable benefit to risk ratio. Pharmaceutically acceptable salts are well known in the art. The salts can be prepared in situ during the final step of isolation and purification of the compounds of the invention or separately prepared by reacting the compounds of the invention with an acid or base. Examples of pharmaceutically acceptable salts are salts of an amino group formed with inorganic acids such as hydrochloric acid, hydrobromic acid, phosphoric acid, and sulfuric acid or with organic acids such as acetic acid, oxalic acid, maleic acid, tartaric acid, citric acid, succinic acid, or malonic acid. Examples of pharmaceutically acceptable salts include salts of an acid group formed with inorganic bases such as sodium hydroxide, sodium carbonate, sodium phosphate, etc. Other metal salts include lithium, potassium, calcium, and magnesium. Additional pharmaceutically acceptable salts include ammonium cations formed with counterions such as halide, hydroxide, carboxylate, sulfate, phosphate, nitrate, loweralkyl sulfonate, and aryl sulfonate.

The term "prodrug," as used herein, represents compounds which can be transformed in vivo to the active parent compounds defined herein.

The term "rifamycin moiety," as used herein, comprises both its phenolic (hydroquinone) and quinone forms.

The term "ring" refers to substituted or unsubstituted carbocyclic structures, such as cycloalkyl, aryl as defined above; substituted or unsubstituted heterocyclo, such as heteroaryl or heterocyclyl as defined above. The term "bivalent ring" refers to the ring having a valency of two, such as piperazinyl —N<$(CH_2)_{2x2}$>N—.

The term "substituent," as used herein, refers to halogen, trifluoromethyl, alkenyl, alkynyl, nitro, cyano, oxo (=O), $OR_a$, $SR_a$, $NR_aR_b$, $NR_aSO_2R_c$, $SO_2R_c$, $SO_2NR_aR_b$, $CO_2R_a$, C(=O)$R_a$, C(=O)$NR_aR_b$, OC(=O)$R_a$, OC(=O)$NR_aR_b$, $NR_aC$(=O)$R_b$, $NR_aCO_2R_b$, =N—OH, =N—O-alkyl, aryl, heteroaryl, heterocyclo and cycloalkyl, wherein $R_a$, $R_b$ and $R_c$ are selected from hydrogen, alkyl, alkenyl, cycloalkyl, heterocyclo, aryl, and heteroaryl.

The term "substituted alkyl" refers to an alkyl group as defined above having one to four substituents selected from a group consisting of halogen, trifluoromethyl, alkenyl, alkynyl, nitro, cyano, oxo (=O), $OR_a$, $SR_a$, $NR_aR_b$, $NR_aSO_2R_c$, $SO_2R_c$, $SO_2NR_aR_b$, $CO_2R_a$, $C(=O)R_a$, $C(=O)NR_aR_b$, $OC(=O)R_a$, $OC(=O)NR_aR_b$, $NR_aC(=O)R_b$, $NR_aCO_2R_b$, =N—OH, =N—O-alkyl, aryl, heteroaryl, heterocyclo and cycloalkyl, wherein $R_a$, $R_b$ and $R_c$ are selected from hydrogen, alkyl, alkenyl, cycloalkyl, heterocyclo, aryl, and heteroaryl. When a substituted alkyl includes an aryl, heterocyclo, heteroaryl, or cycloalkyl substituent, said ringed systems are as defined below and thus may in turn have zero to four substituents (preferably 0-2 substituents), also as defined below. When either $R_a$, $R_b$ or $R_c$ is an alkyl or alkenyl, said alkyl or alkenyl may optionally be substituted with 1-2 of halogen, trifluoromethyl, nitro, cyano, oxo (=O), OH, O(alkyl), phenyloxy, benzyloxy, SH, S(alkyl), $NH_2$, NH(alkyl), N(alkyl)$_2$, NHSO$_2$(alkyl), SO$_2$(alkyl), SO$_2$NH$_2$, SO$_2$NH(alkyl), CO$_2$H, CO$_2$(alkyl), C(=O)H, C(=O)alkyl, C(=O)NH$_2$, C(=O)NH(alkyl), C(=O)N(alkyl)$_2$, OC(=O)alkyl, OC(=O)NH$_2$, OC(=O)NH(alkyl), NHC(=O)alkyl, and/or NHCO$_2$(alkyl).

The term "sulfonyl" refers to a sulphoxide group (i.e., —S(O)$_{1-2}$) linked to an organic radical $R_c$, as defined above.

The term "sulfonamidyl" or "sulfonamido" refers to the group —S(O)$_2$NR$_e$R$_f$, wherein $R_e$ and $R_f$ are as defined above. Preferably when one of $R_e$ and $R_f$ is optionally substituted heteroaryl or heterocycle (as defined below), the other of $R_e$ and $R_f$ is hydrogen, alkyl, or substituted alkenyl.

The term "unsaturated" is used herein to refer to a ring or group, wherein the ring or group may be fully unsaturated or partially unsaturated.

When a subscript is used as in $C_{1-8}$alkyl, the subscript refers to the number of carbon atoms the group may contain. Zero when used in a subscript denotes a bond, e.g., $C_{0-4}$alkyl refers to a bond or an alkyl of 1 to 4 carbon atoms. When used with alkoxy, thioalkyl, or alkylamino (or aminoalkyl), a subscript refers to the number of carbon atoms that the group may contain in addition to heteroatoms. Thus, for example, monovalent $C_{1-2}$alkylamino includes the groups —NH—CH$_3$, —NH—CH$_2$—CH$_3$, and —N—(CH$_3$)$_2$. A lower aminoalkyl comprises an aminoalkyl having one to four carbon atoms.

The alkoxy, thioalkyl, or aminoalkyl groups may be monovalent or bivalent. By "monovalent" it is meant that the group has a valency (i.e., power to combine with another group) of one, and by "bivalent" it is meant that the group has a valency of two. For example, a monovalent alkoxy includes groups such as —O—$C_{1-12}$alkyl, whereas a bivalent alkoxy includes groups such as —O—$C_{1-12}$alkylene-, etc.

Abbreviations:

Abbreviations as used herein have the meanings known by one skilled in the art. Specifically, Ac represents acetyl group, AOC represents allyloxycarbonyl group, BOC represents t-butoxycarbonyl group, Bn represents benzyl group, Bu represents butyl group, Bz represents benzoyl group, Cbz represents benzyloxycarbonyl group, CDI represents carbonyldiimidazole, DCM represents dichloromethane, DMAP represents 4-N,N-dimethylaminopyridine, DME represents 1,2-dimethoxyethane, DMF represents N,N-dimethylformamide, DMSO represents dimethyl sulfoxide, Et represents ethyl group, EtOAc represents ethyl acetate, Me represents methyl group, MEM represents 2-methoxyethoxymethyl group, MOM represents methoxylmethyl group, NMP represents N-methylpyrrolidinone, Ph represents phenyl group, Pr represents propyl group, TEA represents triethylamine, TFA represents trifluoroacetic acid, THF represents tetrahydrofuran, TMS, trimethylsilyl group, and Ts represents p-toluenesulfonyl group.

Broadly, one aspect of the present invention comprises a compound having Formula I, in quinone form, or Formula II, in hydroquinone form:

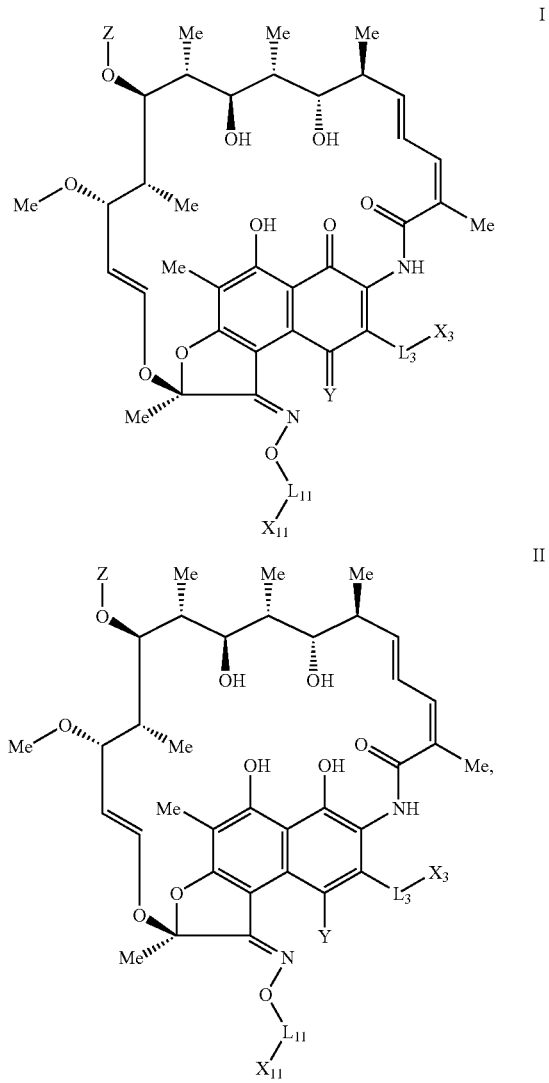

or salts, hydrates, prodrugs, or mixtures thereof;
wherein:
$L_3$ comprises any combination of 0 to 5 groups which are the same or different and are selected from —CR$_1$R$_2$—, —NR$_3$—, —O—, —C(=O)—, —S(=O)$_{0-2}$—, —C=N—, alkylene, alkenylene, alkynylene, and a bivalent ring containing 0 to 3 heteroatoms;
$X_3$ comprises —H, —OH, —NH$_2$, —CO$_2$H, halo, haloalkyl, —CN, alkyl, substituted alkyl, aryl, cycloalkyl, heteroaryl, heterocyclo, or -Q$_3$;
$L_{11}$ comprises any combination of 0 to 5 groups which are the same or different and are selected from —CR$_1$R$_2$—, —NR$_3$—, —O—, —C(=O)—, —S(=O)$_{0-2}$—, —C=N—, alkylene, alkenylene, alkynylene, and a bivalent ring containing 0 to 3 heteroatoms;

X$_{11}$ comprises —H, —OH, —NH$_2$, —CO$_2$H, halo, haloalkyl, —CN, alkyl, substituted alkyl, aryl, cycloalkyl, heteroaryl, heterocyclo, or -Q$_{11}$;

Y comprises, when the compound is Formula I, =O or =NR$_4$, and, when the compound is Formula II, —OH, —NHR$_4$, —OR$_5$, —OCH$_2$CO$_2$H, or —OCH$_2$CONR$_6$R$_7$;

Z comprises —H or —COCH$_2$R$_8$ wherein R$_8$ is —H, —OH, halo, —CN, —CO$_2$H, —CONR$_9$R$_{10}$, —NR$_{11}$R$_{12}$, —OR$_{13}$, —S(=O)$_{0-2}$R$_{14}$, or -L$_{25}$Q$_{25}$, wherein L$_{25}$ is absent or is a heterocyclo group;

wherein R$_1$ is —H, —OH, —SH, alkyl, substituted alkyl, cycloalkyl, aryl, heteroaryl, alkoxy, alkylthio, alkylamino, dialkylamino, or a heterocyclo group, wherein R$_2$, R$_3$, R$_4$, R$_5$, R$_6$, R$_7$; R$_9$, R$_{10}$, R$_{11}$, R$_{12}$, R$_{13}$, and R$_{14}$ independently are the same or different and are H, alkyl, substituted alkyl, cycloalkyl, aryl, heteroaryl, or a heterocyclo group, or wherein one or more of R$_1$ and R$_2$, R$_6$ and R$_7$, R$_9$ and R$_{10}$, and R$_{11}$ and R$_{12}$ may join together with the atoms to which they are attached to form a ring, and wherein Q$_3$, Q$_{11}$, and Q$_{25}$ are the same or different and are a therapeutic agent.

In preferred embodiments, Q$_3$, Q$_{11}$, and Q$_{25}$ are macrolides, quinolones, beta-lactams, oxazolidinones, tetracyclines, and aminoglycosides.

In further preferred embodiments, Q$_3$, Q$_{11}$, and Q$_{25}$ are the same or different and are any of the structures III to IX:

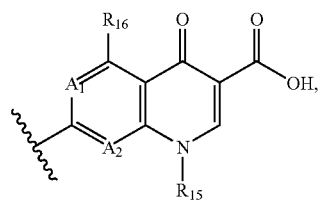

VII

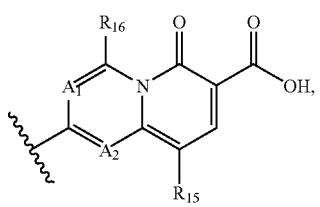

VIII

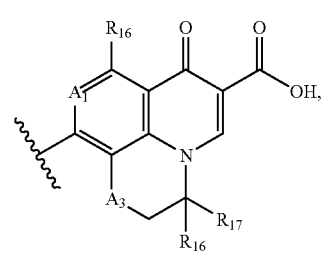

IX

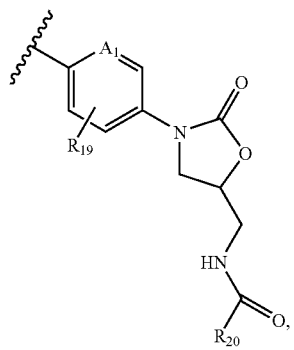

X

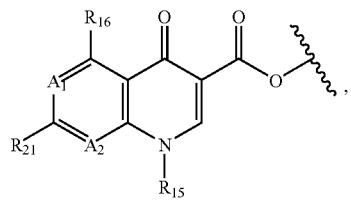

XI

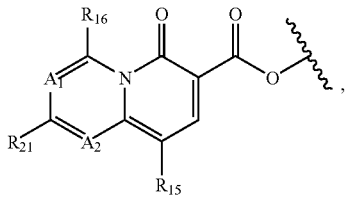

XII

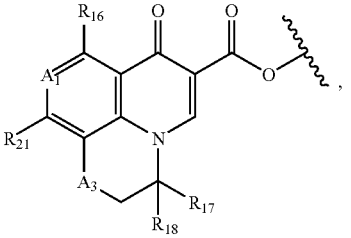

XIII wherein, A$_1$ is CH, CF, or N; A$_2$ is CH, CF, N, C—CH$_3$, C—OCH$_3$, C—OCH$_2$F, C—OCHF$_2$, or C—Cl; A$_3$ is —CH$_2$—, —O—, —S—, or —NR$_{22}$—; R$_{15}$, R$_{17}$, R$_{18}$, R$_{20}$ and R$_{22}$ independently are the same or different and are H, alkyl, substituted alkyl, cycloalkyl, aryl, heteroaryl, or a heterocyclo group; R$_{17}$ and R$_{18}$, together with the carbon to which they are attached, may form a 3-6 membered cycloalkyl ring; R$_{16}$ is —H, —NH$_2$, —NO$_2$, —F, or a C$_{1-6}$ alkyl; R$_{19}$ is —H, halo, or an alkyl group; and R$_{21}$, is a heterocyclo group.

In the most preferred embodiments, Q$_3$, Q$_{11}$, and Q$_{25}$ are the same or different and are any of the structures shown in FIG. 1.

In additional preferred embodiments, when the compound is Formula II, Y is —OH, —NHR$_4$, or —OR$_5$. In further preferred embodiments, Z represents —H or —COCH$_3$.

The compounds of Formulas I and II form salts which are also within the scope of this invention. Reference to a compound of Formulas I and II herein is understood to include reference to salts thereof, unless otherwise indicated. The term "salt(s)," as employed herein, denotes acidic and/or basic salts formed with inorganic and/or organic acids and bases. In addition, when a compound of Formulas I and II contains both a basic moiety, such as, but not limited to an amine or a pyridine or imidazole ring, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g. in isolation or purification steps which may be employed during preparation. Salts of the compounds of Formulas I and II may be formed, for example, by reacting a compound of Formulas I and II with an amount of acid or base, such as an equivalent amount, in a medium such as one in which the salt precipitates or in an aqueous medium followed by lyophilization.

The compounds of Formulas I and II which contain a basic moiety, such as, but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of Formulas I and II which contain an acidic moiety, such as, but not limited to a carboxylic acid, may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), arylalkyl halides (e.g., benzyl and phenethyl bromides), and others.

Compounds of Formulas I and II, and salts thereof, may exist in their tautomeric form (for example, as an amide or imino ether). All such tautomeric forms are contemplated herein as part of the present invention.

All stereoisomers of the present compounds, such as those, for example, which may exist due to asymmetric carbons, including enantiomeric forms (which may exist even in the absence of asymmetric carbons) and diastereomeric forms, are contemplated and within the scope of this invention. Individual stereoisomers of the compounds of this invention may, for example, be substantially free of other isomers, or may be admixed, for example, as racemates or with all other or other selected, stereoisomers. The chiral centers of the present invention can have the S or R configuration as defined by the IUPAC 1974 Recommendations.

In addition, compounds of Formulas I and II may have prodrug forms. Any compound that will be converted in vivo to provide the bioactive agent (i.e., a compound of Formulas I and II) is a prodrug within the scope and spirit of the invention.

For example, pro-drug compounds of Formulas I and II may be carboxylate ester moieties. A carboxylate ester may be conveniently formed by esterifying any of the carboxylic acid functionalities found on the disclosed ring or chain structure(s). Various forms of prodrugs are well known in the art (Bundgaard, 1985, and 1992; Bundgaard et al., 1988; Kakeya et al., 1984; Krosgaard-Larsen and Bundgaard, 1991; Widder et al., 1985).

It should further be understood that solvates (e.g., hydrates) of the compounds of Formulas I and II are also with the scope of the present invention. Methods of solvation are generally known in the art.

Compositions:

The compounds of the current invention are rifamycin derivatives of Formula I and Formula II. Formula I and Formula II are different in their oxidation states and can be transformed from one to another by mixing with a reductant (ascorbic acid) or oxidant (potassium ferrous cyanide). In one aspect, compounds of the current invention contain 9 asymmetric and 3 geometric centers. In some cases, one or more of the asymmetric or geometric centers can be converted to their opposite configurations. These stereoisomers of rifamycin are within the scope of the present invention.

EXAMPLE 1

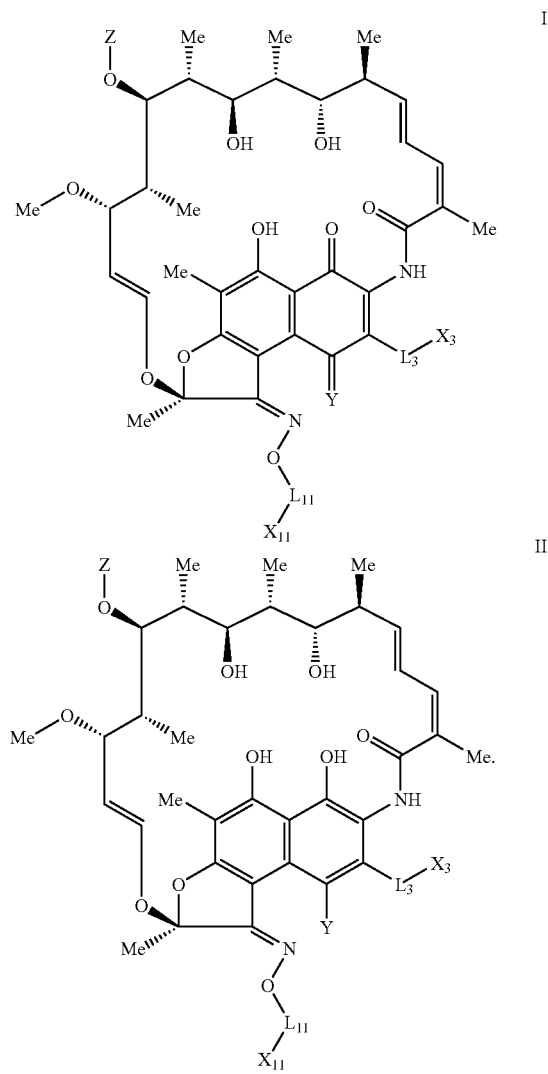

The invented rifamycin derivatives are represented by general Formula I in its quinone form, or Formula II in its hydroquinone form.

$L_3$ comprises any combination of 0 to 5 groups which can be the same or different and are selected from —$CR_1R_2$—, —$NR_3$—, —O—, —C(=O)—, —S(=O)$_{0-2}$—, —C=N—, alkylene, alkenylene, alkynylene, and a bivalent ring. $R_1$, $R_2$, and $R_3$ can be a variety of groups, including H, alkyl, substituted alkyl, cycloalkyl, aryl, heteroaryl, or a heterocyclo group. $R_1$ can also be —OH, —SH, alkoxy, alkylthio, alkylamino, or dialkylamino. When appropriate, $R_1$ and $R_2$ may join together with their respectively attached atoms to form a ring. $X_3$ can be —H, —OH, —$NH_2$, —$CO_2H$, halo, haloalkyl, —CN, alkyl, substituted alkyl, aryl, cycloalkyl, heteroaryl, heterocyclo, or -$Q_3$, wherein $Q_3$ is any structure associated with an antimicrobial or antibacterial agent. Examples of $Q_3$ include compounds belonging to the macrolide class, the fluoroquinolone class, the non-fluoroquinolone class, the oxazolidinone class, the tetracycline class, the aminoglycoside class, the beta-lactam class, the sulfonamide class, the trimethoprim class, the glycopeptide class, the lipopeptide class, and others.

$L_{11}$ represents a linker group that includes any combination of 0 to 5 groups which can be the same or different and are selected from —$CR_1R_2$—, —$NR_3$—, —O—, —C(=O)—, —S(=O)$_{0-2}$—, —C=N—, alkylene, alkenylene, alkynylene, and a bivalent ring containing 0 to 3 heteroatoms. $R_1$, $R_2$, and $R_3$ are defined as above.

$X_{11}$ represents —H, —OH, —$NH_2$, —$CO_2H$, halo, haloalkyl, —CN, alkyl, substituted alkyl, aryl, cycloalkyl, heteroaryl, heterocyclo, or -$Q_{11}$, with $Q_{11}$ defined as $Q_3$. $Q_3$ and $Q_{11}$ may be the same or different if they are both present in the same molecule.

When the compound is of Formula I, Y represents =O or =$NR_4$. When the compound is of Formula II, Y represents —OH, —$NHR_4$, —$OR_5$, —$OCH_2CO_2H$, or —$OCH_2CONR_6R_7$. $R_4$, $R_5$, $R_6$, and $R_7$ independently can be the same or different and can be H, alkyl, substituted alkyl, cycloalkyl, aryl, heteroaryl, or a heterocyclo group. When appropriate, $R_6$ and $R_7$ may joint together with their respectively attached atoms to form a ring. In preferred embodiments, when the compound is of Formula II, Y represents —OH, —$NHR_4$, or —$OR_5$.

Z represents —H or —$COCH_2R_8$, wherein $R_8$ is —H, —OH, halo, —CN, —$CO_2H$, —$CONR_9R_{10}$, —$NR_{11}R_{12}$, —$OR_{13}$, —$S(=O)_{0-2}R_{14}$, or -$L_{25}Q_{25}$, wherein $L_{25}$ is absent or is a heterocyclo group and wherein $Q_{25}$ is defined as $Q_3$. $Q_3$, $Q_{11}$ and $Q_{25}$ may be the same or different if any of them is present in the same molecule. In the natural form, rifamycins have an acetyl group at position C-25. Chemical or enzymatic hydrolysis of the acetyl group provides the de-acetylated compounds wherein Z is a hydrogen atom. The de-acetylated compounds can be further transformed to compounds where Z is a group of formula —$C(O)CH_2R_8$. $R_9$, $R_{10}$, $R_{11}$, $R_{12}$, $R_{13}$, and $R_{14}$ can be the same or different and can be a variety of groups, such as H, alkyl, substituted alkyl, cycloalkyl, aryl, heteroaryl, or a heterocyclo group. In the most preferred embodiments, Z represents —H or —$COCH_3$.

In a preferred embodiment, $Q_3$, $Q_{11}$ and $Q_{25}$ are independently the same or different and are any of the structures shown in Formulas III to IX:

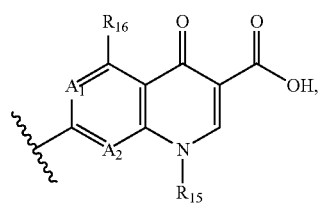

VII

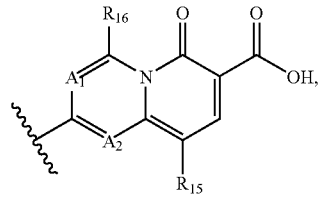

VIII

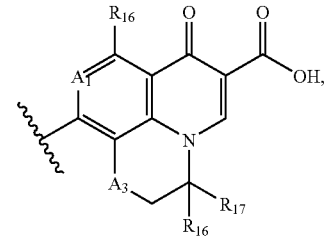

IX

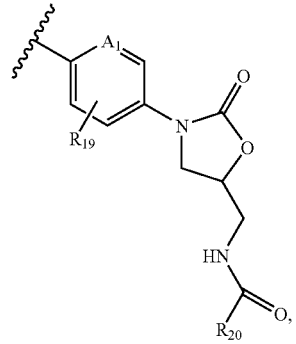

X

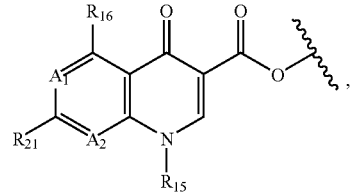

XI

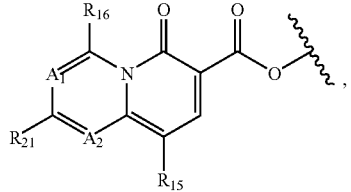

XII

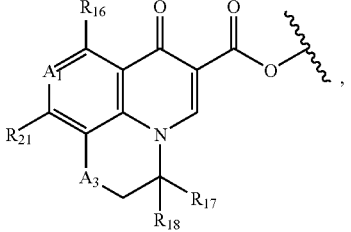

XIII wherein, $A_1$ is selected from CH, CF, or N; $A_2$ is selected from CH, CF, N, C—$CH_3$, C—$OCH_3$, C—$OCH_2F$, C—$OCHF_2$, or C—Cl; $A_3$ is selected from —$CH_2$—, —O—, —S—, or —$NR_{22}$—; $R_{15}$, $R_{17}$, $R_{18}$, $R_{20}$ and $R_{22}$ independently are the same or different and are H, alkyl, substituted alkyl, cycloalkyl, aryl, heteroaryl, or a heterocyclo group; $R_{17}$ and $R_{18}$, together with the carbon to which they are attached, may form a 3-6 membered cycloalkyl ring; $R_{16}$ is —H, —$NH_2$, —$NO_2$, —F, or a $C_{1-6}$ alkyl; $R_{19}$ is —H, halo, or an alkyl group; and $R_{21}$ is a heterocyclo group.

In a further preferred embodiment, $Q_3$, $Q_{11}$ and $Q_{25}$ are the same or different and are any of the structures shown in FIG. 1.

In the above formulas, it is also possible for one or more of the following pairs: (i) $R_1$ and $R_2$, (ii) $R_6$ and $R_7$, (iii) $R_9$ and $R_{10}$, and (iv) $R_{11}$ and $R_{12}$ to join together with their respectively attached atoms to form a ring.

Preferred compounds of the invention are as follows: 4,11-Dideoxy-4,11-dihydroxyiminorifamycin S 4,11-Dideoxy-4,11-dimethoxyiminorifamycin S 4,11-Dideoxy-4,11-dimethoxyethoxymethoxyiminorifamycin S (A); 4, 11-Dideoxy-4-methoxyethoxymethoxyimino-11-hydroxyiminorifamycin S (B); 11-Deoxy-11-hydroxyiminorifamycin S 11-Deoxy-11-(4-pyridylcarboxy)iminorifamycin S 11-Deoxy-11-acetoxyiminorifamycin S 11-Deoxy-11-methoxyethoxymethoxyiminorifamycin S 11-Deoxy-11-allyloxyiminorifamycin S 11-Deoxy-11-(2-bromoethoxyimino)rifamycin S (R/S)-11-Deoxy-11-[2-[4-(3-carboxy-1-cyclopropyl-6-fluoro-8-methoxy-4-oxo-1,4-dihydroquinolin 7-yl)-2-methylpiperazin-1-yl]ethoxyimino] rifamycin S 11-Deoxy-1-[2-[4 (3-carboxy-1-cyclopropyl-6-fluoro-4-oxo-1,4-dihydroquinolin-7-yl)piperazin-1-yl] ethoxyimino]rifamycin S 11-Deoxy-11-[2-[6-(3-carboxy-1-cyclopropyl-6-fluoro-8-methoxy-4-oxo-1,4-dihydroquinolin-7-yl) octahydro-pyrrolo[3,4-b]pyridin-1-yl] ethoxyimino]rifamycin S 11-Deoxy-11-[2-[4-{4-[5-(acetylamino-methyl)-2-oxo-oxazolidin-3-yl]-2-fluoro-phenyl}-piperazin-1-yl]ethoxyimino]rifamycin S 11-Deoxy-11-{2-[4-(pyridin-2-yl)piperazin-1-yl] ethoxyimino}rifamycin S 11-Deoxy-11-{2-[4-(3-trifluoromethyl-phenyl)-piperazin-1-yl]ethoxyimino}rifamycin S 11-Deoxy-11-{2-[4-(isoquinoline-8-sulfonyl)-piperazin-1-yl]-ethoxyimino}rifamycin S 11-Deoxy-11-{2-[bis-(2-hydroxy-ethyl)-amino]ethoxyimino}rifamycin S 11-Deoxy-11-[2-(3,5-dimethyl-piperazin-1-yl)ethoxyimino]rifamycin S 11-Deoxy-11-[2-(4-methylpiperazin-1-yl)ethoxyimino] rifamycin S 11-Deoxy-11-[2-(4-hydroxypiperadin-1-yl)ethoxyimino]rifamycin S 11-Deoxy-11-[2-morpholin-4-yl) ethoxyimino]rifamycin S 11-Deoxy-11-[2-(4-benzylpiperazin-1-yl)ethoxyimino]rifamycin S 11-Deoxy-11-{2-[4-(2-hydroxy-phenyl)piperazin-1-yl] ethoxyimino}rifamycin S 11-Deoxy-3-hydroxymethyl-11-(4-carboxymethoxyimino)-rifamycin S 11-Deoxy-3-(morpholin-4-yl)-11-(4-carboxymethoxyimino)-rifamycin S 11-Deoxy-3-(morpholin-4-yl)-11-{2-oxo-2-[4-(3-carboxy-1-cyclopropyl-6-fluoro-4-oxo-1,4-dihydroquinolin-7-yl) piperazin-1-yl]ethoxyimino}rifamycin S 11-Deoxy-3-(morpholin-4-yl)-11-{2-oxo-2-[4-(3-carboxy-1-cyclopropyl-6-fluoro-8-methoxy-4-oxo-1,4-dihydroquinolin-7-yl)-2-methylpiperazin-1-yl]ethoxyimino}rifamycin S (R/S)-11-Deoxy-3-(morpholin-4-yl)-11-{2-oxo-2-[4-(3-carboxy-1-cyclopropyl-6-fluoro-8-chloro-4-oxo-1,4-dihydroquinolin-7-yl)-3-aminopyrrolidin-1-yl]ethoxyimino}rifamycin S 11-Deoxy-11-{2-oxo-2-[4-(3-carboxy-1-cyclopropyl-6-fluoro-4-oxo-1,4-dihydroquinolin-7-yl)piperazin-1-yl] ethoxyimino}rifamycin S 11-Deoxy-3-[4-(3-carboxy-1-cyclopropyl-6-fluoro-4-oxo-1,4-dihydroquinolin-7-yl) piperazin-1-yl]-11-hydroxyiminorifamycin S 11-Deoxy-3-(morpholin-4-yl)-11-hydroxyiminorifamycin S 11-Deoxy-3-(morpholin-4-yl)-11-methoxyiminorifamycin S 11-Deoxy-3-(morpholin-4-yl)-11-allyloxyiminorifamycin S 11-Deoxy-11-hydroxyimino-3-(4-methylpiperazin-1-yl) aminomethenylrifamycin SV; 11-Deoxy-11-hydroxyimino-3-(4-methylpiperazin-1-yl)aminomethenylrifamycin S 3-[4-(3-Carboxy-1-cyclopropyl-6-fluoro-4-oxo-1,4-dihydroquinolin-7-yl)piperazin-1-yl-aminomethylenyl]-11-deoxy-11-hydroxyiminorifamycin SV; and (R/S)-3-[4-(3-Carboxy-1-cyclopropyl-6-fluoro-8-methoxy-4-oxo-1,4-dihydroquinolin-7-yl)-2-methyl-piperazin-1-yl-aminomethylenyl]-11-deoxy-11-hydroxyiminorifamycin SV.

EXAMPLE 2

Pharmaceutical Applications

The compounds of Formulas I and II disclosed herein can be used in a variety of pharmaceutical applications. In one embodiment, the compounds may be used as antimicrobial agents for the treatment of infectious disorders that are caused by microbial organisms, such as bacteria.

In one embodiment, compositions, for treating or preventing infectious disorders are provided, comprising a compound as disclosed herein in combination with a pharmaceutically acceptable carrier; with one or more antibiotics of other classes, such as macrolides, fluoroquinolones, oxazolidinones.

In another embodiment, there is provided a dosage amount of a compound as disclosed herein in an effective amount for the treatment, prevention or alleviation of a disorder, such as an infectious disorder.

The compounds of Formulas I and II can be screened for activity against different organisms and appropriate dosages may be determined using methods available in the art.

The compounds may be used to treat a subject to treat, prevent, or reduce the severity of an infection. Subjects include animals, plants, blood products, cultures and surfaces such as those of medical or research equipment, such as glass, needles, tubing and other implanted devices.

In one embodiment, methods of treating or preventing an infectious disorder in a subject, such as a human or other animal subject, are provided, by administering an effective amount of a compound as disclosed herein to the subject. In one embodiment, the compound is administered in a pharmaceutically acceptable form optionally in a pharmaceutically acceptable carrier. As used herein, an "infectious disorder" is any disorder characterized by the presence of a microbial infection, such as bacterial infections. Such infectious disorders include, for example central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients. The compounds and compositions comprising the compounds can be administered by routes such as topically, locally or systemically. Systemic application includes any method of introducing the compound into the tissues of the body, e.g., intrathecal, epidural, intramuscular, transdermal, intravenous, intraperitoneal, subcutaneous, sublingual, rectal, and oral administration. The specific dosage of antimicrobial to be administered, as well as the duration of treatment, may be adjusted as needed.

The compounds of the invention may be used for the treatment or prevention of infectious disorders caused by a variety of bacterial organisms. Examples include Gram positive and Gram negative aerobic and anaerobic bacteria, including Staphylococci, for example *S. aureus*; Enterococci, for example *E. faecalis*; Streptococci, for example *S. pneumoniae*; Haemophilus, for example *H. influenza*; Moraxella, for example *M. catarrhalis*; and Escherichia, for example *E. coli*. Other examples include Mycobacteria, for example *M. tuberculosis*; intercellular microbes, for example Chlamydia and Rickettsiae; and Mycoplasma, for example *M. pneumoniae*; and Helicobacter pylori.

The pharmaceutical composition of the present invention comprises a therapeutically effective amount of a compound of the current invention formulated together with one or more pharmaceutically acceptable carriers. Injectable preparations can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of a drug, it is often desirable to slow the absorption of the drug through subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils, glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and the following: 1) fillers or extenders such as starches, lactose, sucrose, glucose, mannitol, and silicic acid, 2) binders such as, carboxymethylcellulose, alginates, gelatin, polyvinylpyrrolidinone, sucrose, and acacia, 3) humectants such as glycerol, 4) disintegrating agents such as agar-agar, calcium carbonate, potato or tapioca starch, alginic acid, certain silicates, and sodium carbonate, 5) solution retarding agents such as paraffin, 6) absorption accelerators such as quaternary ammonium compounds, 7) wetting agents such as, cetyl alcohol and glycerol monostearate, 8) absorbents such as kaolin and bentonite clay, and 9) lubricants such as talc, calcium stearate, magnesium stearate, solid polyethylene glycols, sodium lauryl sulfate, and mixtures thereof. In the case of capsules, tablets and pills, the dosage form can also comprise buffering agents. Solid compositions of a similar type can also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient only, or preferentially, in a certain part of the intestinal tract, optionally, in a delayed manner. Examples of embedding compositions which can be used include polymeric substances and waxes. The active compounds can also be in microencapsulated form with one or more excipients as noted above.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as can be required. Ophthalmic formulation, ear drops, eye ointments, powders and solutions are also contemplated as being within the scope of this invention. The ointments, pastes, creams and gels can contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or animal by administering to the patient a therapeutically effective amount of a compound of the invention, in such amounts and for such time as is necessary to achieve the desired therapeutic effects. The term "therapeutically effective amount" of a compound of the invention is meant a sufficient amount of the compound to treat bacterial infections, at a reasonable benefit to risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or animals in single or in divided doses can be in amounts, for example, from 0.1 to 100 mg/kg body weight or preferably from 0.25 to 25 mg/kg body weight. Single dose compositions can contain such amounts or submultiples thereof to make up the daily dose. In general, treatment regimens according to the present invention comprise administration to an infected patient of such treatment from about 10 mg to about 2000 mg of the compounds of this invention per day in single or multiple doses. The compounds of current invention can be administered orally, rectally, parenterally, intracistemally, intravaginally, intraperitoneally, topically, bucally, or as an oral or nasal spray.

Biological Activity:

Representative compounds were assayed for antimicrobial activity as follows: Minimum Inhibitory Concentrations ("MICs") were determined by the microbroth dilution method as per NCCLS guidelines (National Committee for Clinical Laboratory Standards. 2000. Methods for dilution antimicrobial susceptibility tests for bacteria that grow aerobically, 5th ed. M7-A5. National Committee for Clinical Laboratory Standards, Wayne, Pa.), except that all growth incubations were conducted at 37° C. Bacterial cultures were tested in the following bacteriological media: S. aureus, S. epidermidis, and E. coli in Cation-Adjusted Mueller-Hinton Broth, S. pneumoniae in THY Broth supplemented with 1 mg/mL catalase under 5% $CO_2$ atmosphere, S. pyogenes in THY Broth, E. faecalis in BHI Broth, H. influenzae in BHI Broth supplemented with 0.75 µL of 1 mg/mL NAD and 150 µL of 1 mg/ml hematin per 5 mL, and M. smegmatis in Middlebrook Broth plus ADC Enrichment. The antimicrobial activity of the example compounds of the current invention are shown in Table 1.

S. aureus ATCC 2213, S. epidermidis ATCC 12228, S. pneumoniae ATCC6303, S. pyogenes ATCC 19615 and E. faecalis ATCC 29212 are rifampin-susceptible Gram-positive strains. Rifampin exhibits excellent activity against these organisms with MICs between 0.013 and 1 µg/ml. The compounds of the current invention show further improved activity against these strains with MICs as low as 0.0002 µg/ml. H. influenzae ATCC 10211 and E. coli ATCC 25922 are Gram-negative bacteria. Rifampin has intrinsically weaker activity against these organisms with MICs between 0.24 and 16 µg/ml. Compounds of the current invention also demonstrate improved activity against these strains with MICs as low as 0.03 µg/ml. In addition, rifampin exhibits low activity against a mycobacterial strain M. smegamatis ATCC 700084 with a MIC 64 µg/ml. A few compounds of the current invention show potent activity against this strain with a MIC as low as 0.5 µg/ml.

Most importantly, compounds of the current invention demonstrate excellent activity against rifampin-resistant organisms. S. aureus ATCC 29213 $RpoB^{H418Y}$ is a rifampin-resistant strain with a mutation in the RpoB gene of RNA polymerase. This mutation results in a significant increase in the MIC for rifampin to 8 µg/ml from its wild type MIC of 0.008 µg/ml. Compounds of the current invention exhibit potent activity against this resitant strain with a MIC as low as 0.125 µg/ml. S. aureus ATCC 29213 $RpoB^{D417Y}$ is a high level rifampin-resistant strain due to a critical mutation in RpoB gene of RNA polymerase with a MIC is >64 µg/ml for rifampin. Selected compounds of the current invention have activity against this highly rifampin-resistant strain with MICs in the 0.25 µg/ml level. S. aureus EN1252a $gyrA^{S84L}$ $grlA^{S80F}$ is a quinolone-resistant strain due to double gene mutations of DNA gyrase and topoisomerase IV. The MIC for ciprofloxacin against this strain is 8 µg/ml. Compounds of the current invention demonstrate potent activity against this strain with MICs range of 0.004 µg/ml to 0.5 µg/ml.

TABLE 1

Antimicrobial activity (MIC, mcg/ml) of selected compounds

| Organism | | rifampin | cipro | Examples 4-40 |
|---|---|---|---|---|
| Staphylococcus aureus ATCC29213 | rifS | 0.008 | 0.25 | 0.004-0.5 |
| Staphylococcus aureus ATCC29213 $rpoB^{H418Y}$ | rifR | 8 | 0.25 | 0.125-16 |
| Staphylococcus aureus ATCC29213 $rpoB^{D417Y}$ | rifR | >64 | 0.25 | 0.25-32 |
| Staphylococcus aureus EN1252a[a] $gyrA^{S84L}$ $grlA^{S80F}$ | cipR | 0.004 | 8 | 0.004-0.5 |
| Staphylococcus epidermidis ATCC12228 | rifS | 0.03 | 0.125 | 0.0005-0.063 |
| Streptococcus pneumoniae ATCC6303 | rifS | 0.061 | 1 | 0.0002-0.125 |

TABLE 1-continued

Antimicrobial activity (MIC, mcg/ml) of selected compounds

| Organism | | rifampin | cipro | Examples 4-40 |
|---|---|---|---|---|
| *Streptococcus pyogenes* ATCC19615 | rifS | 0.013 | 0.5 | 0.0005-0.063 |
| *Enterococcus faecalis* ATCC29212 | rifS | 1 | 0.5 | 2-32 |
| *Haemophilus influenzae* ATCC10211 | rifS | 0.24 | 0.008 | 0.03-2 |
| *Escherichia coli* ATCC25922 | rifS | 16 | 0.03 | 0.125-8 |
| *Mycobacterium smegmatis* ATCC700084 | rifS | 64 | 0.125 | 0.5-64 |

[a]For strain MT1222 see: Ince & Hooper, Antimicrobial Agents and Chemotherapy, 2000, 44, 3344-50.

EXAMPLE 3

Synthetic Methods

The compounds of the current invention can be better understood in connection with the following general synthetic schemes. The synthetic procedures shown in Schemes 1 to 7 are for illustration purposes and are not intended to limit the scope of the invention. It will be apparent to one skilled in the art that the compounds of the current invention can be prepared by a variety of synthetic routes, including but not limited to substitution of appropriate reagents, solvents or catalysts, change of reaction sequence, and variation of protecting groups.

The rifamycin C-11 oxime derivatives of this invention may be prepared by the methods illustrated in Schemes 1 through 7. Rifamycin SV sodium salt, rifabutin and other starting materials are either commercially available or could be prepared according to the known literature. For all schemes and compounds, the groups X, Y, Z, $L_3$, $X_3$, $L_{11}$, and $X_{11}$ used herein are defined as described above for compounds of Formula I or Formula II. It is to be understood that the compounds of Formula I and Formula II may be inter-converted via an oxidation and reduction process, affected by an oxidant, such as potassium ferrocyanide, or a reductant, such as ascorbic acid.

Figure 2:
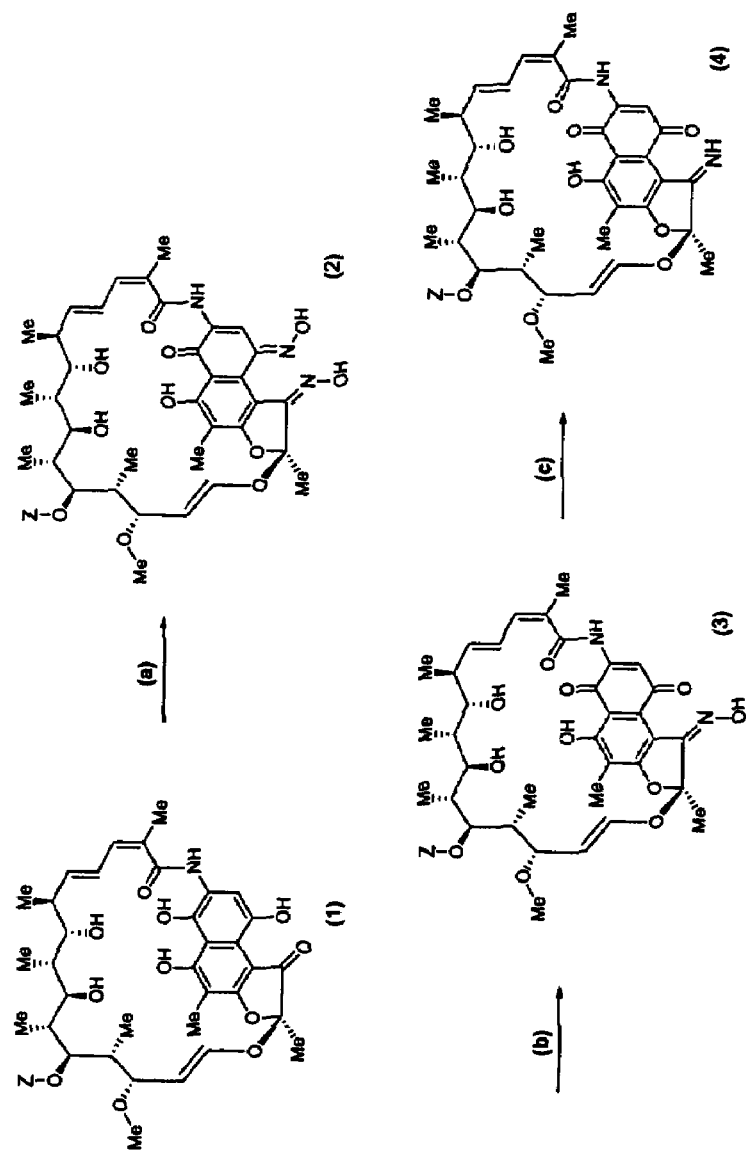
FIG. 2 shows a general synthetic procedure entitled Scheme 1.

As shown in FIG. 2, the exemplary compounds (2) to (4) described in Scheme 1 within the scope of Formula II of this invention may be prepared by the following process. Starting from compound (1), such as rifamycin SV or its sodium salt or its quinone form, the compound (2) may be prepared by treatment of compound (1) with hydroxylamine (or its HCl salt) in solvent, such as methanol, THF, acetonitrile, in the presence or absence of a base such as pyridine, TEA or sodium hydrogen carbonate. The reaction may be conducted at temperature range from about 0° C. to 50° C., while the reaction time may vary from 2 hours to 3 days.

Selective reduction with a reducing agent like tin (II) chloride or titanium (III) chloride in solvent such as THF/MeOH/H$_2$O, may provide compound (3), which may be further reduced to compound (4) using similar reaction conditions as shown in Scheme I. The reaction may be conducted at temperature range from about −10° C. to 50° C., while the reaction time may vary from 2 hour to 3 days.

Figure 3:
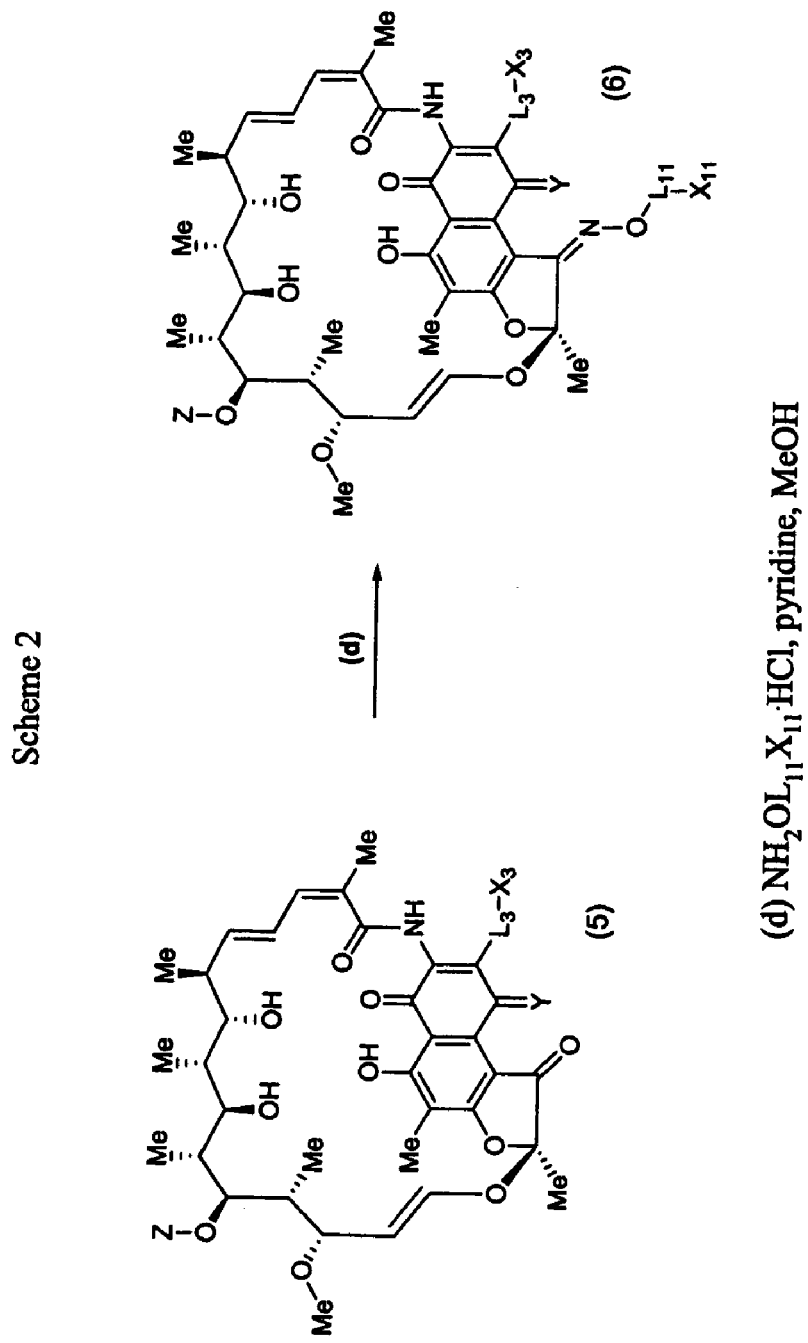
FIG. 3 shows a general synthetic procedure entitled Scheme 2.

As shown in Scheme 2 in FIG. 3, when there is a substituted group on the C-3 position, the compounds (6) of Formula II may be prepared directly from the reaction of compound (5), such as 3-(morpholin-4-yl)-rifamycin S, with NH$_2$OL$_{11}$X$_{11}$, such as carboxymethoxyamine (or its HCl salt, wherein: $L_{11}$ is CH$_2$, $X_{11}$, is CO$_2$H) in a solvent, such as methanol, THF, acetonitrile, in the presence of a base such as pyridine.

Figure 4:
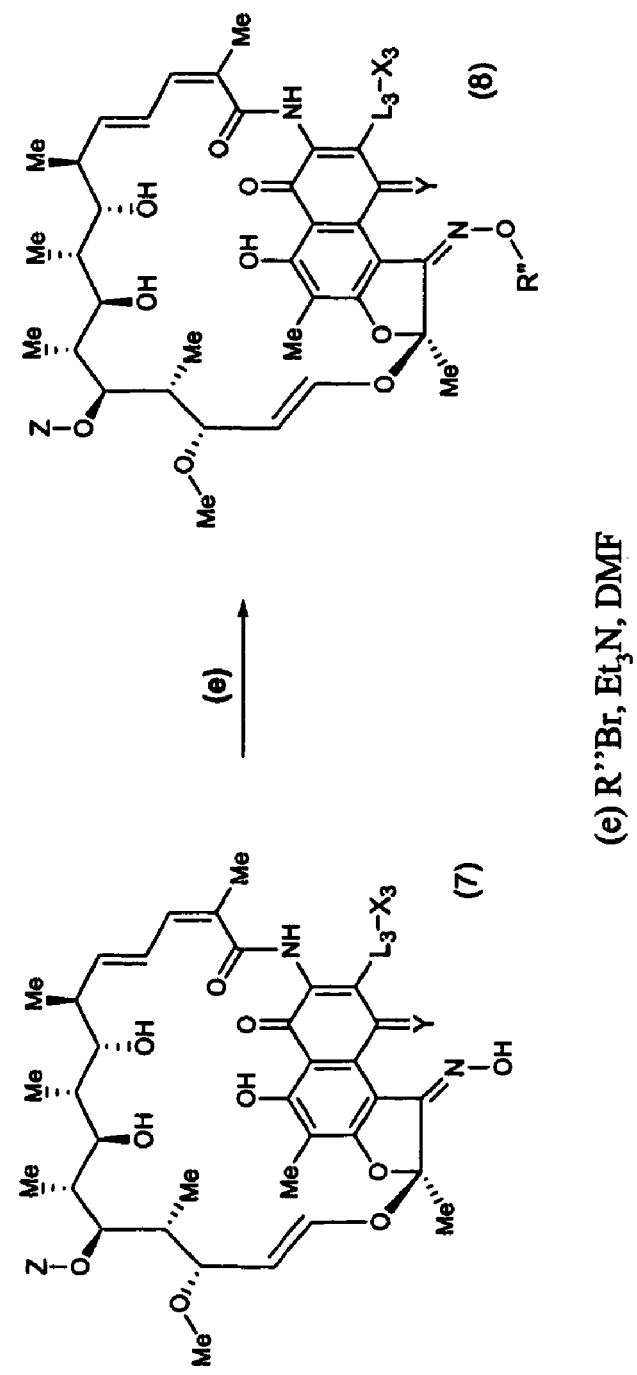
FIG. 4 shows a general synthetic procedure entitled Scheme 3.

Alternatively, as illustrated by Scheme 3 in FIG. 4, compounds (8) of Formula II may be prepared by direct alkylation of 11-deoxy-11-hydroxyiminorifamycins (7). Treatment of (7) with an alkyl halide such as 1,2-dibromide in solvent, such as DMF, in the presence of a base, such as TEA, provides compound (8) of Formula II. The reaction may be conducted at a temperature range from about 20° C. to 90° C., while the reaction time may vary from 2 hours to 3 days. Alkali iodide may be utilized to accelerate the reaction.

Further, the compounds of Formula II may be prepared as described in Scheme 4 in FIG. 5. In a typical reaction, the compound (9), prepared as above, may be reacted with an acid anhydride or acyl chloride in solvent, like DCM in the presence of a base, such as TEA, to provide compound (10) of Formula II (wherein: $A_1$ is "O", $A_2$ is "C=O). The reaction may be conducted at temperature from about −40° C. to 50° C., while the reaction time may vary from 10 min to 10 hours.

Figure 6:
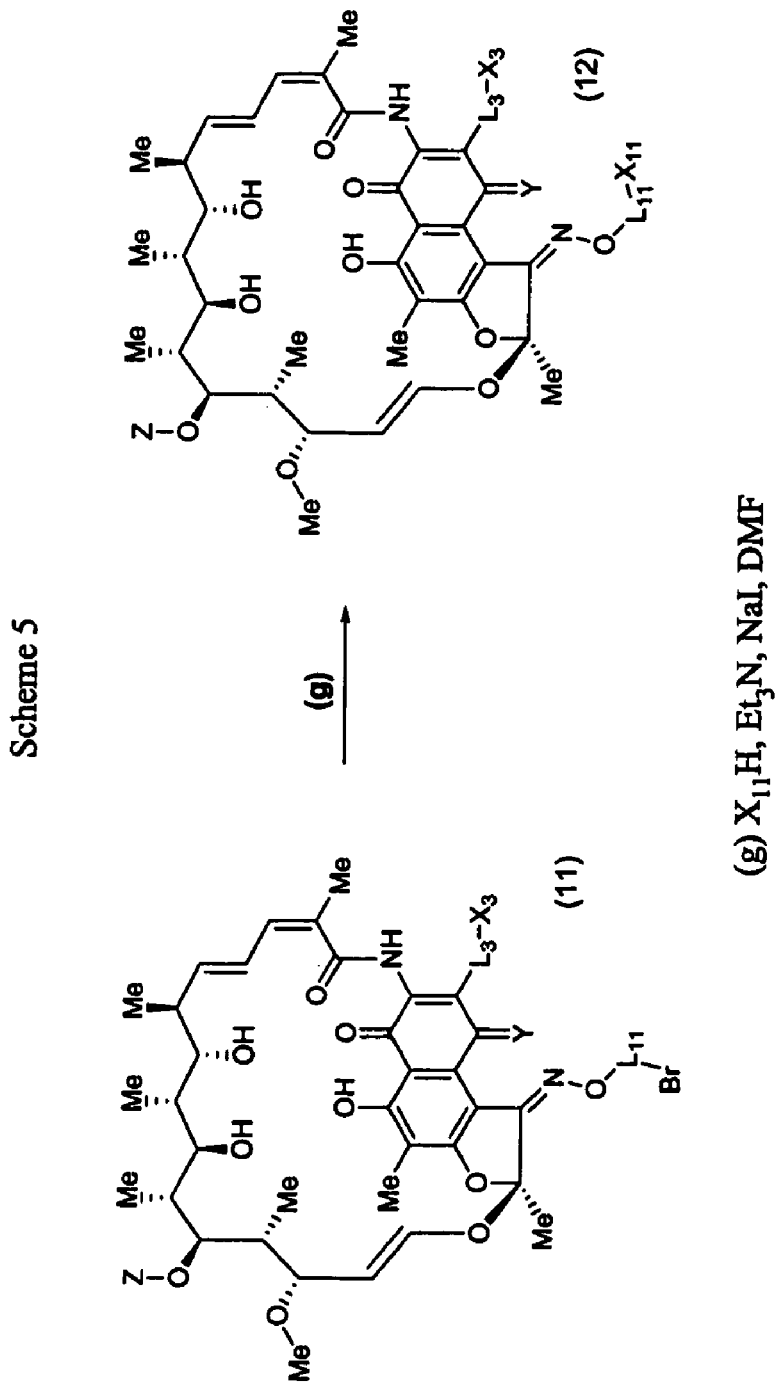
FIG. 6 shows a general synthetic procedure entitled Scheme 5.

Further, the compounds of Formula II may be prepared as described in Scheme 5 in FIG. 6. In general, the bromide in the compound of formula (11), prepared using the process disclosed above, may be substituted by a nucleophile such as an amine, such as morpholine, a thiol, such as methane thiol, an alcohol, such as methanol, a nucleophilic antibiotic or its derivatives, such as ciprofloxacin or linezolid, in solvent, such as DMF, in the presence of a base, such as TEA, and an alkali salt, such as sodium iodide compounds of Formula II.

Figure 7:
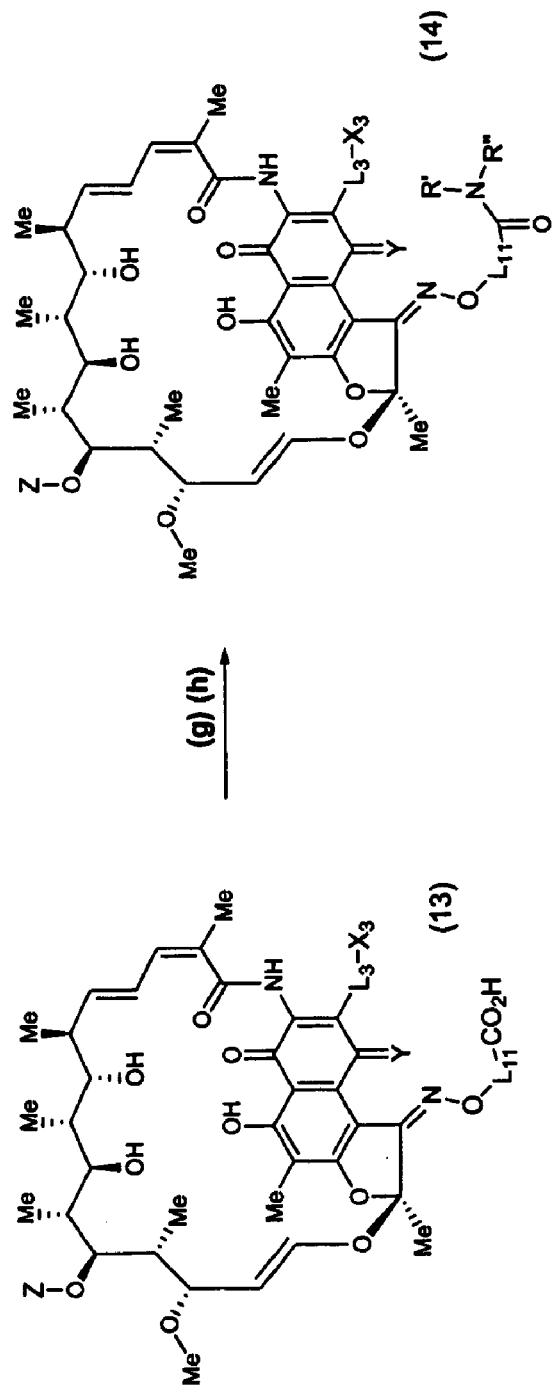
FIG. 7 shows a general synthetic procedure entitled Scheme 6.

Further, the compounds of Formula II may be prepared as described in Scheme 6 in FIG. 7. In general, carboxylic acid in compound (13) may be first transformed to an active ester by treatment with activating agents, such as N-hydroxyl succinimide and EDC in solvent, THF in the presence of a catalyst, or DMAP, then the activated ester may react with a nucleophile such as an amine, such as morpholine, a thiol, such as methane thiol, an alcohol, such as methanol, a nucleophilic antibiotic or its derivatives, such as ciprofloxacin or linezolid, in solvent, such as DMF, in the presence or absence of a base, such as TEA, to provide an amide (14) which is within the scope of Formula II.

Figure 8:
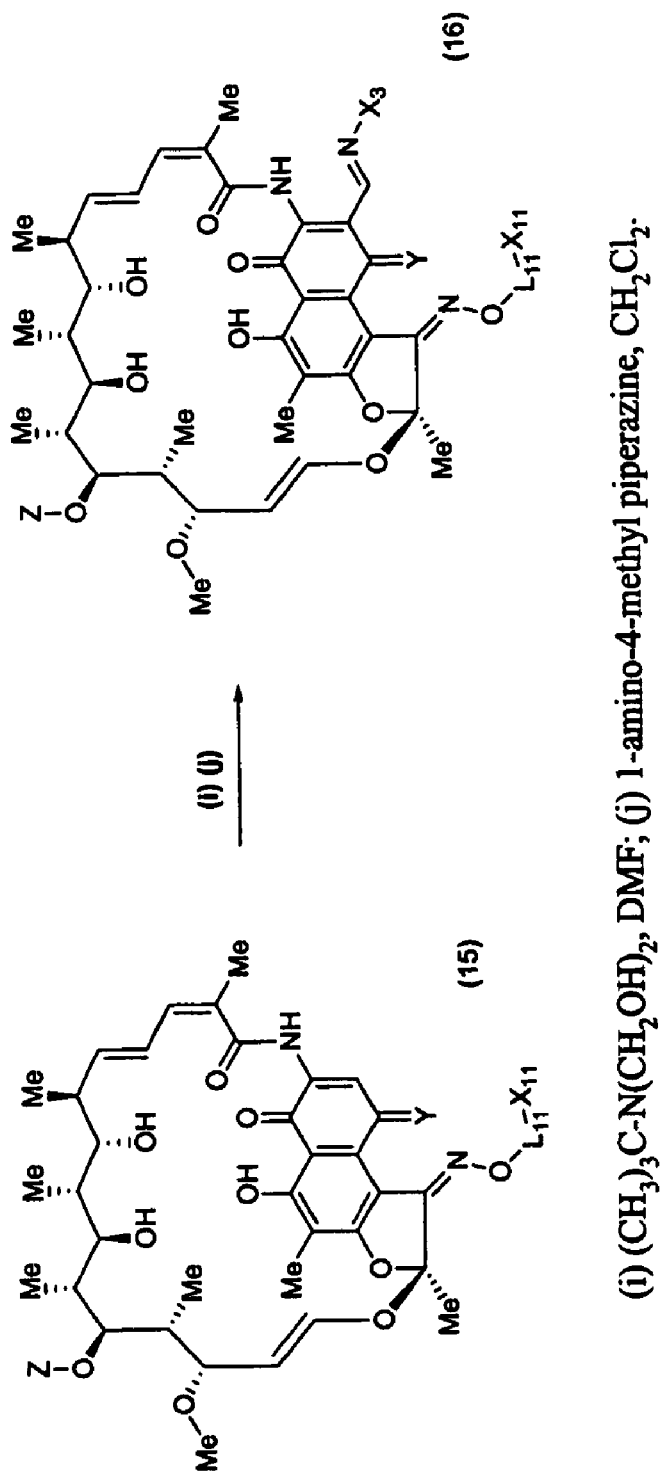
FIG. 8 shows a general synthetic procedure entitled Scheme 7.

The compounds of Formula II where $L_3$ is —C=N— may be prepared as shown in Scheme 7 in FIG. 8. Compound (15) may be reacted with a Schiff base, such as N,N-dihydroxymethyl tert-butylamine, in solvent, such as DMF, followed by addition of a hydrazine, such as 1-amino-4-methylpiperazine, to provide the compound (14) of Formula II.

Specific Compositions:

The compounds of the current invention may be better understood with reference to the following specific examples, which are representative of some of the embodiments of the invention, and are not intended to limit the invention.

All starting material used in these specific examples were either purchased from commercial sources or prepared according to published procedures. Operations involving moisture and/or oxygen sensitive materials are conducted under an atmosphere of nitrogen. Flash chromatography is performed using silica gel 60 as normal phase adsorbent or C18 silica gel as reverse phase adsorbent. Thin layer chromatography ("TLC") and preparative thin layer chromatography ("PTLC") are performed using pre-coated plates purchased from E. Merck and spots are visualized with ultraviolet light followed by an appropriate staining reagent. Nuclear magnetic resonance ("NMR") spectra were recorded on a Varian 400 MHz magnetic resonance spectrometer. $^1$H NMR chemical shift are given in parts-per million ($\delta$) downfield from TMS using the residual solvent signal (CHCl$_3$=$\delta$ 7.27, CH$_3$OH=$\delta$ 3.31) as internal standard. $^1$H NMR information is tabulated in the following format: number of protons, multiplicity (s, singlet; d, doublet; t, triplet; q, quartet; m, multiplet; td, triplet of doublet; dt, doublet of triplet), coupling constant (s) (J) in hertz. The prefix app is occasionally applied in cases where the true signal multiplicity is unresolved and prefix br indicates a broad signal. Electro spray ionization mass spectra are recorded on a Finnegan LCQ advantage spectrometer.

EXAMPLE 4

4, 11-Dideoxy-4,11-dihydroxyiminorifamycin S

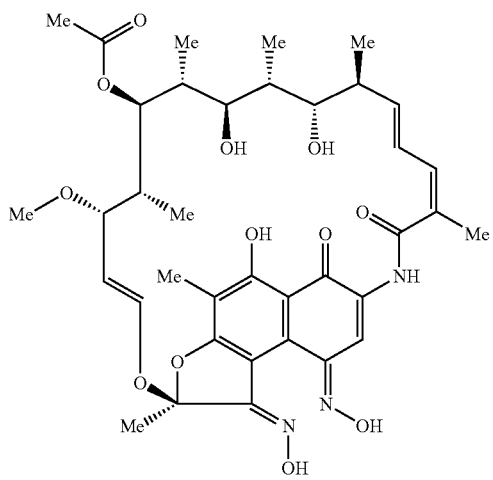

Synthesis: To a stirred solution of Rifamycin SV sodium salt (10.0 g, 13.9 mmol) in MeOH (150 mL) was added pyridine (14.0 mL, 0.18 mol) and hydroxylamine hydrochloride (12.1 g, 0.17 mol). This was allowed to stir overnight at room temperature. The resultant solution was partitioned between ethyl acetate and water. The organic layer was separated, dried over sodium sulfate, concentrated in vacuo to dryness. The crude product was purified by silica gel column chromatography (2% MeOH/DCM) to give the title compound as an orange solid (8.4 g, 83%). ESI MS m/z 726.3 (M+H)$^+$; $^1$H NMR (400 MHz, CDCl$_3$) $\delta$ 14.04 (s, 1H), 8.99 (s, 1H), 8.68 (s, 1H), 6.41-6.27 (m, 3H), 5.89 (dd, J=6.0, 11.6 Hz, 1H), 5.33 (dd, J=9.2, 12.0 Hz, 1H), 4.64 (d, J=11.0 Hz, 1H), 3.57 (d, J=9.6 Hz, 1H), 3.33 (dd, J=2.8, 8.2 Hz, 1H), 3.11 (s, 3H), 3.03 (d, J=11.0 Hz, 1H), 2.38-2.33 (m, 1H), 2.27 (s, 3H), 2.11 (s, 3H), 2.09 (s, 3H), 1.99 (s, 3H), 1.99-1.95 (m, 1H), 1.76-1.72 (m, 1H), 1.38-1.32 (m, 1H), 1.01 (d, J=7.2 Hz, 3H), 0.82 (d, J=6.4 Hz, 3H), 0.62 (d, J=7.2 Hz, 3H), 0.04 (d, J=6.4 Hz, 3H).

EXAMPLE 5

4, 11-Dideoxy-4, 11-dimethoxyiminorifamycin S

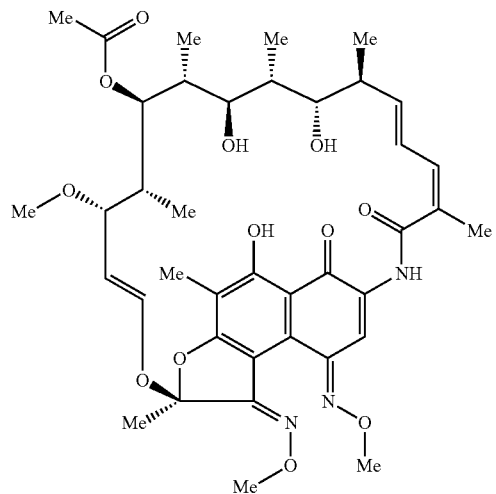

Synthesis: To a stirred solution of 4, 11-dideoxy-4,11-dihydroxyiminorifamycin S (16.0 mg, 0.022 mmol) in acetonitrile (0.5 mL) was added potassium carbonate (10.0 mg, 0.072 mmol) and iodomethane (6 μL, 0.096 mmol). The reaction mixture was allowed to stir for 40 hours at room temperature. The resultant solution was partitioned between ethyl acetate and water. The organic layer was separated, washed with brine, dried over sodium sulfate and concentrated in vacuo to dryness. The crude product was purified by preparative thin layer chromatography (PTLC) (8% MeOH/DCM) to give the title compound as an orange solid (6.0 mg, 32%). ESI MS m/z 754.2 (M+H)$^+$; $^1$H NMR (400 MHz, CDCl$_3$) $\delta$ 13.24 (s, 1H), 8.69 (s, 1H), 8.46 (s, 1H), 6.43 (dd, J=10.4, 15.6 Hz, 1H), 6.23 (d, J=10.8 Hz, 1H), 6.06 (dd, J=6.8, 15.6 Hz, 1H), 6.06 (d, J=13.2 Hz, 1H), 5.10 (dd, J=6.8, 13.2 Hz, 1H), 4.81 (d, J=9.6 Hz, 1H), 4.28 (s, 3H), 4.07 (s, 3H), 3.69 (d, J=9.6 Hz, 1H), 3.68 (br s, 2H), 3.43 (dd, J=1.6, 7.2 Hz, 1H), 3.11 (s, 3H), 3.01 (dd, J=1.6, 10.4 Hz, 1H), 2.42-2.35 (m, 1H), 2.27 (s, 3H), 2.08-2.00 (m, 1H), 2.06 (s, 3H), 2.05 (s, 3H), 2.03 (s, 3H), 1.82-1.76 (m, 1H), 1.62-1.56 (m, 1H), 1.03 (d, J=6.8 Hz, 3H), 0.86 (d, J=6.8 Hz, 3H), 0.68 (d, J=6.4 Hz, 3H), 0.14 (d, J=7.2 Hz, 3H).

EXAMPLE 6

4, 11-Dideoxy-4, 11-dimethoxyethoxymethoxyimi-norifamycin S (A) and 4, 11-Dideoxy-4-methoxy-ethoxymethoxyimino-11-hydroxyiminorifamycin S (B)

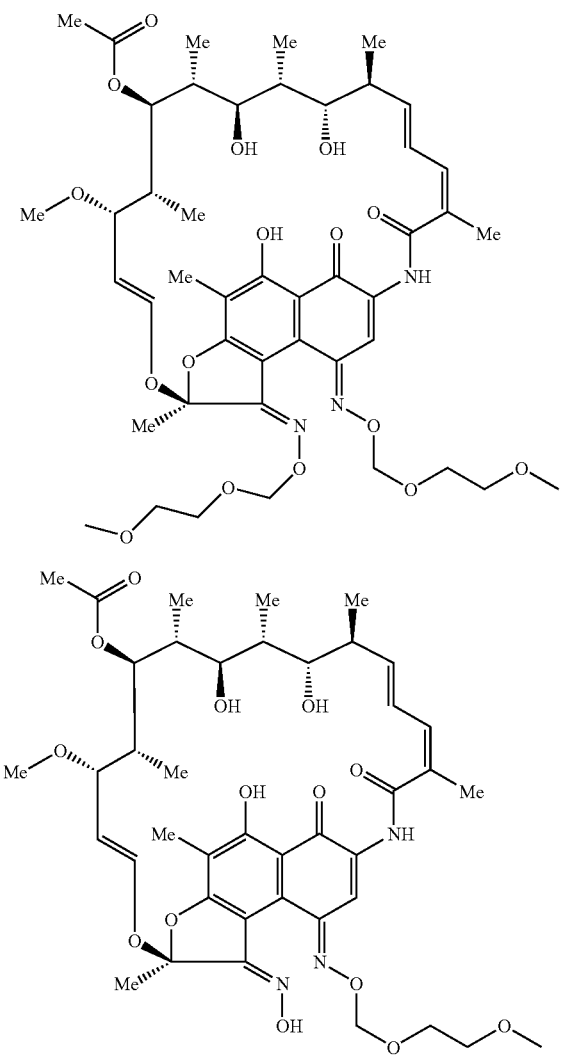

Synthesis: To a stirred solution of 4, 11-dideoxy-4, 11-dihydroxyiminorifamycin S (31.7 mg, 0.044 mmol) in acetonitrile (1.8 mL) was added sodium bicarbonate (28.0 mg, 0.33 mmol) and MEM chloride (6 μL, 0.096 mmol). The reaction mixture was allowed to stir for 1.5 hour at room temperature. The resultant solution was partitioned between ethyl acetate and water. The organic layer was separated, washed with brine, dried over sodium sulfate and concentrated in vacuo to dryness. The crude product was purified by preparative thin layer chromatography (8% MeOH/DCM) to give the a fast moving fraction A as an orange solid (28.0 mg, 71%) and a slower moving fraction B as an red solid (7.0 mg, 20%). A: ESI MS m/z 901.4 (M+H)$^+$; $^1$H NMR (400 MHz, CDCl$_3$) δ 13.16 (s, 1H), 8.68 (s, 1H), 8.47 (s, 1H), 6.45 (dd, J=10.4, 16.0 Hz, 1H), 6.25 (d, J=10.8 Hz, 1H), 6.10-6.05 (m, 2H), 5.71 (d, $J_{AB}$=6.8 Hz, 1H), 5.47 (d, $J_{AB}$=6.8 Hz, 1H), 5.36 (d, $J_{AB}$=6.8 Hz, 1H), 5.30 (d, $J_{AB}$=6.8 Hz, 1H), 5.12 (dd, J=6.8, 12.4 Hz, 1H), 4.81 (d, J=10.0 Hz, 1H), 3.89-3.76 (m, 5H), 3.69 (d, J=9.6 Hz, 1H), 3.64 (s, 1H), 3.64-3.54 (m, 4H), 3.43 (dd, J=2.0, 6.8 Hz, 1H), 3.40 (s, 3H), 3.37 (s, 3H), 3.12 (s, 3H), 3.00 (dd, J=4.0, 10.4 Hz, 1H), 2.40-2.35 (m, 1H), 2.23 (s, 3H), 2.06 (s, 3H), 2.05 (s, 3H), 2.03 (s, 3H), 1.84-1.76 (m, 2H), 1.63-1.58 (m, 1H), 1.03 (d, J=7.2 Hz, 3H), 0.86 (d, J=6.8 Hz, 3H), 0.67 (d, J=6.8 Hz, 3H), 0.13 (d, J=6.8 Hz, 3H). B: ESI MS m/z 814.3 (M+H)$^+$; $^1$H NMR (400 MHz, CDCl$_3$) δ 13.26 (s, 1H), 8.75 (s, 1H), 8.57 (s, 1H), 6.44 (dd, J=10.4, 16.0 Hz, 1H), 6.27 (d, J=10.4 Hz, 1H), 6.19 (d, J=12.4 Hz, 1H), 6.04 (dd, J=6.4, 16.0 Hz, 1H), 5.43 (d, $J_{AB}$=7.2 Hz, 1H), 5.41 (d, $J_{AB}$=7.2 Hz, 1H), 5.15 (dd, J=7.6, 12.4 Hz, 1H), 4.71 (d, J=10.4 Hz, 1H), 4.04-3.95 (m, 2H), 3.74-3.71 (m, 3H), 3.67-3.65 (m, 2H), 3.59-3.56 (m, 2H), 3.41 (s, 3H), 3.12 (s, 3H), 3.00 (d, J=10.0 Hz, 1H), 2.41-2.36 (m, 1H), 2.26 (s, 3H), 2.09 (s, 3H), 2.06 (s, 3H), 2.05 (s, 3H), 1.89-1.85 (m, 1H), 1.81-1.77 (m, 1H), 1.58-1.53 (m, 1H), 1.03 (d, J=6.8 Hz, 3H), 0.86 (d, J=6.8 Hz, 3H), 0.66 (d, J=6.8 Hz, 3H), 0.15 (d, J=6.8 Hz, 3H).

EXAMPLE 7

11-Deoxy-11-hydroxyiminorifamycin S

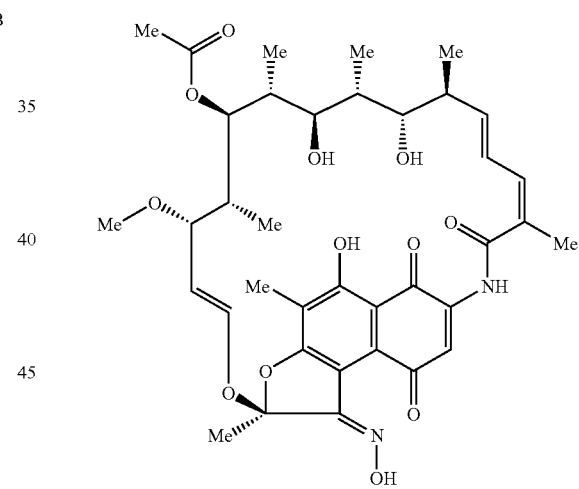

Synthesis: To a stirred solution of 4, 11-dideoxy-4, 11-dihydroxyiminorifamycin S (2.25 g, 3.10 mmol) in MeOH (60 mL) and THF (60 mL) co-solvent was first added the a solution of ammonium acetate (11.5 g, 149 mmol) in water (44 mL), then added the solution of tin dichloride dihydrate (1.55 g, 6.86 mmol) in 6 N HCl (12.0 mL) solution. The reaction mixture was allowed to stir overnight at room temperature. The resultant solution was partitioned between ethyl acetate and water. The organic layer was separated, dried over sodium sulfate, concentrated in vacuo to dryness. The title compound was afforeded produced as a purple solid (2.20 g, quantitative yield), which was subjected to further derivatization without purification. Analytical sample was purified by silica gel column chromatography. ESI MS m/z 711.2 (M+H)$^+$; $^1$H NMR (400 MHz, CDCl$_3$) δ 13.10 (s, 1H), 8.63 (s, 1H), 7.92 (s, 1H), 6.39-6.27 (m, 3H), 5.96 (dd, J=7.6, 15.2 Hz, 1H), 5.16 (dd, J=8.0, 13.2 Hz, 1H), 4.55 (d, J=9.2 Hz, 1H), 3.70 (br s, 1H), 3.61 (br s, 1H), 3.57 (d, J=9.2 Hz, 1H), 3.33 (dd, J=2.8, 8.2 Hz, 1H), 3.13 (s, 3H), 2.99 (c, J=10.0 Hz, 1 H), 2.42-2.35 (m, 1H), 2.31 (s, 3H), 2.08 (s, 3H), 2.07 (s, 3H), 2.04 (s, 3H), 2.04-2.00 (m, 1H), 1.82-1.76 (m, 1H), 1.50-1.44 (m, 1H), 1.03 (d, J=7.2 Hz, 3H), 0.85 (d, J=7.2 Hz, 3H), 0.67 (c, J=7.2 Hz, 3H), 0.19 (d, J=6.4 Hz, 3H).

EXAMPLE 8

11-Deoxy-11-(4-pyridylcarboxy)iminorifamycin S

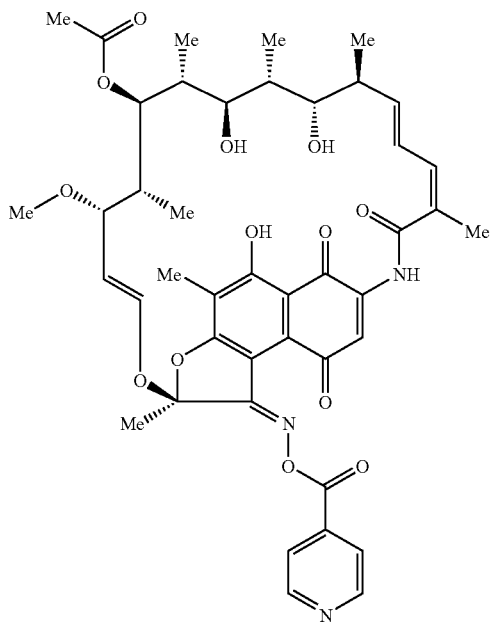

Synthesis: To a stirred solution of 11-deoxy-11-hydroxy-iminorifamycin S (41.8 mg, 0.06 mmol) in DCM (0.8 mL) was added pyridine (25 μL, 0.31 mmol) and isonicotinoyl chloride hydrochloride (20 mg, 0.11 mmol). The reaction solution was allowed to stir for 15 min at room temperature and then partitioned between ethyl acetate and water. The organic layer was separated, washed with water, dried over sodium sulfate and concentrated in vacuo to dryness. The title compound was afforded produced as a purple solid (40.0 mg, 83%). ESI MS m/z 816.2 (M+H)$^+$; $^1$H NMR (400 MHz, CDCl$_3$) δ 12.69 (s, 1H), 8.89 (br s, 2H), 8.38 (s, 1H), 8.00-7.98 (m, 2H), 7.85 (s, 1H), 6.37 (dd, J=10.0, 15.6 Hz, 1H), 6.27 (d, J=10.0 Hz, 1H), 6.16 (d, J=12.4 Hz, 1H), 5.99 (dd, J=6.8, 15.6 Hz, 1H), 5.20 (dd, J=7.2, 12.4 Hz, 1H), 4.72 (d, J=10.4 Hz, 1H), 3.64-3.58 (m, 3H), 3.37 (dd, J=2.8, 7.6 Hz, 1H), 3.11 (s, 3H), 2.99 (dd, J=3.6, 10.0 Hz, 1H), 2.40-2.33 (m, 1H), 2.30 (s, 3H), 2.05 (s, 3H), 2.04 (s, 3H), 2.02 (s, 3H), 1.97-1.89 (m, 1H), 1.78-1.72 (m, 1H), 1.59-1.53 (m, 1H), 1.01 (d, J=7.2 Hz, 3H), 0.84 (d, J=6.8 Hz, 3H), 0.66 (d, J=7.2 Hz, 3H), 0.23 (d, J=7.2 Hz, 3H).

EXAMPLE 9

11-Deoxy-11-acetoxyiminorifamycin S

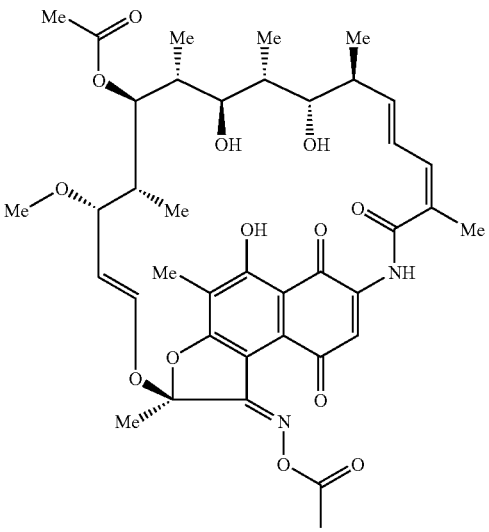

Synthesis: The title compound was prepared by following the same procedure as described for the preparation of Example 8 except acetic anhydride was used in place of isonicotinoyl chloride hydrochloride. The title compound was obtained as a purple solid. ESI MS m/z 753.1 (M+H)$^+$; $^1$H NMR (400 MHz, CDCl$_3$) δ 12.70 (s, 1H), 8.40 (s, 1H), 7.82 (s, 1H), 6.38 (dd, J=10.0, 15.6 Hz, 1H), 6.27 (d, J=10.0 Hz, 1H), 6.14 (d, J=12.4 Hz, 1H), 5.99 (dd, J=6.8, 15.6 Hz, 1H), 5.13 (dd, J=8.0, 12.4 Hz, 1H), 4.70 (d, J=10.4 Hz, 1H), 3.64 (d, J=6.8 Hz, 1H), 3.63 (s, 1H), 3.60 (d, J=9.6 Hz, 1H0, 3.39 (dd, J=2.4, 8.0 Hz, 1H), 3.12 (s, 3H), 3.00 (ddd, J=1.6, 4.8, 8.8 Hz, 1H), 2.44 (s, 3H), 2.40-2.34 (m, 1H), 2.29 (s, 3H), 2.06 (s, 3H), 2.04 (s, 3H), 2.02 (s, 3H), 1.97-1.92 (m, 1H), 1.80-1.75 (m, 1H), 1.59-1.53 (m, 1H), 1.02 (d, J=7.2 Hz, 3H), 0.86 (d, J=7.2 Hz, 3H), 0.68 (c, J=6.4 Hz, 3H), 0.25 (d, J=6.8 Hz, 3H).

EXAMPLE 10

11-Deoxy-11-methoxyethoxymethoxyiminorifamycin S

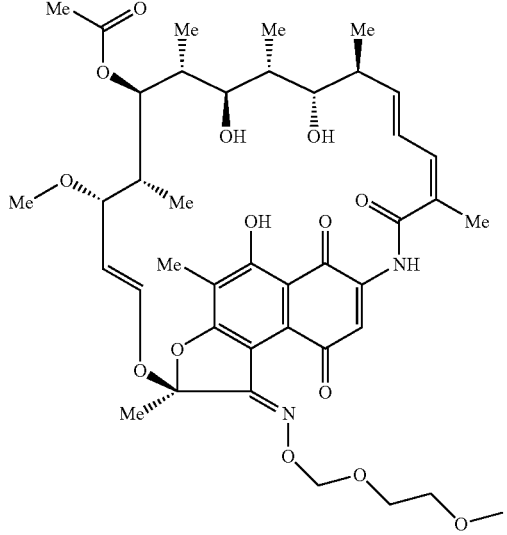

Synthesis: To a stirred solution of 11-deoxy-11-hydroxy-iminorifamycin S (5.0 mg, 0.007 mmol) in acetonitrile (0.3 mL) was added potassium carbonate (4.2 mg, 0.03 mmol) and MEM chloride (4 μL, 0.009 mmol). The reaction solution was allowed to stir for 30 minutes at room temperature and then partitioned between ethyl acetate and water. The organic layer was separated, washed with brine, dried over sodium sulfate and concentrated in vacuo to dryness. The crude product was purified by preparative thin layer chromatography (10% MeOH/DCM) to give the title compound as an orange solid (2.5 mg, 45%). ESI MS m/z 799.2 (M+H)$^+$; $^1$H NMR (400 MHz, CDCl$_3$) δ 12.76 (s, 1H), 8.48 (s, 1H), 7.78 (s, 1H), 6.41 (dd, J=10.0, 15.6 Hz, 1H), 6.29 (d, J=10.8 Hz, 1H), 6.23 (d, J=12.4 Hz, 1H), 5.99 (dd, J=6.4, 15.6 Hz, 1H), 5.50 (s, 2H), 5.16 (dd, J=7.6, 12.4 Hz, 1H), 4.64 (d, J=9.6 Hz, 1H), 4.09-4.07 (m, 2H), 3.70-3.59 (m, 4H), 3.41 (s, 3H), 3.41-3.39 (m, 1H), 3.13 (s, 3H), 3.13-3.11 (m, 1H), 3.00 (d, J=10.4 Hz, 1H), 2.40-2.33 (m, 1H), 2.28 (s, 3H), 2.05 (s, 3H), 2.04 (s, 3H), 2.01 (s, 3H), 2.01-1.96 (m, 1H), 1.78-1.72 (m, 1H), 1.59-1.53 (m, 1H), 1.03 (d, J=6.8 Hz, 3H), 0.85 (d, J=6.8 Hz, 3H), 0.68 (d, J=6.4 Hz, 3H), 0.24 (d, J=6.8 Hz, 3H).

EXAMPLE 11

11-Deoxy-11-allyloxyiminorifamycin S

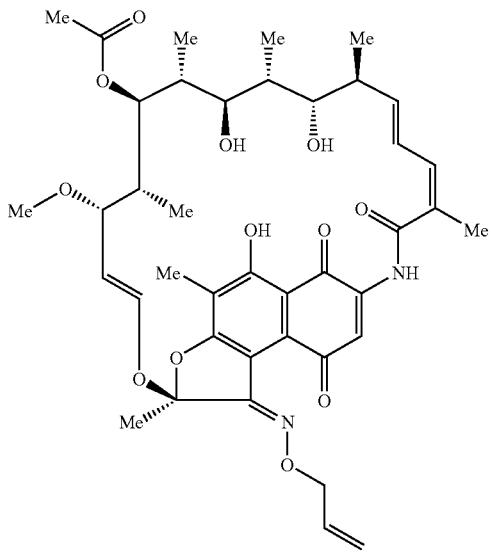

Synthesis: To a stirred mixture solution of 11-deoxy-11-hydroxyiminorifamycin S (534 mg, 0.75 mmol), sodium bicarbonate (270 mg, 3.2 mmol) and sodium iodide (222 mg, 1.48 mmol) in DMF (2.0 mL) and acetonitrile (2.0 mL) was added allylbromide (0.12 mL, 1.42 mmol) at room temperature. The reaction mixture was allowed to stir overnight at 72° C., then was cooled and partitioned between ethyl acetate and water. The organic layer was separated, dried over sodium sulfate and concentrated in vacuo to dryness. The crude product was purified by silica gel column chromatography (1.5% MeOH/DCM) to give the title compound as an orange solid (300 mg, 53%). ESI MS m/z 751.2 (M+H)$^+$; $^1$H NMR (400 MHz, CDCl$_3$) δ 12.76 (s, 1H), 8.45 (s, 1H), 7.80 (s, 1H), 6.41 (dd, J=10.0, 15.2 Hz, 1H), 6.28 (d, J=9.6 Hz, 1H), 6.16-6.10 (m, 2H), 5.99 (dd, J=6.8, 15.6 Hz, 1H), 5.44 (dd, J=1.6, 17.2 Hz, 1H), 5.30 (dd, J=1.2, 10.8 Hz, 1H), 5.10 (dd, J=7.6, 12.4 Hz, 1H), 4.87 (dd, J=1.6, 6.0 Hz, 2H), 4.65 (d, J=10.4 Hz, 1H), 3.62 (br s, 1H), 3.61 (c, J=10.0 Hz, 1H), 3.38 (dd, J=2.4, 7.6 Hz, 1H), 3.12 (s, 1H), 3.10 (d, J=8.0 Hz, 1H), 2.98 (dd, J=1.6, 10.0 Hz, 1H), 2.39-2.33 (m, 1H), 2.26 (s, 3H), 2.05 (s, 3H), 2.04 (s, 3H), 1.99 (s, 3H), 1.98-1.94 (m, 1H), 1.80-1.76 (m, 1H), 1.58-1.52 (m, 1H), 1.02 (d, J=7.2 Hz, 3H), 0.85 (d, J=7.2 Hz, 3H), 0.67 (d, J=6.8 Hz, 3H), 0.24 (d, J=6.8 Hz, 3H).

EXAMPLE 12

11-Deoxy-11-(2-bromoethoxyimino)rifamycin S

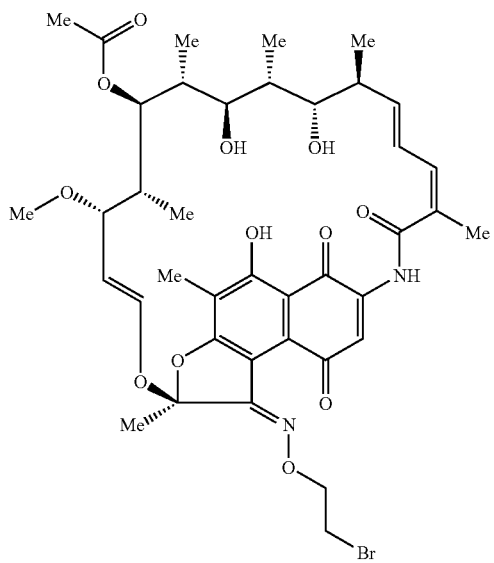

Synthesis: To a stirred solution of 11-deoxy-11-hydroxyimino-rifamycin S (239 mg, 0.34 mmol) in DMF (5.4 mL) was added TEA (0.32 mL, 2.30 mmol) and 1,2-dibromoethane (1.6 mL, 18.6 mmol) at room temperature. The reaction mixture was heated overnight). The reaction solution was allowed to stir overnight at 65° C. The resultant solution was cooled and partitioned between ethyl acetate and water. The organic layer was separated, dried over sodium sulfate, concentrated in vacuo to dryness. The crude product was purified by silica gel column chromatography (1.5% MeOH/DCM) to give the title compound as an orange solid (70 mg, 25%). %) and starting material as a purple solid (60 mg). ESI MS m/z 817.1 (M+H)$^+$; $^1$H NMR (400 MHz, CDCl$_3$) δ 12.77 (s, 1H), 8.48 (s, 1H), 7.80 (s, 1H), 6.43-6.27 (m, 3H), 5.97 (dd, J=2.8, 15.6 Hz, 1H), 5.16 (dd, J=8.0, 12.4 Hz, 1H), 4.71-4.60 (m, 3H), 3.96-3.90 (m, 1H), 3.82-3.77 (m, 1H), 3.70 (br s, 1H), 3.65 (br s, 1H), 3.61 (d, J=10.0 Hz, 1H), 3.42 (dd, J=2.4, 8.0 Hz, 1H), 3.13 (s, 1H), 2.99 (d, J=10.0 Hz, 1H), 2.39-2.34 (m, 1H), 2.28 (s, 3H), 2.05 (s, 3H), 2.04 (s, 3H), 2.01 (s, 3H), 2.03-1.98 (m, 1H), 1.82-1.76 (m, 1H), 1.58-1.51 (m, 1H), 1.03 (d, J=7.2 Hz, 3H), 0.85 (d, J=7.2 Hz, 3H), 0.68 (d, J=6.8 Hz, 3H), 0.26 (d, J=7.2 Hz, 3H).

EXAMPLE 13

(R/,S)-11-Deoxy-11-[{-{2-[4-(3-carboxy-1-cyclopropyl-6-fluoro-8-methoxy-4-oxo-1,4-dihydroquinolin-7-yl)-2-methylpiperazin-1-yl]ethoxyimino]}rifamycin S

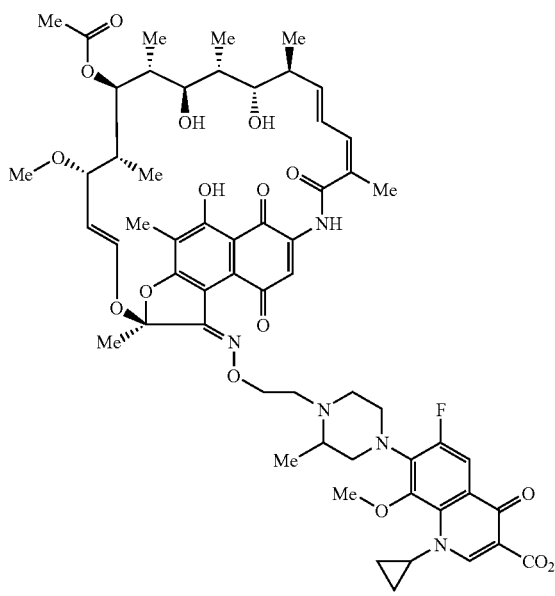

Synthesis: To a stirred solution of 11-deoxy-11-(2-bromo)ethoxy)iminorifamycin S (5.0 mg, 0.006 mmol) and (R/S)-1-Cyclopropylcyclopropyl-6-fluoro-8-methoxy-7-(3-methyl-piperazin-1-yl)-4-oxo-1,4-dihydro-quinoline-3-carboxylic acid (gatifloxacin, 12.2 mg, 0.032 mmol) in N,N-dimethylformamide (0.4 mL) was added triethylamine (10 μL, 0.072 mmol) at room temperature. The reaction solution mixture was allowed to stir overnight at 55° C. The resultant solution was partitioned between ethyl acetate and water. The organic layer was separated, dried over sodium sulfate, concentrated in vacuo to dryness. The crude product was purified by preparative thin layer chromatography (10% MeOH/CH$_2$Cl$_2$) to give the title compound as an orange solid (2.8 mg, 41%). ESI MS m/z 1112.4 (M+H)$^+$; $^1$H NMR (400 MHz, CDCl$_3$) δ 12.77 (s, 1H), 8.83 (s, 1H), 8.48 (s, 1H), 7.87 (d, J=12.4 Hz, 1H), 7.78 (s, 1H), 6.41 (dd, J=10.8, 15.6 Hz, 1H), 6.29 (d, J=10.8 Hz, 1H), 6.23 (d, J=12.0 Hz, 1H), 5.98 (dd, J=6.4, 15.2 Hz, 1H), 5.15 (dd, J=8.0, 12.0 Hz, 1H), 4.64 (d, J=9.6 Hz, 1H), 4.55-4.50 (m, 2H), 4.06-4.00 (m, 2H), 3.77 (s, 3H), 3.66-3.58 (m, 3H), 3.50-3.28 (m, 5H), 3.14 (s, 3H), 3.14-3.06 (m, 1H), 3.02-2.72 (m, 3H), 2.41-2.35 (m, 1H), 2.28 (s, 3H), 2.05 (s, 3H), 2.04 (s, 3H), 2.01 (s, 3H), 1.80-1.76 (m, 1H), 1.56-1.50 (m, 1H), 1.25-1.20 (m, 7H), 1.03 (d, J=6.8 Hz, 3H), 0.84 (d, J=7.2 Hz, 3H), 0.68 (d, J=6.4 Hz, 3H), 0.26 (c, J=7.2 Hz, 3H).

EXAMPLE 15

11-Deoxy-11-[{-{2-[4-(3-carboxy-1-cyclopropylcyclopropyl-6-fluoro-4-oxo-1,4-dihydroquinolin-7-yl)piperazin-1-yl]ethoxyimino]}rifamycin S

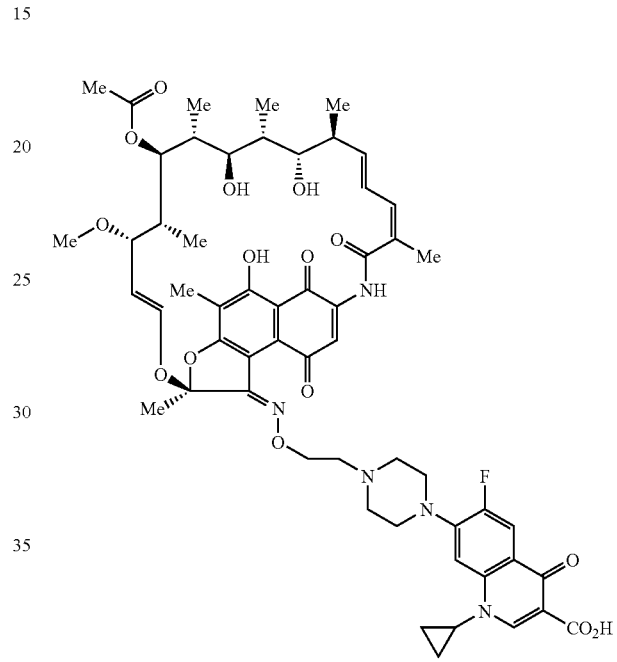

Synthesis: The title compound was prepared by following the same procedure as described for the preparation of Example 13 except 1-cyclopropyl-6-fluoro-4-oxo-7-piperazin-1-yl-1,4-dihydroquinoline-3-carboxylic acid (ciprofloxacin) was used in place of (R/S)-1-cCyclopropyl-6-fluoro-8-methoxy-7-(3-methyl-piperazin-1-yl)-4-oxo-1,4-dihydro-quinoline-3-carboxylic acid (gatifloxacin). ESI MS m/z 1068.5 (M+H)$^+$; $^1$H NMR (400 MHz, CDCl$_3$) δ 15.04 (s, 1H), 12.76 (s, 1H), 8.79 (s, 1H), 8.49 (s, 1H), 8.05 (d, J=13.2 Hz, 1H), 7.79 (s, 1H), 7.37 (d, J=6.4 Hz, 1H), 6.40 (dd, J=10.8, 14.8 Hz, 1H), 6.30 (d, J=10.2 Hz, 1H), 6.23 (d, J=12.4 Hz, 1H), 5.98 (dd, J=6.0, 15.6 Hz, 1H), 5.15 (dd, J=8.0, 12.8 Hz, 1H), 4.63 (d, J=10.8 Hz, 1H), 4.57 (br s, 2H), 4.06-4.00 (m, 2H), 3.67-3.56 (m, 4H), 3.40-3.36 (m, 5H), 3.13 (s, 3H), 3.02-2.98 (m, 2H), 2.86-2.80 (m, 4H), 2.41-2.35 (m, 1H), 2.28 (s, 3H), 2.05 (s, 3H), 2.04 (s, 3H), 2.01 (s, 3H), 1.80-1.74 (m, 2H), 1.56-1.50 (m, 1H), 1.42-1.38 (m, 2H), 1.23-1.19 (m, 2H), 1.03 (d, J=6.8 Hz, 3H), 0.84 (d, J=6.8 Hz, 3H), 0.68 (d, J=6.8 Hz, 3H), 0.26 (d, J=6.8 Hz, 3H).

EXAMPLE 15

11-Deoxy-11-[{-{2-[6-(3-carboxy-1-cyclopropylcy-clopropyl-6-fluoro-8-methoxy-4-oxo-1,4-dihydro-quinolin-7-yl)octahydro-pyrrolo[3,4-b]pyridin-1-yl]ethoxyimino]}rifamycin S

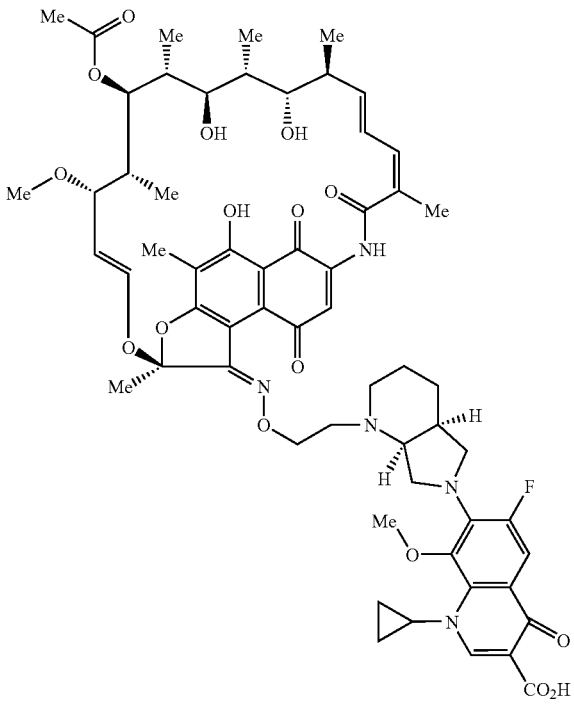

11-Deoxy-11-[{-{2-[6-(3-carboxy-1-cyclopropyl-6-fluoro-8-methoxy-4-oxo-1,4-dihydro-quinolin-7-yl)octahydro-pyrrolo[3,4-b]pyridin-1-yl]ethoxy}iminorifamycin S The title compound was prepared by following the same procedure as described for the preparation of example 11 except (±)1-cyclopropyl-6-fluoro-8-methoxy-7-(octahydro-6H-pyrrolo[3,4-b]pyridin-6-yl)-4-oxo-1,4-dihydro-quinoline-3-carboxylic acid (moxifloxacin) was used in place of (R/S)-1-cCyclopropyl-6-fluoro-8-methoxy-7-(3-methyl-piperazin-1-yl)-4-oxo-1,4-dihydro-quinoline-3-carboxylic acid (gatifloxacin). ESI MS m/z 1138.4 (M+H)$^+$; $^1$H NMR (400 MHz, CDCl$_3$) δ 15.00 (s, 1H), 12.75 (s, 1H), 8.66 (s, 1H), 8.38 (s, 1H), 7.49 (s, 1H), 7.38 (d, J=14.4 Hz, 1H), 6.37-6.25 (m, 3H), 6.06-6.00 (m, 2H), 5.08 (dd, J=2.8, 12.0 Hz, 1H), 4.70 (d, J=10.4 Hz, 1H), 4.47-4.41 (m, 1H), 4.38-4.32 (m, 1H), 4.00-3.91 (m, 2H), 3.82-3.72 (m, 2H), 3.68 (app d, J=4.4 Hz, 1H), 3.60-3.57 (m, 2H), 3.51 (s, 3H), 3.49-3.41 (m, 2H), 3.37 (dd, J=2.0, 6.8 Hz, 1H), 3.13-3.07 (m, 1H), 3.09 (s, 3H), 3.03-2.95 (m, 2H), 2.43-2.33 (m, 3H), 2.28 (s, 3H), 2.28-2.20 (m, 1H), 2.09 (s, 3H), 2.03 (s, 3H), 2.00 (s, 3H), 1.84-1.75 (m, 5H), 1.56-1.50 (m, 1H), 1.28-1.13 (m, 4H), 1.01 (d, J=6.8 Hz, 3H), 0.83 (d, J=7.6 Hz, 3H), 0.64 (d, J=6.8 Hz, 3H), 0.10 (d, J=6.8 Hz, 3H).

EXAMPLE 16

11-Deoxy-11-[{-{2-[4-{4-[5-(acetylamino-methyl)-2-oxo-oxazolidin-3-yl]-2-fluoro-phenyl}-piperazin-1-yl]ethoxyimino}]rifamycin S

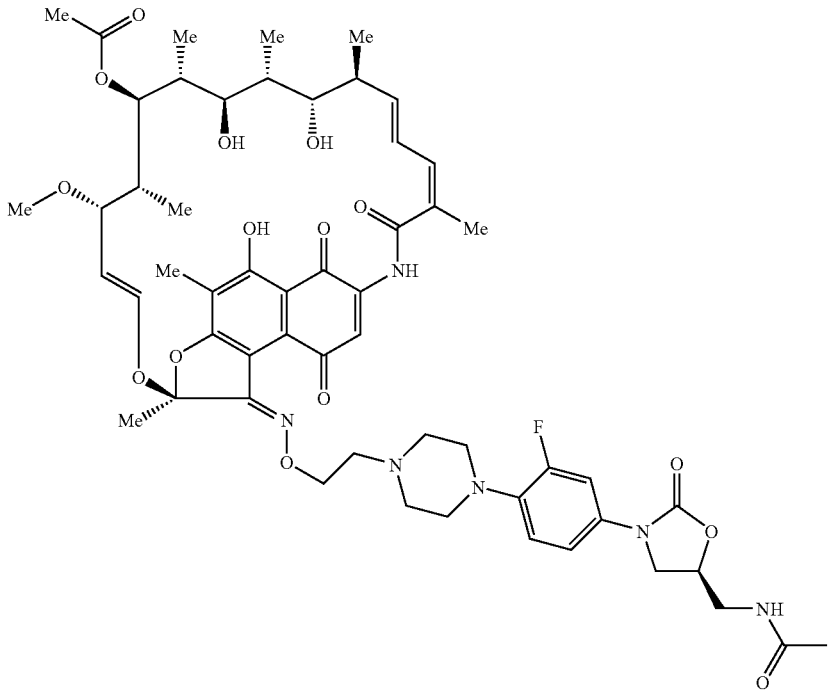

Synthesis: The title compound was prepared by following the same procedure as described for the preparation of Example 13 except (5S)-N-[3-(3-fluoro-4-piperazin-1-yl-phenyl)-2-oxo-oxazolidin-5-ylmethyl]-acetamide was used in place of (R/S)-1-Cyclopropyl-6-fluoro-8-methoxy-7-(3-methyl-piperazin-1-yl)-4-oxo-1,4-dihydro-quinoline-3-carboxylic acid (gatifloxacin). ESI MS m/z 1073.5 (M+H)+; $^1$H NMR (400 MHz, CDCl$_3$) δ 12.77 (s, 1H), 8.48 (s, 1H), 7.80 (s, 1H), 7.45 (d, J=14.0 Hz, 1H), 7.06 (d, J=2.4, 8.8 Hz, 1H), 6.94 (t, J=8.8 Hz, 1H), 6.41 (dd, J=10.4, 16.0 Hz, 1H), 6.29 (d, J=10.4 Hz, 1H), 6.25 (d, J=12.4 Hz, 1H), 6.02-5.96 (m, 2H), 5.14 (dd, J=8.0, 12.4 Hz, 1H), 4.80-4.75 (m, 1H), 4.64 (d, J=10.4 Hz, 1H), 4.58-4.54 (m, 2H), 4.02 (t, J=8.8 Hz, 1H), 3.76-3.56 (m, 6H), 3.50 (s, 3H), 3.41 (dd, J=2.0, 8.0 Hz, 1H), 3.12 (s, 3H), 3.12-3.08 (m, 4H), 2.99 (dd, J=4.8, 10.0 Hz, 1H), 2.82-2.74 (m, 4H), 2.42-2.34 (m, 1H), 2.27 (s, 3H), 2.06 (s, 3H), 2.03 (s, 3H), 2.00 (s, 3H), 2.02-1.96 (m, 1H), 1.81-1.75 (m, 1H), 1.58-1.52 (m, 1H), 1.03 (d, J=7.2 Hz, 3H), 0.85 (d, J=7.2 Hz, 3H), 0.68 (d, J=6.8 Hz, 3H), 0.25 (d, J=7.2 Hz, 3H).

EXAMPLE 17

11-Deoxy-11-{2-[4-pyridin-2-yl)piperazin-1-yl]ethoxyimino}rifamycin S

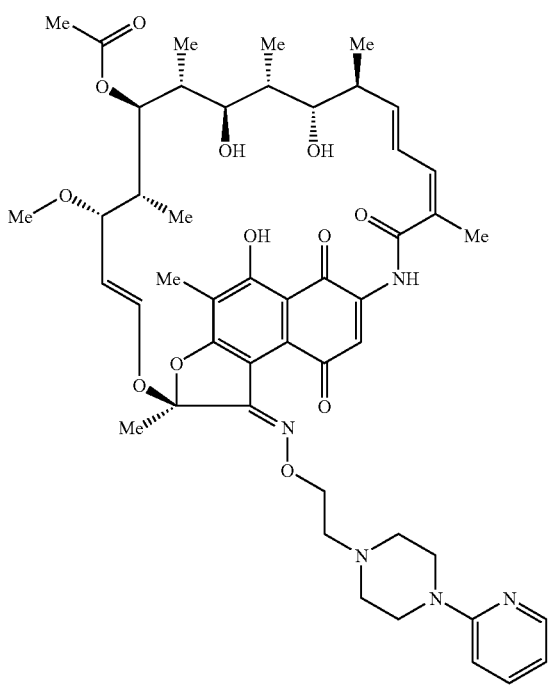

Synthesis: The title compound was prepared by following the same procedure as described for the preparation of Example 13 except 1-pyridin-2-yl-piperazine was used in place of (R/S)-1-cyclopropyl-6-fluoro-8-methoxy-7-(3-methyl-piperazin-1-yl)-4-oxo-1,4-dihydro-quinoline-3-carboxylic acid (gatifloxacin). ESI MS m/z 900.4 (M+H)+; $^1$H NMR (400 MHz, CDCl$_3$) δ 12.77 (s, 1H), 8.47 (s, 1H), 8.22-8.14 (m, 2H), 7.61 (s, 1H), 7.53-7.27 (m, 2H), 6.70-6.62 (m, 2H), 6.42 (dd, J=2.4, 15.6 Hz, 1H), 6.30-6.22 (m, 1H), 6.00 (dd, J=6.0, 15.6 Hz, 1H), 5.14 (dd, J=8.0, 12.0 Hz, 1H), 4.65 (d, J=10.4 Hz, 1H), 4.58-4.54 (m, 1H), 3.92-3.84 (m, 1H), 3.70-3.50 (m, 8H), 3.40 (dd, J=2.4, 8.0 Hz, 1H), 3.11 (s, 3H), 2.75-2.60 (m, 4H), 2.42-2.32 (m, 1H), 2.27 (s, 3H), 2.06 (s, 3H), 2.03 (s, 3H), 2.00 (s, 3H), 1.81-1.75 (m, 1H), 1.58-1.52 (m, 1H), 1.03 (d, J=6.8 Hz, 3H), 0.85 (c, J=6.8 Hz, 3H), 0.66 (d, J=7.2 Hz, 3H), 0.24 (c, J=7.2 Hz, 3H).

EXAMPLE 18

11-Deoxy-11-{2-[4-(3-trifluoromethyl-phenyl)-piperazin-1-yl]ethoxyimino}rifamycin S

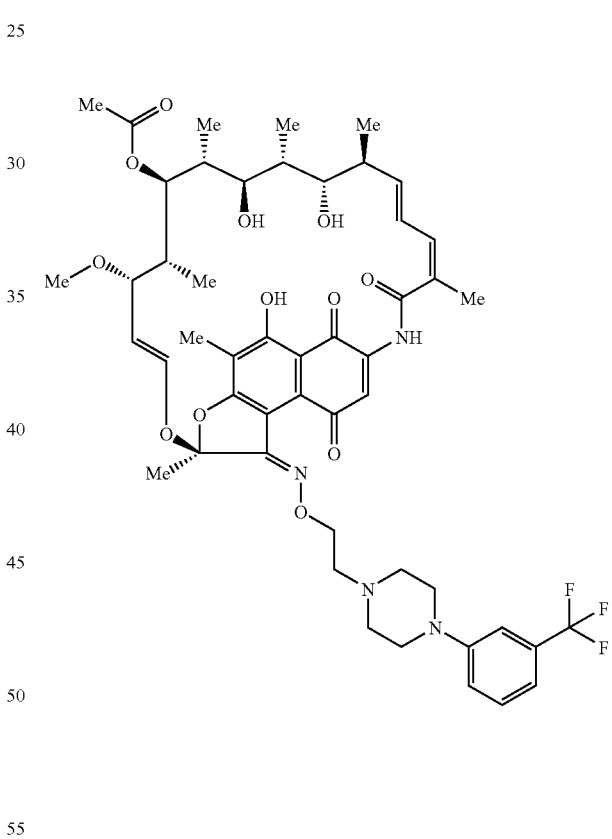

Synthesis: The title compound was prepared by following the same procedure as described for the preparation of Example 13 except 1-(3-trifluoromethylphenyl)phenyl-piperazine was used in place of (R/S)-1-cyclopropylcyclopropyl-6-fluoro-8-methoxy-7-(3-methyl-piperazin-1-yl)-4-oxo-1,4-dihydro-quinoline-3-carboxylic acid (gatifloxacin). ESI MS m/z 967.4 (M+H)+; $^1$H NMR (400 MHz, CDCl$_3$) δ 12.77 (s, 1H), 8.48 (s, 1H), 7.90 (s, 1H), 7.40-7.34 (m, 1H), 7.17-7.07 (m, 3H), 6.42 (dd, J=10.0, 15.6 Hz, 1H), 6.29 (d, J=10.4 Hz, 1H), 6.24 (d, J=12.4 Hz, 1H), 6.00 (dc, J=6.8, 15.6 Hz, 1H), 5.15 (dd, J=8.0, 12.0 Hz, 1H), 4.65 (d, J=10.0

Hz, 1H), 4.60-4.54 (m, 2H), 3.74 (app t, J=5.2 Hz, 1H), 3.67-3.61 (m, 2H), 3.56 (app t, J=5.2 Hz, 1H), 3.39 (d, J=5.6 Hz, 1H), 3.27-3.20 (m, 4H), 3.11 (s, 3H), 3.00-2.96 (m, 1H), 2.72-2.60 (m, 4H), 2.42-2.34 (m, 1H), 2.27 (s, 3H), 2.06 (s, 3H), 2.02 (s, 3H), 2.00 (s, 3H), 1.80-1.75 (m, 1H), 1.57-1.52 (m, 1H), 1.03 (d, J=7.2 Hz, 3H), 0.85 (d, J=6.8 Hz, 3H), 0.66 (d, J=6.8 Hz, 3H), 0.25 (d, J=6.8 Hz, 3H).

EXAMPLE 19

11-Deoxy-11-{2-[4-(isoquinoline-8-sulfonyl)-piperazin-1-yl]-ethoxyimino}rifamycin S

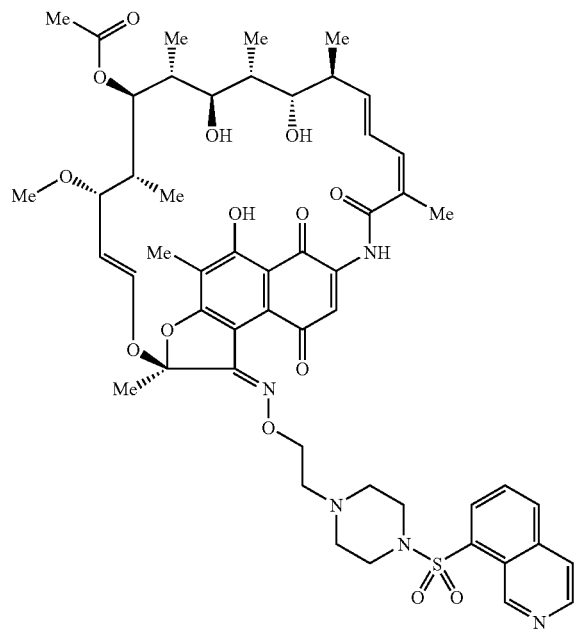

Synthesis: The title compound was prepared by following the same procedure as described for the preparation of Example 13 except 8-(piperazinepiperazine-1-sulfonyl)-isoquinoline was used in place of (R/S)-1-cyclopropyl-6-fluoro-8-methoxy-7-(3-methyl-piperazin-1-yl)-4-oxo-1,4-dihydro-quinoline-3-carboxylic acid (gatifloxacin). ESI MS m/z 1014.4 (M+H)$^+$; $^1$H NMR (400 MHz, CDCl$_3$) δ 12.75 (s, 1H), 9.36 (br s, 1H), 8.70 (br s, 1H), 8.52 (s, 1H), 8.47 (s, 1H), 8.39 (d, J=7.2 Hz, 1H), 8.24 (d, J=8.0 Hz, 1H), 8.03 (s, 1H), 7.76-7.72 (m, 2H), 6.40 (dd, J=10.4, 15.2 Hz, 1H), 6.29 (d, J=9.6 Hz, 1H), 6.12 (d, J=12.4 Hz, 1H), 5.99 (dd, J=6.4, 15.6 Hz, 1H), 5.07 (dd, J=8.0, 12.4 Hz, 1H), 4.62 (d, J=9.6 Hz, 1H), 4.41 (br s, 2H), 3.66-3.60 (m, 2H), 3.32-3.21 (m, 4H), 3.07 (s, 3H), 3.01-2.97 (m, 1H), 2.85-2.78 (m, 2H), 2.70-2.60 (m, 4H), 2.40-2.35 (m, 1H), 2.26 (s, 3H), 2.05 (s, 3H), 2.04 (s, 3H), 1.90 (s, 3H), 1.80-1.75 (m, 1H), 1.55-1.50 (m, 1H), 1.03 (d, J=6.8 Hz, 3H), 0.85 (d, J=6.8 Hz, 3H), 0.67 (d, J=6.8 Hz, 3H), 0.19 (d, J=6.8 Hz, 3H).

EXAMPLE 20

11-Deoxy-11-{2-[bis-(2-hydroxy-ethyl)-amino]ethoxyimino}rifamycin S

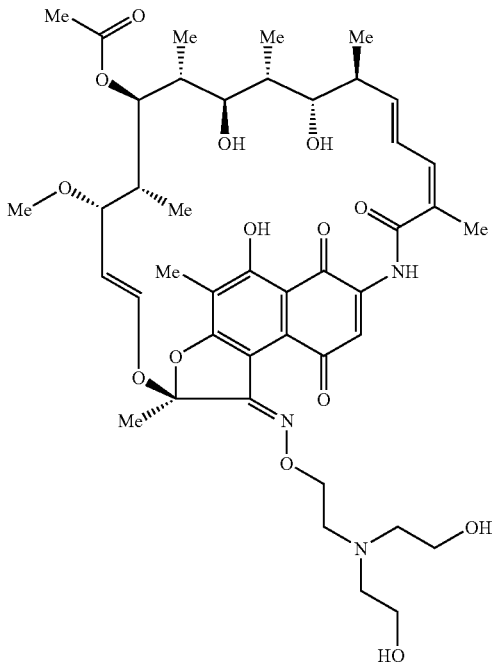

Synthesis: The title compound was prepared by following the same procedure as described for the preparation of Example 13 except 2-(2-hydroxyhydroxyethylamino)-ethanol was used in place of (R/S)-1-cyclopropylcyclopropyl-6-fluoro-8-methoxy-7-(3-methyl-piperazin-1-yl)-4-oxo-1,4-dihydro-quinoline-3-carboxylic acid (gatifloxacin). ESI MS m/z 842.4 (M+H)$^+$; $^1$H NMR (400 MHz, CDCl$_3$) δ 12.74 (s, 1H), 8.46 (s, 1H), 7.77 (s, 1H), 6.39 (dd, J=10.4, 15.6 Hz, 1H), 6.29 (d, J=10.4 Hz, 1H), 6.16 (d, J=12.8 Hz, 1H), 5.99 (dd, J=6.4, 15.2 Hz, 1H), 5.11 (dd, J=7.6, 12.4 Hz, 1H), 4.66 (d, J=9.6 Hz, 1H), 4.58-4.50 (m, 2H), 3.75 (br s, 4H), 3.68-3.60 (m, 4H), 3.42 (dd, J=2.4, 8.0 Hz, 1H), 3.20 (br s, 1H), 3.13 (s, 3H), 3.02-2.89 (m, 5H), 2.40-2.35 (m, 1H), 2.27 (s, 3H), 2.05 (s, 6H), 1.99 (s, 3H), 1.99-1.96 (m, 1H), 1.80-1.75 (m, 1H), 1.58-1.53 (m, 1H), 1.03 (d, J=7.2 Hz, 3H), 0.86 (d, J=7.2 Hz, 3H), 0.69 (c, J=6.8 Hz, 3H), 0.24 (d, J=7.2 Hz, 3H).

EXAMPLE 21

11-Deoxy-11-[2-(3,5-dimethyl-piperazin-1-yl)ethoxyimino]rifamycin S

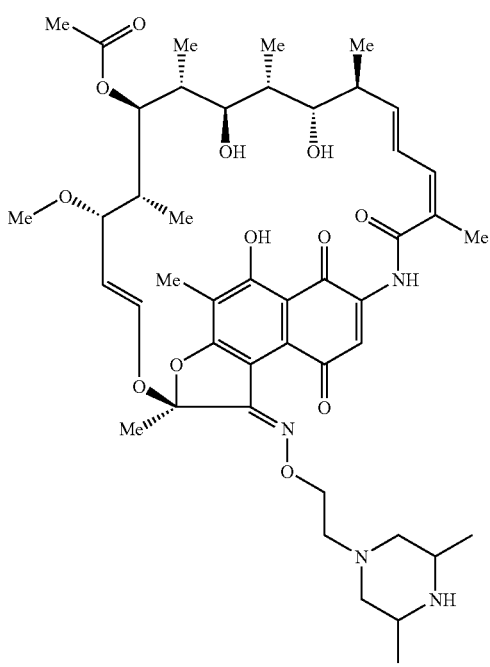

Synthesis: The title compound was prepared by following the same procedure as described for the preparation of Example 14 except 2,6-dimethyl-piperazine was used in place of (R/S)-1-cyclopropyl-6-fluoro-8-methoxy-7-(3-methyl-piperazin-1-yl)-4-oxo-1,4-dihydro-quinoline-3-carboxylic acid (gatifloxacin). ESI MS m/z 851.5 (M+H)$^+$; $^1$H NMR (400 MHz, CDCl$_3$) δ 12.74 (s, 1H), 8.48 (s, 1H), 7.77 (s, 1H), 6.41 (dd, J=10.4, 15.2 Hz, 1H), 6.29 (d, J=10.4 Hz, 1H), 6.17 (d, J=12.4 Hz, 1H), 6.00 (dd, J=6.4, 15.6 Hz, 1H), 5.12 (dd, J=7.6, 12.4 Hz, 1H), 4.66 (d, J=10.4 Hz, 1H), 4.58-4.48 (m, 2H), 3.68-3.62 (m, 3H), 3.42-3.26 (m, 5H), 3.14 (s, 3H), 3.02-2.88 (m, 5H), 2.55-2.35 (m, 4H), 2.28 (s, 3H), 2.06 (s, 6H), 1.97 (s, 3H), 1.99-1.96 (m, 1H), 1.80-1.75 (m, 1H), 1.58-1.52 (m, 1H), 1.03 (d, J=6.8 Hz, 3H), 0.85 (d, J=6.8 Hz, 3H), 0.69 (c, J=6.8 Hz, 3H), 0.23 (c, J=7.2 Hz, 3H).

EXAMPLE 22

11-Deoxy-11-[2-(4-methylpiperazin-1-yl)ethoxyimino]rifamycin S

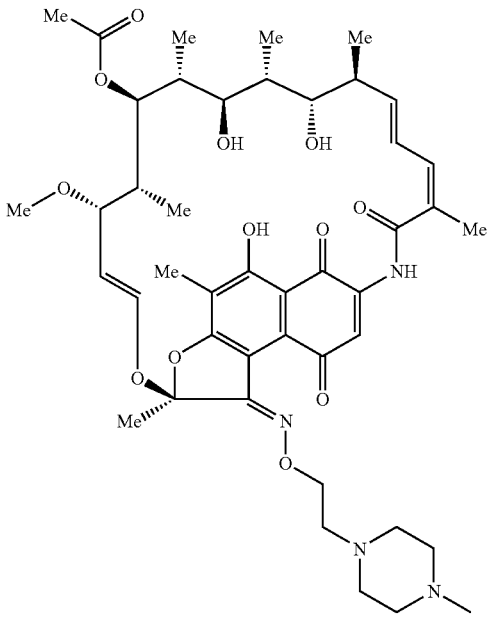

Synthesis: The title compound was prepared by following the same procedure as described for the preparation of Example 13 except 1-methylpiperazine was used in place of (R/S)-1-cyclopropyl-6-fluoro-8-methoxy-7-(3-methyl-piperazin-1-yl)-4-oxo-1,4-dihydro-quinoline-3-carboxylic acid (gatifloxacin). ESI MS m/z 837.5 (M+H)$^+$.

EXAMPLE 23

11-Deoxy-11-[2-(4-hydroxypiperadin-1-yl)ethoxyimino]rifamycin S

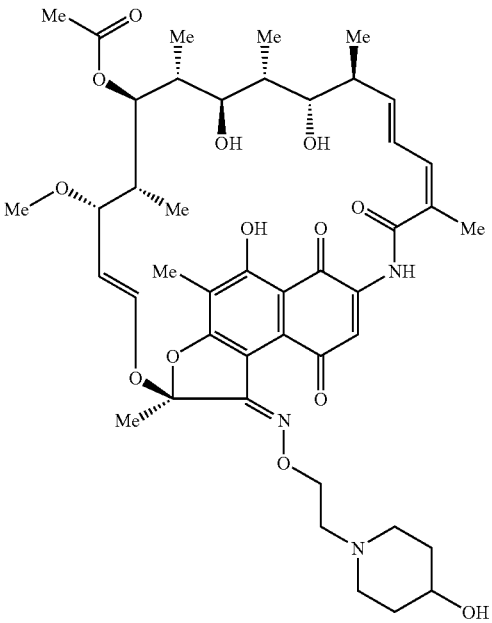

Synthesis: The title compound was prepared by following the same procedure as described for the preparation of Example 13 except 4-hydroxypiperadine was used in place of (R/S)-1-cyclopropyl-6-fluoro-8-methoxy-7-(3-methyl-piperazin-1-yl)-4-oxo-1,4-dihydro-quinoline-3-carboxylic acid (gatifloxacin). ESI MS m/z 838.5 (M+H)+.

EXAMPLE 24

11-Deoxy-11-[2-morpholin-4-yl)ethoxyimino]rifamycin S

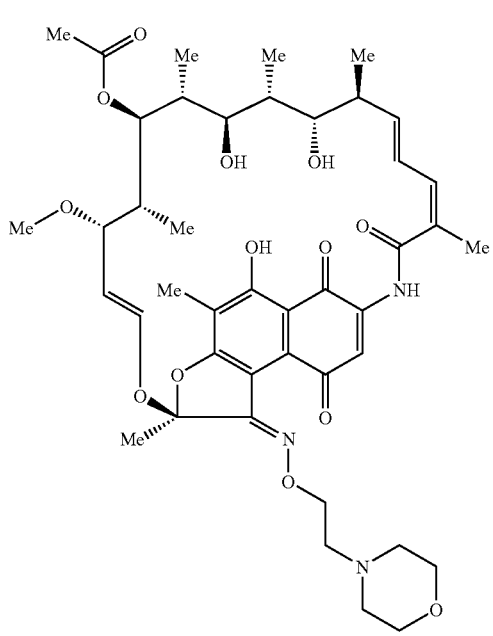

Synthesis: The title compound was prepared by following the same procedure as described for the preparation of Example 13 except morpholine was used in place of (R/S)-1-cyclopropylcyclopropyl-6-fluoro-8-methoxy-7-(3-methyl-piperazin-1-yl)-4 oxo-1,4-dihydro-quinoline-3-carboxylic acid (gatifloxacin). ESI MS m/z 824.4 (M+H)+; 1H NMR (400 MHz, CDCl3) δ 12.76 (s, 1H), 8.46 (s, 1H), 7.77 (s, 1H), 6.40 (dd, J=10.0, 15.6 Hz, 1H), 6.28 (d, J=10.0 Hz, 1H), 6.22 (d, J=12.4 Hz, 1H), 5.98 (dd, J=6.4, 15.6 Hz, 1H), 5.13 (dd, J=7.6, 15.6 Hz, 1H), 4.64 (d, J=10.8 Hz, 1H), 4.58-4.48 (m, 2H), 4.21 (br s, 1H), 3.74-3.60 (m, 7H), 3.39 (d, J=6.4 Hz, 1H), 3.13 (s, 3H), 2.88-2.80 (m, 1H), 2.64-2.50 (m, 4H), 2.40-2.32 (m, 1H), 2.26 (s, 3H), 2.04 (s, 6H), 1.97 (s, 3H), 1.99-1.96 (m, 1H), 1.80-1.74 (m, 1H), 1.58-1.52 (m, 1H), 1.02 (d, J=7.2 Hz, 3H), 0.84 (d, J=6.8 Hz, 3H), 0.67 (d, J=6.8 Hz, 3H), 0.23 (d, J=7.2 Hz, 3H).

EXAMPLE 25

11-Deoxy-11-[2-(4-benzylpiperazin-1-yl)ethoxy-imino]rifamycin S

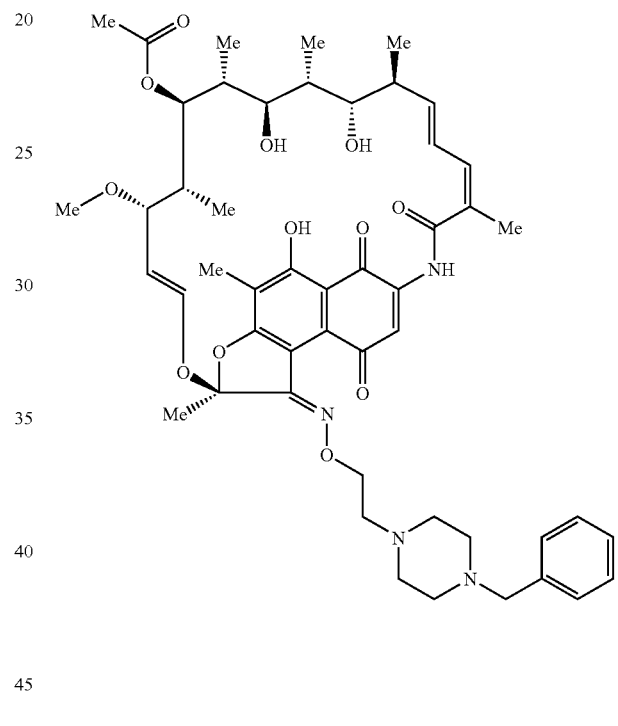

Synthesis: The title compound was prepared by following the same procedure as described for the preparation of Example 13 except 4-benzylpiperazine was used in place of (R/S)-1-cyclopropylcyclopropyl-6-fluoro-8-methoxy-7-(3-methyl-piperazin-1-yl)-4-oxo-1,4-dihydro-quinoline-3-carboxylic acid (gatifloxacin). ESI MS m/z 913.4 (M+H)+; 1H NMR (400 MHz, CDCl3) δ 12.76 (s, 1H), 8.74 (s, 1H), 7.78 (s, 1H), 7.32 (br s, 5H), 6.41 (dd, J=10.0, 15.2 Hz, 1H), 6.29 (d, J=10.0 Hz, 1H), 6.28-6.20 (m, 1H), 5.99 (dd, J=6.4, 15.2 Hz, 1H), 5.12-5.08 (m, 1H), 4.63 (d, J=10.0 Hz, 1H), 4.52-4.45 (m, 2H), 3.67-3.38 (m, 7H), 3.14 (s, 3H), 3.02-2.98 (m, 1H), 2.68-2.35 (m, 7H), 2.27 (s, 3H), 2.06 (s, 3H), 2.05 (s, 3H), 1.99-1.96 (m, 1H), 1.96 (s, 3H), 1.80-1.75 (m, 1H), 1.56-1.50 (m, 1H), 1.03 (d, J=7.2 Hz, 3H), 0.85 (d, J=6.8 Hz, 3H), 0.69 (d, J=6.8 Hz, 3H), 0.23 (d, J=7.2 Hz, 3H).

EXAMPLE 26

11-Deoxy-11-{2-[4-(2-hydroxy-phenyl)piperazin-1-yl]ethoxyimino}rifamycin S

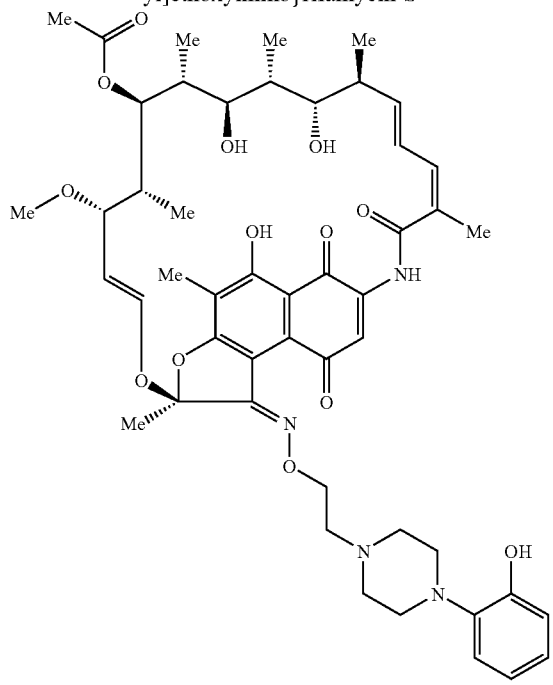

Synthesis: The title compound was prepared by following the same procedure as described for the preparation of Example 13 except 2-piperazin-1-yl-phenol was used in place of (R/S)-1-cyclopropylcyclopropyl-6-fluoro-8-methoxy-7-(3-methyl-piperazin-1-yl)-4-oxo-1,4-dihydro-quinoline-3-carboxylic acid (gatifloxacin). ESI MS m/z 915.5 (M+H)$^+$; $^1$H NMR (400 MHz, CDCl$_3$) δ 12.77 (s, 1H), 8.47 (s, 1H), 7.80 (s, 1H), 7.17-7.07 (m, 2H), 6.97-6.85 (m, 2H), 6.42 (dd, J=10.0, 15.6 Hz, 1H), 6.29 (d, J=10.0 Hz, 1H), 6.24 (d, J=12.8 Hz, 1H), 5.99 (dd, J=6.4, 15.6 Hz, 1H), 5.15 (dd, J=10.0, 12.4 Hz, 1H), 4.66 (d, J=10.4 Hz, 1H), 4.56 (br s, 2H), 3.70-3.58 (m, 4H), 3.42 (dd, J=2.4, 8.0 Hz, 1H), 3.15 (s, 3H), 3.01-2.75 (m,~10H), 2.41-2.35 (m, 1H), 2.28 (s, 3H), 2.06 (s, 3H), 2.03 (s, 3H), 2.00 (s, 3H), 2.00-1.95 (m, 1H), 1.80-1.75 (m, 1H), 1.58-1.52 (m, 1H), 1.03 (d, J=6.8 Hz, 3H), 0.85 (d, J=6.8 Hz, 3H), 0.69 (d, J=7.2 Hz, 3H), 0.25 (d, J=6.8 Hz, 3H).

EXAMPLE 27

11-Deoxy-3-hydroxymethyl-11-(4-carboxymethoxy-imino)-rifamycin S

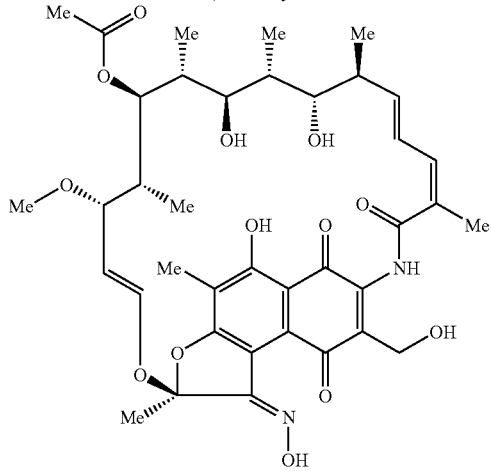

Synthesis: Step 1. 11-Deoxy-3-hydroxymethyl-rifamycin S To a stirred solution of 3-formyl rifamycin SV (910 mg, 1.25 mmol) in THF (5.0 mL) and water (1.0 mL) was added sodium cyanoborohydride (380 mg, 6.05 mmol) in four portions during a period of 30 min at 0° C. The reaction solution was partitioned between ethyl acetate and water. The organic layer was washed with 5% solution of potassoum ferrocyanide in potassium phosphate buffer (PH=7.4), water and brine successivly. The organic layer was then separated, dried over sodium sulfate and concentrated vacuo to give the title compound as a brown solid (473 mg, 65%). ESI MS m/z 748.3 (M+Na)$^+$.

Step 2. 11-Deoxy-3-hydroxymethyl-11-(4-carboxymethoxyimino)-rifamycin S To a stirred solution of 3-hydroxymethyl-rifamycin S (48.0 mg, 0.066 mmol) in methanol (1.0 mL) was added pyridine (25 μL, 0.31 mmol) and hydroxylamine hydrochloride (21.5 mg, 0.31 mmol). The reaction solution was allowed to stir for 1.5 hour at room temperature. The reaction mixture was concentrated and the residue was purified by preparative thin layer chromatography (8% MeOH/DCM) to give the title compound as a red solid (10.0 mg, 20%). ESI MS m/z 741.1 (M+H)$^+$; $^1$H NMR (400 MHz, CDCl$_3$) δ 13.44 (s, 1H), 8.70 (br s, 1H), 7.37 (br s, 1H), 7.08-7.02 (m, 1H), 6.47 (d, J=10.8 Hz, 1H), 6.17-6.11 (m, 3H), 5.90 (d J=12.8 Hz, 1H), 5.28 (dd, J=5.2, 12.0 Hz, 1H), 5.00 (d, J=9.6 Hz, 1H), 4.74 (d, J=12.8 Hz, 1H), 3.97 (d, J=4.0 Hz, 1H), 3.82 (d, J=8.4 Hz, 1H), 3.58-3.50 (m, 1H), 3.40 (s, 1H), 3.12 (s, 3H), 2.99 (dd, J=2.8, 10.0 Hz, 1H), 2.45-2.36 (m, 1H), 2.24 (s, 3H), 2.07 (s, 3H), 2.05 (s, 3H), 2.01 (s, 3H), 1.88-1.72 (m, 3H), 1.02 (d, J=7.2 Hz, 3H), 0.92 (d, J=7.2 Hz, 3H), 0.70 (d, J=7.2 Hz, 3H), 0.39 (d, J=7.2 Hz, 3H).

EXAMPLE 28

11-Deoxy-3-(morpholin-4-yl)-11-(4-carboxymethoxyimino)-rifamycin S

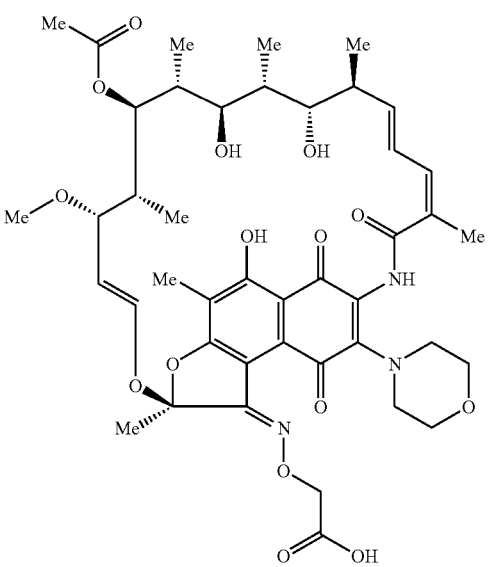

Synthesis: To a stirred solution of 3-(morpholinmorpholin-4-yl)-rifamycin S (44.0 mg, 0.056 mmol) (3-(morpholinmorpholin-4-yl)-rifamycin S can be synthesized by methods disclosed in Chem. Pharm. Bull., 33:1982, 1985) in MeOH (1.0 mL) was added pyridine (25 µL, 0.31 mmol) and carboxymethoxylamine hydrochloride (37.5 mg, 0.17 mmol). The reaction solution was allowed to stir overnight at room temperature. The reaction mixture was concentrated in vacuo and the residue was purified by preparative thin layer chromatography (10% MeOH/DCM) to give the title compound as a purple solid (24.0 mg, 50%). ESI MS m/z 854.1 (M+H)$^+$; $^1$H NMR (400 MHz, CDCl$_3$) δ 13.19 (s, 1H), 7.60 (s, 1H), 7.08-7.02 (m, 1H), 6.34 (d, J=10.8 Hz, 1H), 6.15-6.10 (m, 2H), 5.28 (dd, J=8.0, 12.4 Hz, 1H), 5.11 (d, J=10.0 Hz, 1H), 4.85 (d, J$_{AB}$=16.0 Hz, 1H), 4.73 (d, J$_{AB}$=16.0 Hz, 1H), 3.95-3.87 (m, 4H), 3.78-3.72 (m, 2H), 3.50-3.45 (m, 3H), 3.34-3.28 (m, 2H), 3.12 (s, 3H), 3.06 (d, J=9.6 Hz, 1H), 2.40-2.35 (m, 1H), 2.23 (s, 3H), 2.05 (s, 3H), 1.95 (s, 3H), 1.92 (s, 3H), 1.84-1.74 (m, 2H), 1.05 (d, J=7.2 Hz, 3H), 0.89 (d, J=6.8 Hz, 3H), 0.73 (d, J=6.8 Hz, 3H), 0.29 (d, J=6.4 Hz, 3H).

EXAMPLE 29

11-Deoxy-3-(morpholin-4-yl)-11-{2-oxo-2-[4-(3-carboxy-1-cyclopropl-6-fluoro-4-oxo-1,4-dihydro-quinolin-7-yl)piperazin-1-yl]ethoxyimino}rifamycin S

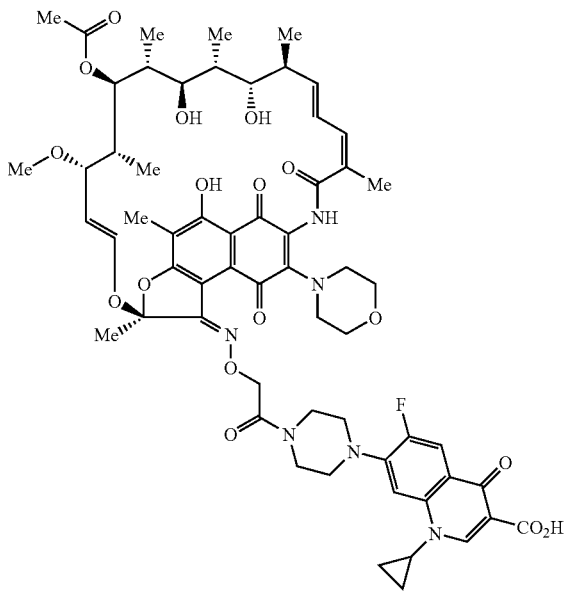

Synthesis: Step 1. 11-Deoxy-3-(morpholin-4-yl)-11-{5-(2,5-dioxopyrrolidin-1-yloxycarbonyl-methoxyimino)}rifamycin S To a stirred solution of 11-deoxy-3-(morpholin-4-yl)-11-(4-carboxyinethoxyimino)-rifamycin S (15.0 mg, 0.018 mmol) and EDC (7.0 mg, 0.037 mmol) in THF (1.0 mL) was added N-hydroxy succinimide (5.4 mg, 0.047 mmol) and DMAP (0.3 mg, 0.002 mmol). The reaction mixture was allowed to stir overnight at 45° C. and then partitioned between ethyl acetate and water. The organic layer was separated, dried over sodium sulfate, concentrated in vacuo to dryness. The title compound was afforded as produced as a purple solid (16 mg, >95%), which could be used for next step without further purification. ESI MS m/z 951.2 (M+H)$^+$.

Step 2. 11-Deoxy-3-(morpholin-4-yl)-11-{2-oxo-2-[4-(3-carboxy-1-cyclopropl-6-fluoro-4-oxo-1,4-dihydroquinolin-7-yl)piperazin-1-yl]ethoxyimino}rifamycin S To a stirred solution of product in step 1 (5.0 mg, 0.005 mmol) was added 1-cyclopropyl-6-fluoro-4-oxo-7-piperazin-1-yl-1,4-dihydroquinoline-3-carboxylic acid (ciprofloxacin, 12.0 mg, 0.033 mmol) in DMF (0.5 mL) and TEA (2 µL, 0.014 mmol). The reaction solution was allowed to stir for 4 hours at 45° C. and then partitioned between ethyl acetate and water. The organic layer was separated, dried over sodium sulfate, concentrated in vacuo to dryness. The crude product was purified by preparative thin layer chromatography (10% MeOH/DCM) to give the title compound as a purple solid (5.6 mg, 91%). ESI MS m/z 1167.3 (M+H)$^+$; $^1$H NMR (400 MHz, CDCl$_3$) δ 14.89 (s, 1H), 13.04 (s, 1H), 8.79 (s, 1H), 8.07 (d, J=8.8 Hz, 1H), 7.55 (s, 1H), 7.40 (d, J=7.2 Hz, 1H), 7.02-6.97 (m, 1H), 6.33 (d, J=10.8 Hz, 1H), 6.16-6.09 (m, 2H), 5.25 (dd, J=6.0, 12.0 Hz, 1H), 5.11 (d, J=10.0 Hz, 1H), 4.94 (d, J$_{AB}$=13.6 Hz, 1H), 4.86 (d, J$_{AB}$=13.6 Hz, 1H), 4.05-3.75 (m,~9H), 3.55-3.33 (m,~10H), 3.12 (s, 3H), 3.06 (d, J=10.0 Hz, 1H), 2.40-2.34 (m, 1H), 2.20 (s, 3H), 2.09 (s, 3H), 2.05 (s, 3H), 2.00 (s, 3H), 1.85-1.79 (m, 2H), 1.71-1.58 (m, 2H), 1.38-1.20 (m, 4H), 1.05 (d, J=6.8 Hz, 3H), 0.90 (d, J=7.2 Hz, 3H), 0.74 (d, J=6.8 Hz, 3H), 0.32 (d, J=6.8 Hz, 3H).

EXAMPLE 30

11-Deoxy-3-(morpholin-4-yl)-11-{2-oxo-2-[4-(3-carboxy-1-cyclopropyl-6-fluoro-8-methoxy-4-oxo-1,4-dihydroquinolin-7-yl)-2-methylpiperazin-1-yl]ethoxyimino}rifamycin S

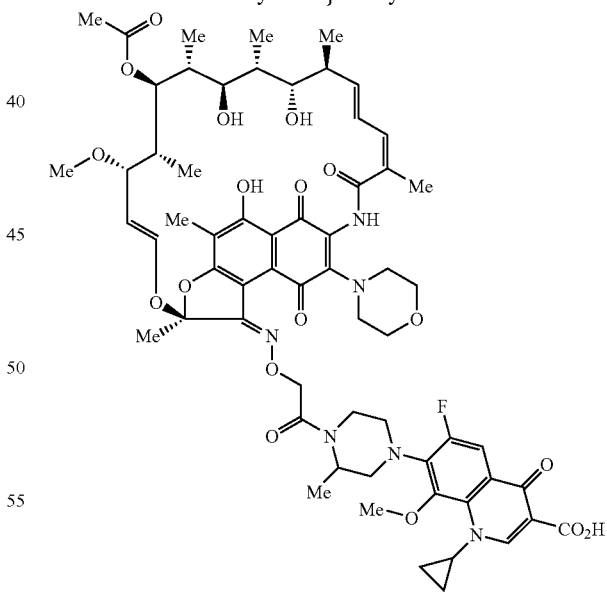

Synthesis: The title compound was prepared by following the same procedure as described for Step 2 of example 30 except (R/S)-1-cyclopropylcyclopropyl-6-fluoro-8-methoxy-7-(3-methyl-piperazin-1-yl)-4-oxo-1,4-dihydro-quinoline-3-carboxylic acid (gatifloxacin) was used in place of 1-cyclopropyl-6-fluoro-4-oxo-7-piperazin-1-yl-1,4-dihydroquinoline-3-carboxylic acid (ciprofloxacin). ESI MS m/z 1211.3 (M+H)$^+$.

EXAMPLE 32

(R/S)-11-Deoxy-3-(morpholin-4-yl)-11-{2-oxo-2-[4-(3-carboxy-1-cyclopropyl-6-fluoro-8-chloro-4-oxo-1,4-dihydroquinolin-7-yl)-3-aminopyrrolidin-1-yl]ethoxyimino}rifamycin S

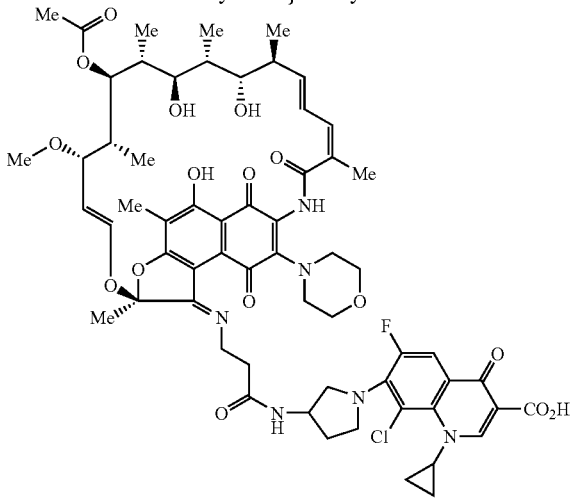

Synthesis: The title compound was prepared by following the same procedure as described for the preparation Step 2 in Example 30 except (R/S)-7-[3 aminopyrrolidin-1-yl]-8-chloro-1-cyclopropyl-6-fluoro-4-oxo-1,4-dihydro-quinoline-3-carboxylic acid hydrochloride (clinafloxacin hydrochloride) was used in place of 1-cyclopropyl-6-fluoro-4-oxo-7-piperazin-1-yl-1,4-dihydroquinoline-3-carboxylic acid (ciprofloxacin). ESI MS m/z 1201.3 (M+H)$^+$.

EXAMPLE 32

11-Deoxy-11-{2-oxo-2-[4-(3-carboxy-1-cyclopropl-6-fluoro-4-oxo-1,4 -dihydroquinolin-7-yl)piperazin-1-yl]ethoxyimino}rifamycin S

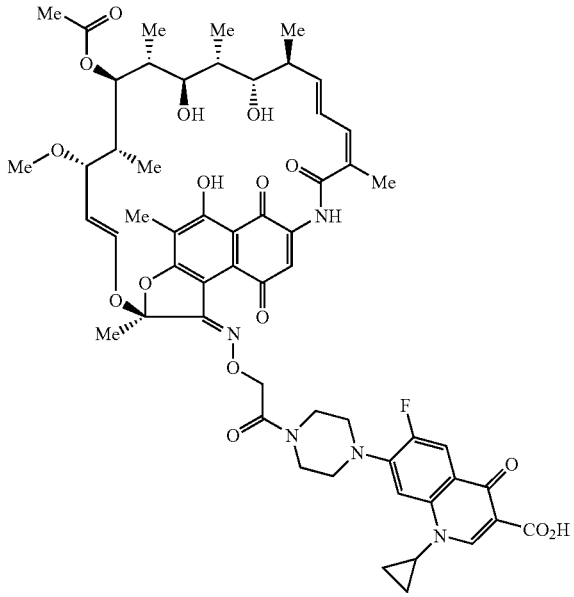

Synthesis: Step 1. 1-Cyclopropyl-6-fluoro-4-oxo-7-piperazin-4-chloroacetyl-1-yl-1, -4-dihydroquinoline-3-carboxylic acid: To a stirred solution of 1-cyclopropyl-6-fluoro-4-oxo-7-piperazin-1-yl-1,4-dihydroquinoline-3-carboxylic acid (ciprofloxacin) (216 mg, 0.65 mmol) in DMF (6.0 mL) was added chloroacetyl chloride (70 µL, 0.88 mmol) slowly. The reaction mixture was allowed to stir for 20 minutes at room temperature. The reactant resultant mixture was partitioned between DCM/isopropyl alcohol (95/5, v/v) and water. The organic layer was separated, dried over sodium sulfate, concentrated in vacuo to dryness. The title compound was obtained as a white solid (150 mg, 56%), which could be used in the next step without further purification. ESI MS m/z 408.2 (M+H)$^+$.

Step 2. 11-Deoxy-11-{2-oxo-2-[4-(3-carboxy-1-cyclopropl-6-fluoro-4-oxo-1,4-dihydroquinolin-7-yl)piperazin-1-yl]ethoxyimino}rifamycin S To a stirred mixture of 11-deoxy-11-hydroxyiminorifamycin S (90 mg, 0.13 mmol), sodium bicarbonate (80 mg, 0.95 mmol) and sodium iodide (58 mg, 0.39 mmol) in DMF (2.0 mL) was added the a solution of the above product of Step 1 (57 mg, 0.14 mmol) in DMF (1.0 mL) slowly at 70° C. The reaction solution was allowed to stir for 1.5 hours at 70° C. and then partitioned between ethyl acetate and water. The organic layer was separated, dried over sodium sulfate, concentrated in vacuo to dryness. The crude product was purified by preparative thin layer chromatography (10% MeOH/DCM) to give the title compound as an orange solid (8.2 mg, 6%). ESI MS m/z 1082.3 (M+H)$^+$; $^1$H NMR (400 MHz, CDCl$_3$) δ 14.99 (br s, 1H), 12.72 (s, 1H), 8.81 (s, 1H), 8.48 (s, 1H), 8.10 (d, J=12.8 Hz, 1H), 7.60 (s, 1H), 7.48 (d, J=6.8 Hz, 1H), 6.62 (d, J=12.4 Hz, 1H), 6.39-6.28 (m, 2H), 5.91 (dd, J=6.4, 15.6 Hz, 1H), 5.21-5.15 (m, 2H), 5.00 (d, J=14.4 Hz, 1H), 4.53 (d, J=10.8 Hz, 1H), 4.06-3.78 (m, 5H), 3.65-3.25 (m,~8H), 3.16 (s, 3H), 2.99 (d, J=10.0 Hz, 1H), 2.40-2.34 (m, 1H), 2.29 (s, 3H), 2.12-2.00 (m, 1H), 2.05 (s, 3H), 2.04 (s, 3H), 1.98 (s, 3H), 1.80-1.75 (m, 1H), 1.51-1.39 (m, 3H), 1.26-1.19 (m, 2H), 1.02 (d, J=6.8 Hz, 3H), 0.82 (d, J=6.8 Hz, 3H), 0.66 (d, J=6.8 Hz, 3H), 0.24 (d, J=7.2 Hz, 3H).

EXAMPLE 33

11-Deoxy-3-[4-(3-carboxy-1-cyclopropyl-6-fluoro-4-oxo-1,4-dihydroquinolin-7-yl)piperazin-1-yl]-11-hydroxyiminorifamycin S

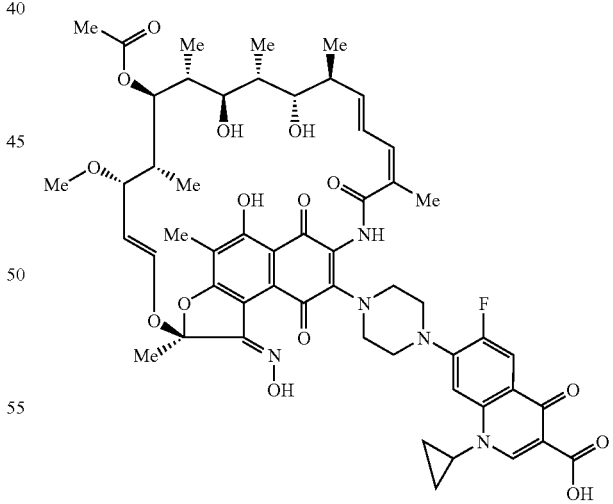

Synthesis: To a stirred solution of 3-[4-(3-carboxy-1-cyclopropyl-6-fluoro-4-oxo-1,4-dihydroquinolin-7-yl)piperazin-1-yl]rifamycin S (10.0 mg, 0.01 mmol) in MeOH (0.3 mL) and THF (0.3 mL) was added pyridine (10 µL, 0.13 mmol) and hydroxylamine hydrochloride (9.0 mg, 0.13 mmol). The reaction solution was allowed to stir 5 days at room temperature. The reaction mixture was purified by preparative thin layer chromatography (10% MeOH/DCM)

to give the title compound as a purple-brown solid (8.0 mg, 78%). ESI MS m/z 1040.2 (M+H)+.

EXAMPLE 34

11-Deoxy-3-(morpholin-4-yl)-11-hydroxyiminorifamycin S

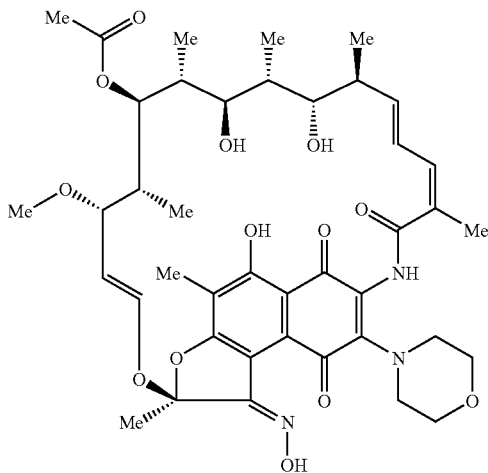

Synthesis: The title compound was prepared by following the same procedure as described for Example 33 except 3-(morpholin-4-yl)-rifamycin S was used in place of 3-[4-(3-carboxy-1-cyclopropyl-6-fluoro-4-oxo-1,4-dihydroquinolin-7-yl)piperazin-1-yl]rifamycin S. The title compound was obtained as a purple solid. ESI MS m/z 796.1 (M+H)+.

EXAMPLE 35

11-Deoxy-3-(morpholin-4-yl)-11-methoxyiminorifamycin S

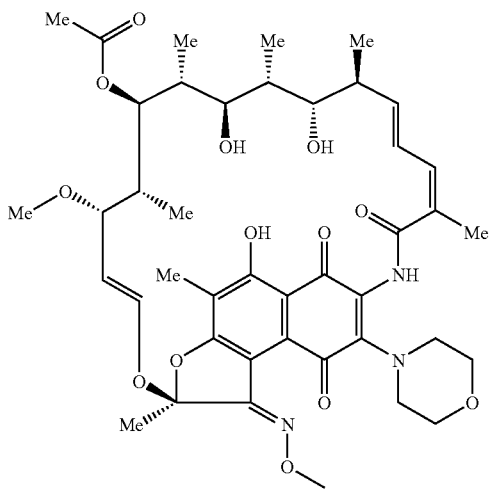

Synthesis: The title compound was prepared by following the same procedure as described for Example 34 except methoxyamine hydrochloride was used in place of hydroxylamine hydrochloride. The title compound was obtained as a purple solid. ESI MS m/z 810.2 (M+H)+; $^1$H NMR (400 MHz, CDCl$_3$) δ 13.11 (s, 1H), 7.65 (s, 1H), 7.02-6.97 (m, 1H), 6.33 (d, J=10.4 Hz, 1H), 6.10 (dd, J=6.0, 15.6 Hz, 1H), 6.03 (d, J=12.4 Hz, 1H), 5.18-5.11 (m, 2H), 4.05 (s, 3H), 3.94-3.89 (m, 4H), 3.78-3.73 (m, 2H), 3.54-3.50 (m, 1H), 3.37-3.30 (m, 2H), 3.11 (s, 3H), 3.07-3.04 (m, 1H), 2.40-2.34 (m, 1H), 2.20 (s, 3H), 2.12 (s, 3H), 2.08 (s, 3H), 1.99 (s, 3H), 1.87-1.78 (m, 2H), 1.05 (d, J=6.8 Hz, 3H), 0.89 (d, J=7.2 Hz, 3H), 0.73 (d, J=6.8 Hz, 3H), 0.33 (d, J=7.2 Hz, 3H).

EXAMPLE 36

11-Deoxy-3-(morpholin-4-yl)-11-allyloxyiminorifamycin S

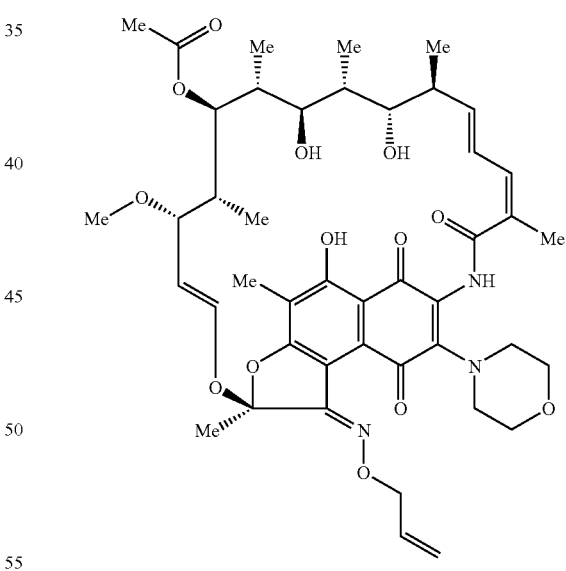

Synthesis: The title compound was prepared by following the same procedure as described for Example 34 except allyloxyamine hydrochloride was used in place of hydroxylamine hydrochloride. The title compound was achieved as a purple solid. ESI MS m/z 810.2 (M+H)+.

EXAMPLE 37

11-Deoxy-11-hydroxyimino-3-(4-methylpiperazin-1-yl)aminomethenylrifamycin SV:

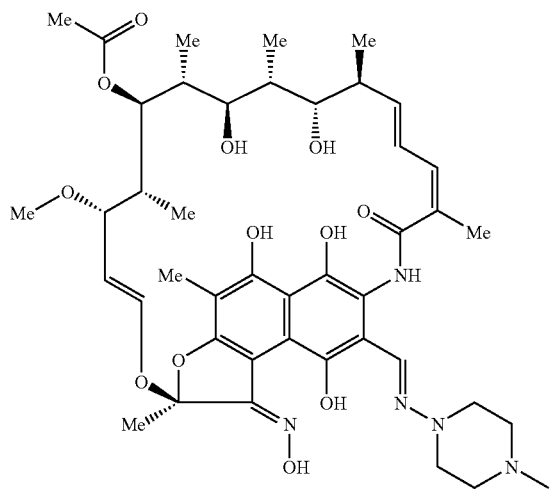

Synthesis: To a stirred solution of 11-deoxy-11-hydroxyiminorifamycin S (71 mg, 0.1 mmol) in DMF (2 mL) at room temperature was added N,N-dihydroxymethyl-tert-butylamine (35 mg, 0.26 mmol). The resultant mixture was heated at 40° C. for 1 h, and poured into water acidified with acetic acid. The suspension was extracted with DCM (10 mL), and the extract was mixed with 1-amino-4-methylpiperazine. The resultant mixture was allowed to stir at 40° C. for 30 min, and washed with 1% acetic acid solution. The organic layer was dried, concentrated in vacuo, and the resultant residue was purified by preparative thin layer chromatography (5% methanol in DCM in the presence of 1% acetic acid, and 1% TEA) to give an orange solid (5 mg, 6%). ESI MS m/z 838.3 (M+H)$^+$.

EXAMPLE 38

11-Deoxy-11-hydroxyimino-3-(4-methylpiperazin-1-yl)aminomethenylrifamycin S

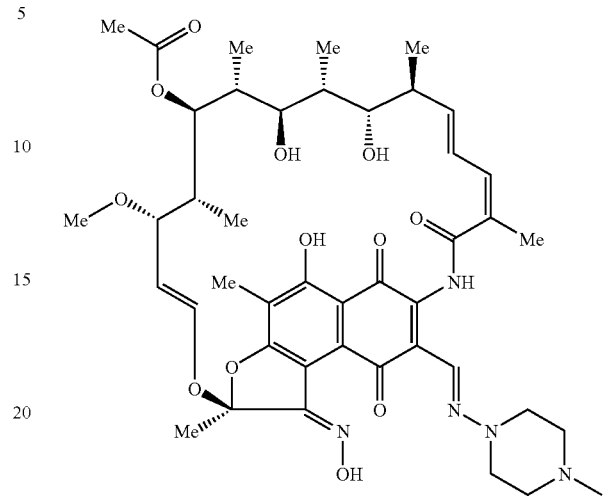

Synthesis: 11-Deoxy-11-hydroxyimino-3-(4-methylpiperazin-1-yl)aminomethenylrifamycin SV: (2 mg) prepared as described in Example 38 was dissolved in 1 mL of ethyl acetate. To the resultant solution was added 1 mL PBS buffer, followed by K$_3$Fe(CN)$_6$ (5 mg). The reaction mixture was allowed to stir at room temperature for one hour, and partitioned between ethyl acetate and water. The separated organic layer was washed with 5% citric acid (2×), dried over sodium sulfate, concentrated in vacuo to afford a dark brown solid after purification by preparative thin layer chromatography (10% methanol in DCM in the presence of 1% acetic acid) (1.5 mg, 16%). ESI MS m/z 836 (M+H$^+$).

EXAMPLE 39

3-[4-(3-Carboxy-1-cyclopropyl-6-fluoro-4-oxo-1,4-dihydroquinolin-7-yl)piperazin-1-yl-aminomethylenyl]-11-deoxy-11-hydroxyiminorifamycin SV:

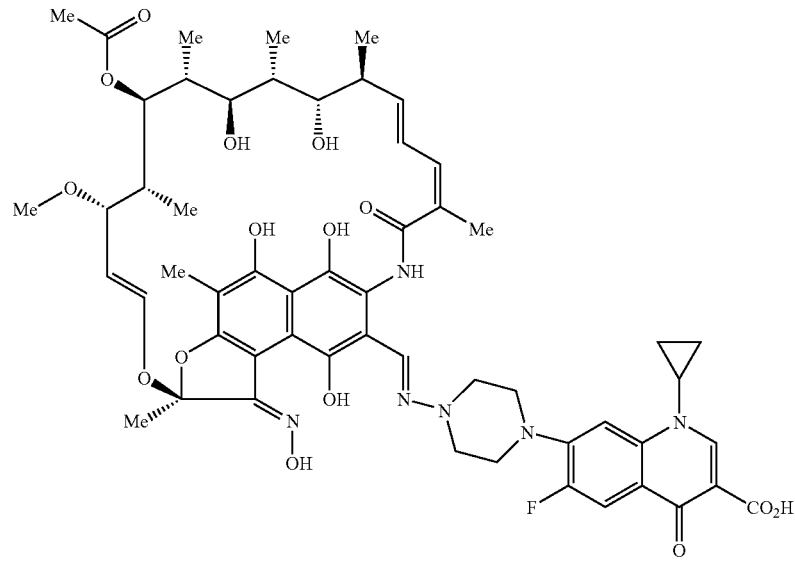

Synthesis: Step 1. 7-(4-Aminopiperazin-1-yl)-1-cyclopropyl-6-fluoro-4-oxo-1,4-dihydroquinoline-3-carboxylic acid: To a stirred suspension of 1-cyclopropyl-6-fluoro-4-oxo-7-piperazin-1-yl-1,4-dihydroquinoline-3-carboxylic acid (ciprofloxacin) (500 mg, 1.5 mmol) in 3 mL acetic acid was added 0.5 mL 3 N HCl solution (1.5 mmol). The solution was cooled to 4° C. and a solution of sodium nitrite (0.13 g, 1.9 mmol) in water (1 mL) was added drop-wise. The suspension was diluted with more solvent to facilitate stirring, and it was allowed to slowly warm up to room temperature and stirring was maintained at this temperature for 5 hours. At this time, analysis of the reaction mixture by LC/MS showed all starting material was converted to 1-cyclopropyl-6-fluoro-7-(4-nitrosopiperazin-1-yl)-4-oxo-1,4-dihydroquinoline-3-carboxylic acid, ESI MS m/z 361 (M+H$^+$). The suspension was basified by addition of solid sodium acetate. The mixture was cooled in an ice bath and zinc powder (590 mg, 9 mmol) was added in portions. The resultant suspension was allowed to slowly warm up to room temperature and stirring was maintained for 18 hours. The suspension was filtered through a layer of celite and the filtrate containing product was used for Step 2 without further purification. ESI MS m/z 347 (M+H$^+$).

Step 2. 3-[4-(3-Carboxy-1-cyclopropl-6-fluoro-4-oxo-1,4-dihydroquinolin-7-yl)piperazin-1-yl-aminomethylenyl]-11-deoxy-11-hydroxyiminorifamycin SV: The title compound may be prepared by using a similar procedure as described for the preparation of Example 37 except 7-(4-aminopiperazin-1-yl)-1-cyclopropyl-6-fluoro-4-oxo-1,4-dihydroquinoline-3-carboxylic acid may be used in place of 1-amino-4-methylpiperazine in methanol/acetic acid.

EXAMPLE 40

(R/S)-3-[4-(3-Carboxy-1-cyclopropyl-6-fluoro-8-methoxy-4-oxo-1,4-dihydroquinolin-7-yl)-2-methylpiperazin-1-yl-aminomethylenyl]-11-deoxy-11-hydroxyiminorifamycin SV:

The title compound may be prepared by using a similar procedure as described for the preparation of Example 39 except (R/S)-1-cyclopropyl-6-fluoro-8-methoxy-7-(3-methylpiperazin-1-yl)-4-oxo-1,4-dihydroquinoline-3-carboxylic acid (gatifloxacin) may be used in place of 1-cyclopropyl-6-fluoro-4-oxo-7-(piperazin-1-yl)-1,4-dihydro-quinoline-3-carboxylic acid (ciprofloxacin).

One skilled in the art readily appreciates that the disclosed invention is well adapted to carry out the mentioned and inherent objectives. Linkers, fluorophores, ligands of bacterial ribosome and functional equivalents thereof, pharmaceutical compositions, treatments, methods, procedures, examples and techniques described herein are presented as representative of the preferred embodiments and are not intended as limitations of the scope of the invention. Thus, other uses will occur to those skilled in the art that are encompassed within the spirit and scope of the described invention.

REFERENCES CITED

The content of the following documents is hereby incorporated by reference.

U.S. Patent Documents

U.S. Pat. No. 4,002,754
U.S. Pat. No. 4,164,499
U.S. Pat. No. 4,341,785

Other Patent Documents

European Patent No. 0190709 B1
European Patent No. 0228606 B1
International Patent Application No. WO 94/28002
International Patent Application No. WO 03/051299 A2

Other Publications

Bartolucci, C., Cellai, L., Cerrini, S., Lamba, D., Segre, A., Brizzi, V., Brufani, M. *Helvetica Chimica Acta*, 1990, vol. 73, pp. 185-190.
Brufani, M., Cerrini, S., Fedeli, W., Vaciago, A. *J. Mol. Biol.* 1974, vol. 87, pp. 409-435.
Bundgaard, H. ed.; *Design of Prodrugs*, Elsevier, 1985.

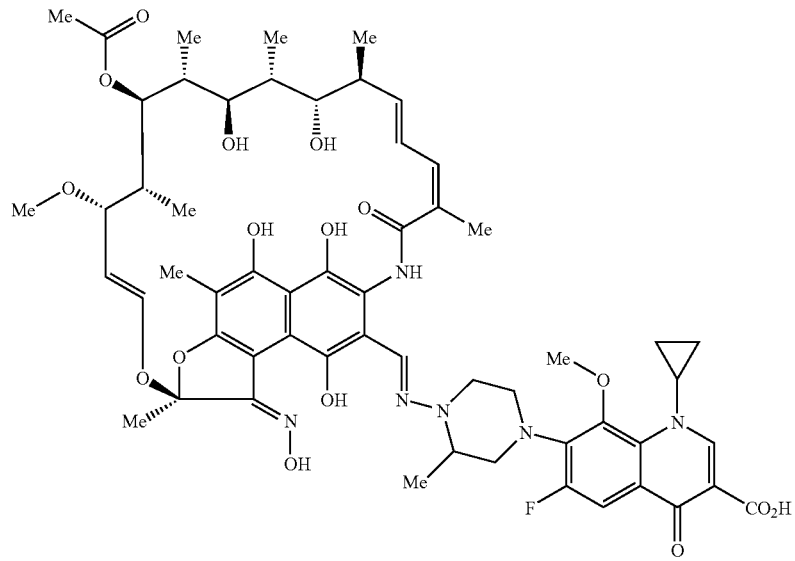

Bundgaard, H., et al., *Journal of Pharmaceutical Sciences*, vol. 77, p. 285, 1988.

Bundgaard, H., *Advanced Drug Delivery Reviews*, vol. 8, pp. 1-38, 1992.

Farr, B. M. Rifamycins, in *Principles and Practice of Infectious Diseases*; Mandell, G. L., Bennett, J. E., Dolin, R., Eds.; Churchhill Livingstone: Philadelphia, pp. 348-361.

Kakeya, N., et. al., *Chem Phar Bull*, vol. 32, p. 692, 1984.

Krosgaard-Larsen and Bundgaard, H., eds.; *A Textbook of Drug Design and Development*, Chapter 5, "Design and Application of Prodrugs," by H. Bundgaard, pp. 113-191, 1991.

Widder, K., et al., eds.; *Methods in Enzymology*, Academic Press, 1985, vol. 42, pp. 309-396.

What is claimed is:

1. A compound of structural Formula I or Formula II:

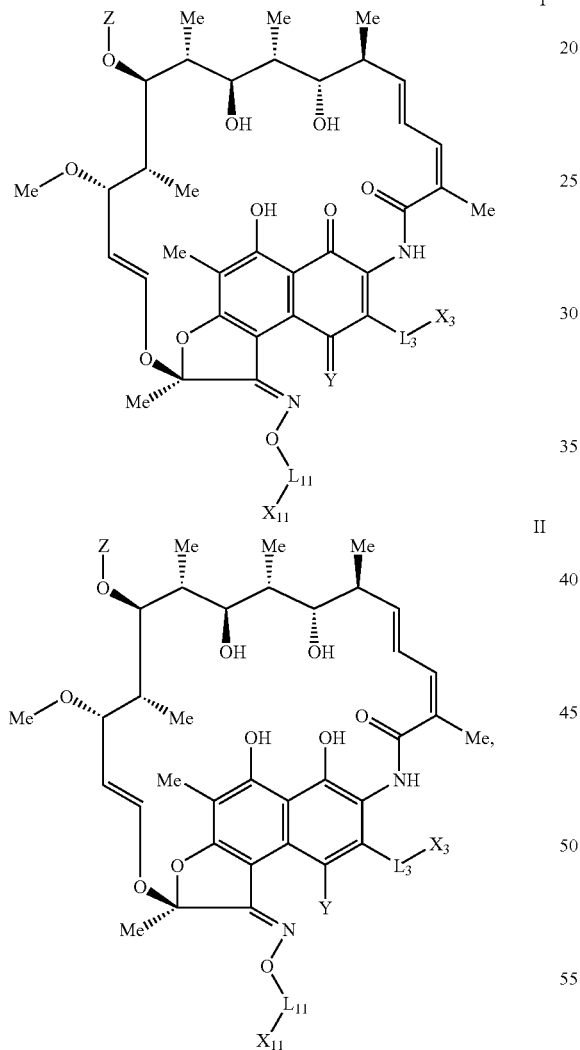

or pharmaceutically acceptable salts thereof;
wherein:

$L_3$ is any combination of 0 to 5 groups which independently are the same or different and are selected from —$CR_1R_2$—, —$NR_3$—, —O—, —C(=O)—, —S(=O)$_{0-2}$—, —C=N—, alkylene, alkenylene, and alkynylene;

$X_3$ is —H, —OH, —$NH_2$, —$CO_2H$, halo, haloalkyl, —CN, alkyl, aryl, or -$Q_3$;

$L_{11}$ is any combination of 0 to 5 groups which independently are the same or different and are selected from —$CR_1R_2$—, —$NR_3$—, —O—, —C(=O)—, —S(=O)$_{0-2}$—, —C=N—, alkylene, alkenylene, and alkynylene;

$X_{11}$ is —H, —OH, —$NH_2$, —$CO_2H$, halo, haloalkyl, —CN, alkyl, aryl, or -$Q_{11}$;

Y is, when the compound is Formula I, =O or =$NR_4$, and, when the compound is Formula II, —OH, —$NHR_4$, —$OR_5$, —$OCH_2CO_2H$, or —$OCH_2CONR_6R_7$;

Z is —H or —$COCH_2R_8$, wherein $R_8$ is —H, —OH, halo, —CN, —$CO_2H$, —$CONR_9R_{10}$, —$NR_{11}R_{12}$, —$OR_{13}$, —$S(=O)_{0-2}R_{14}$, or —$Q_{25}$;

wherein $R_1$ is —H, —OH, —SH, alkyl, cycloalkyl, aryl, alkoxy, alkylthio, alkylamino, or dialkylamino, wherein $R_2$, $R_3$, $R_4$, $R_5$, $R_6$, $R_7$, $R_9$, $R_{10}$, $R_{11}$, $R_{12}$, $R_{13}$, and $R_{14}$ independently are the same or different and are H, alkyl, or aryl, and where $Q_3$, $Q_{11}$, and $Q_{25}$ independently are the same or different and are any of the structures:

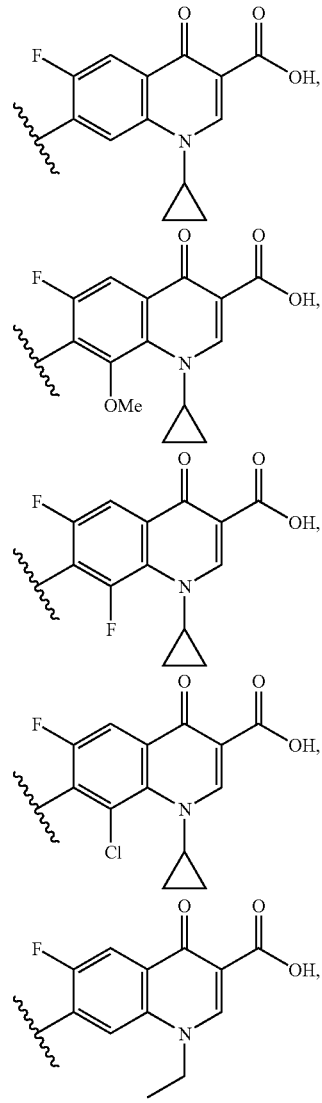

-continued
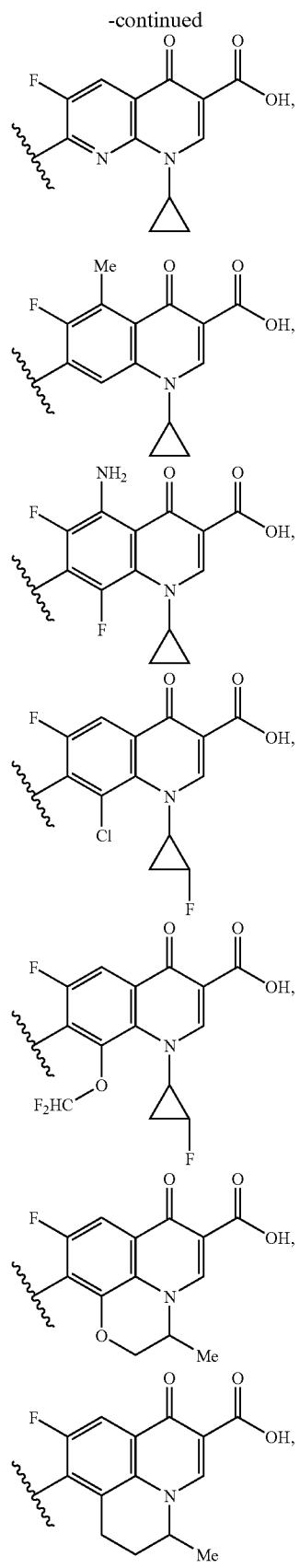
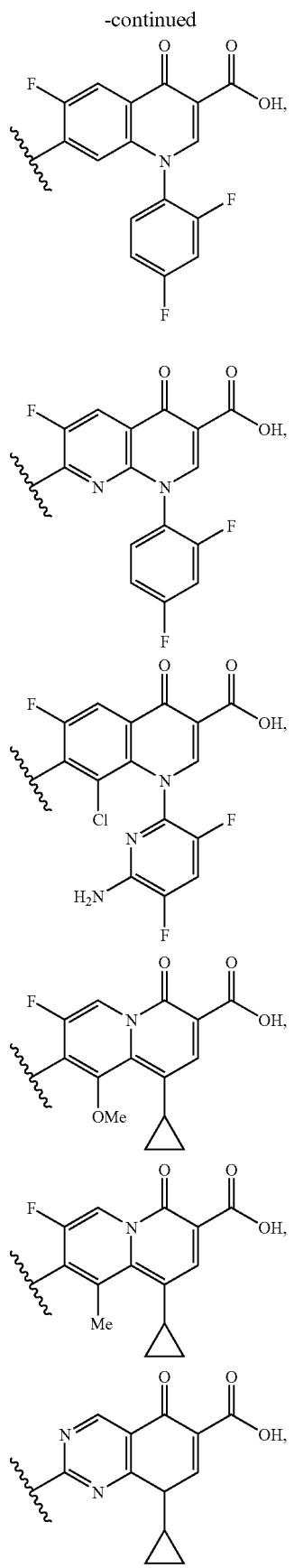

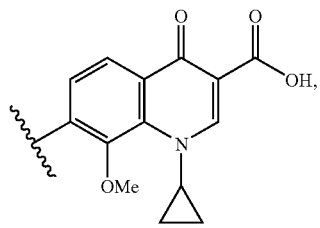
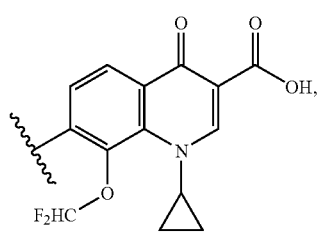
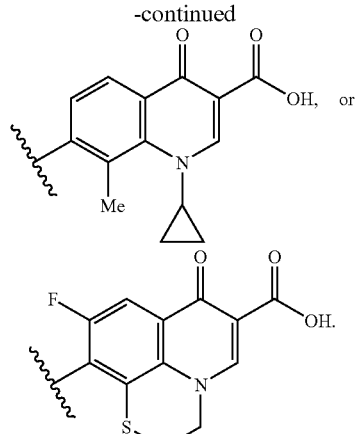
2. The compound of claim 1, wherein Z is —H or —COCH$_3$.
3. A compound having a formula:
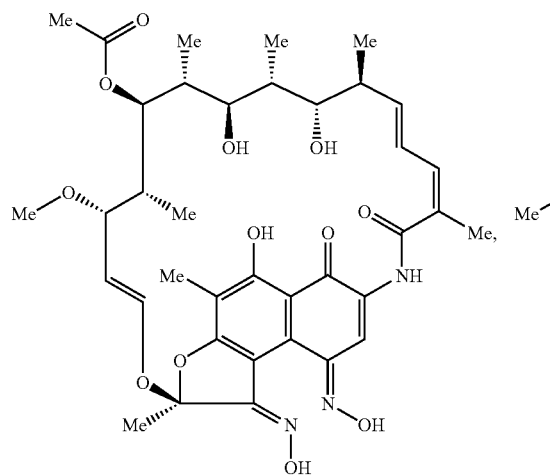
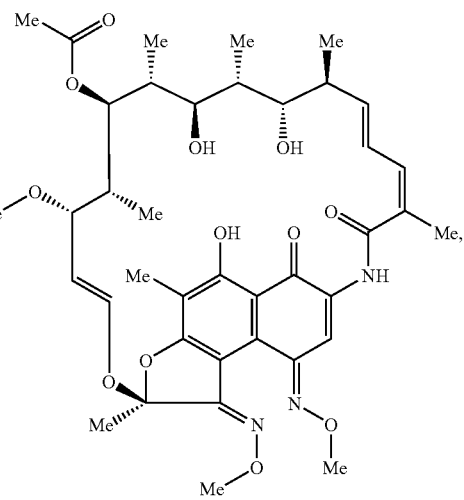
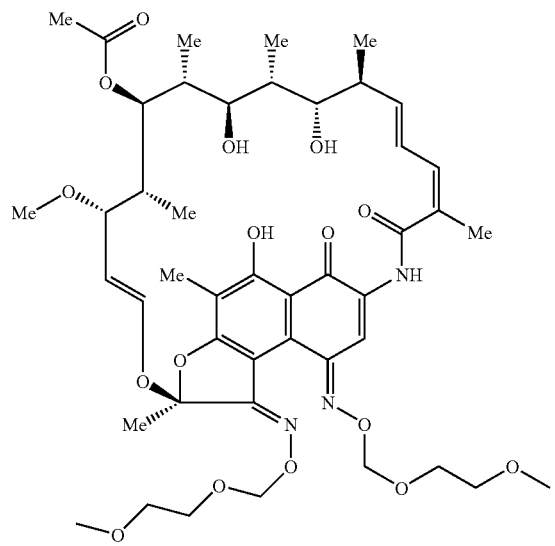
A
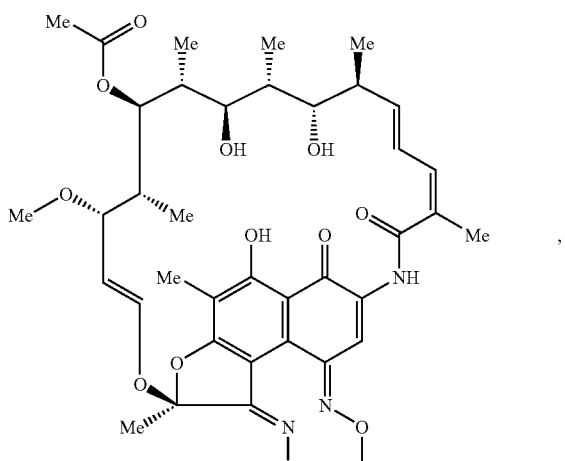
B

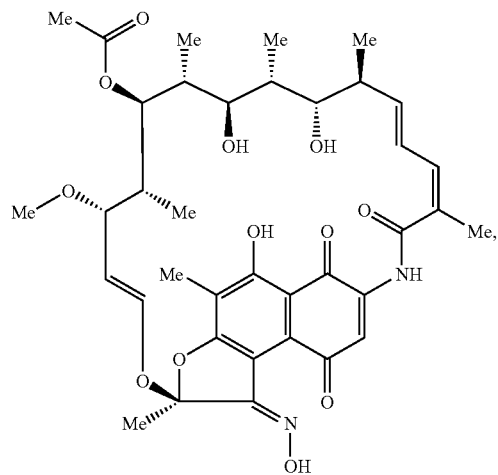
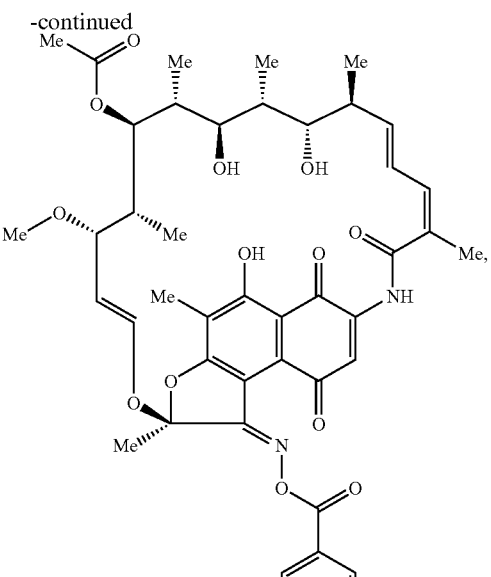
-continued
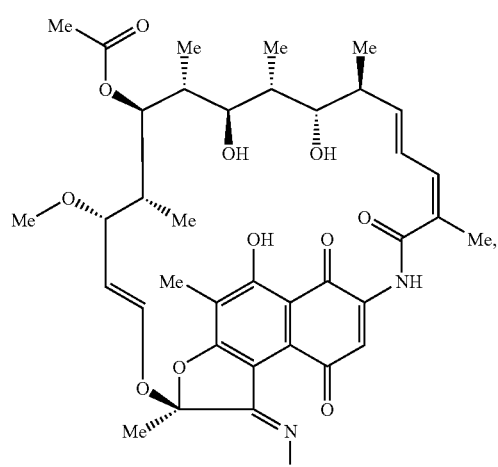
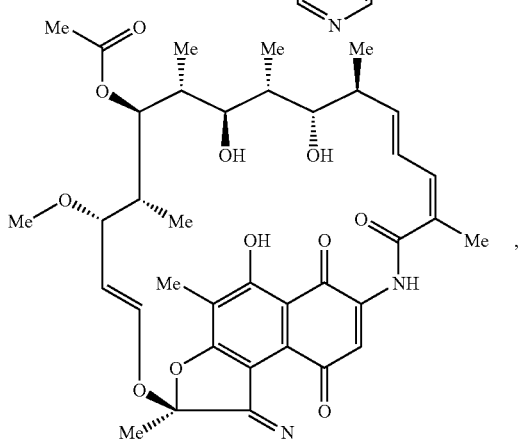
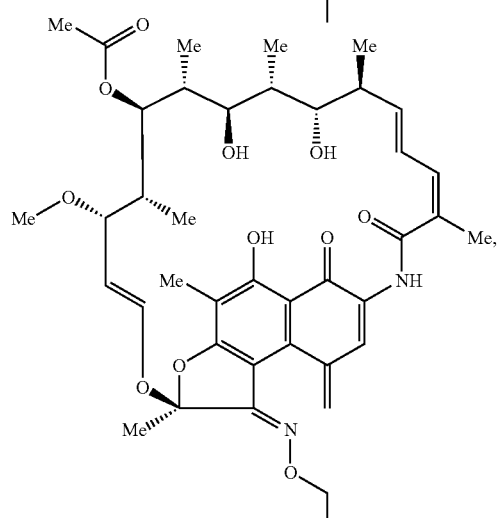
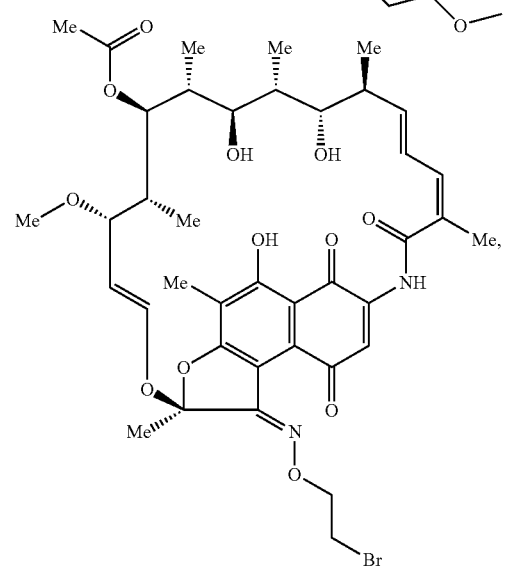

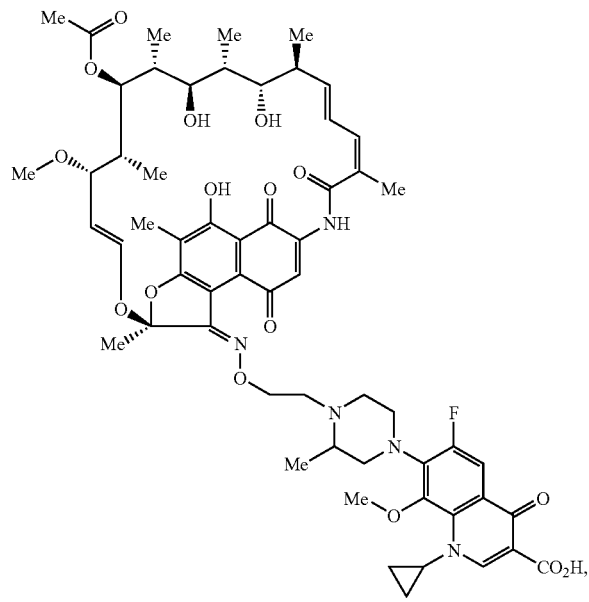
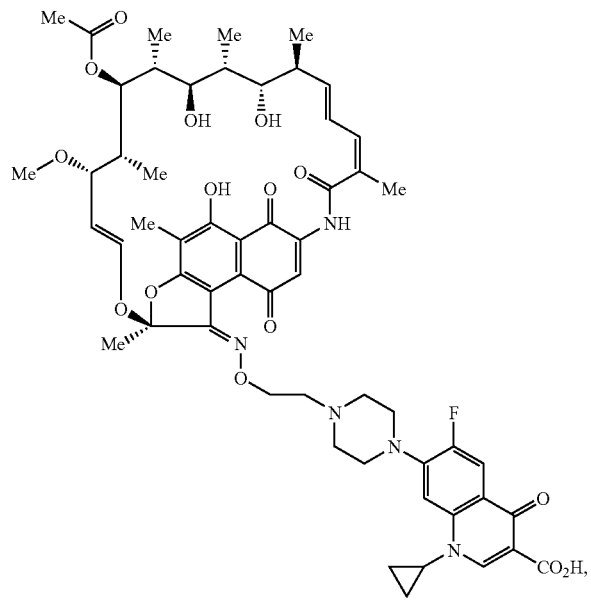
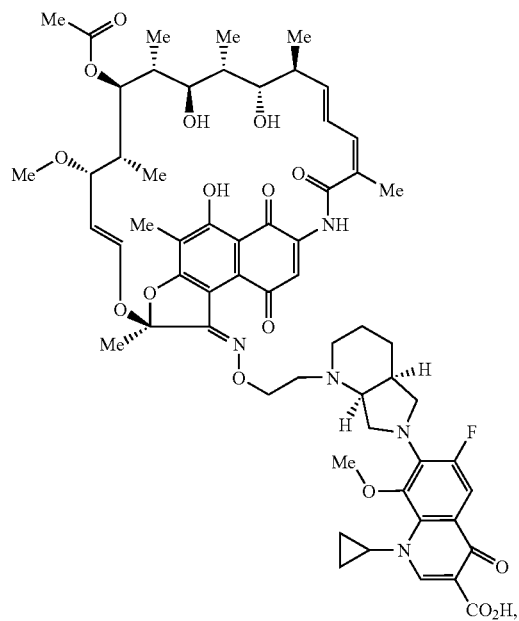

-continued
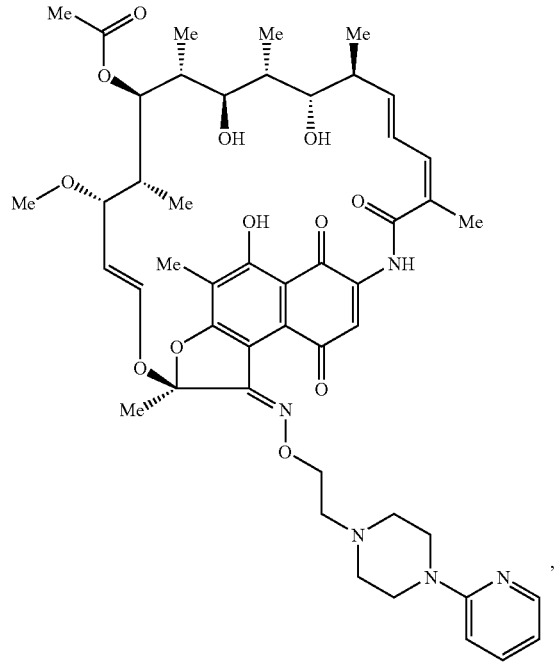
,
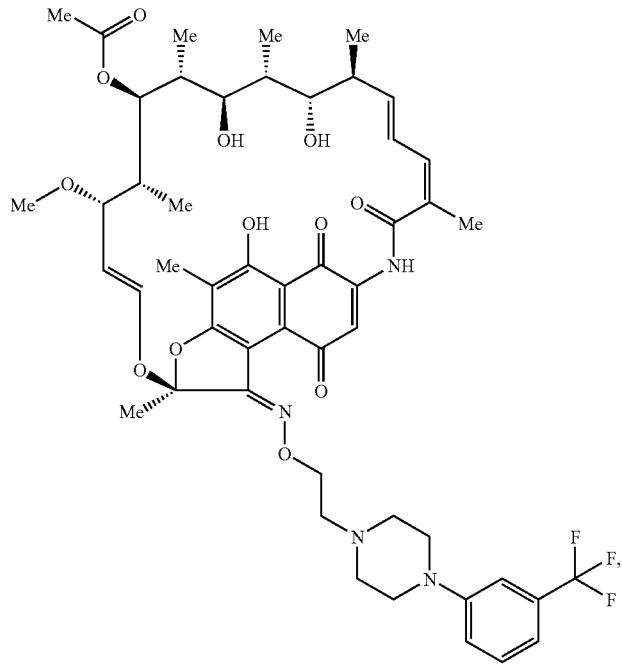
,
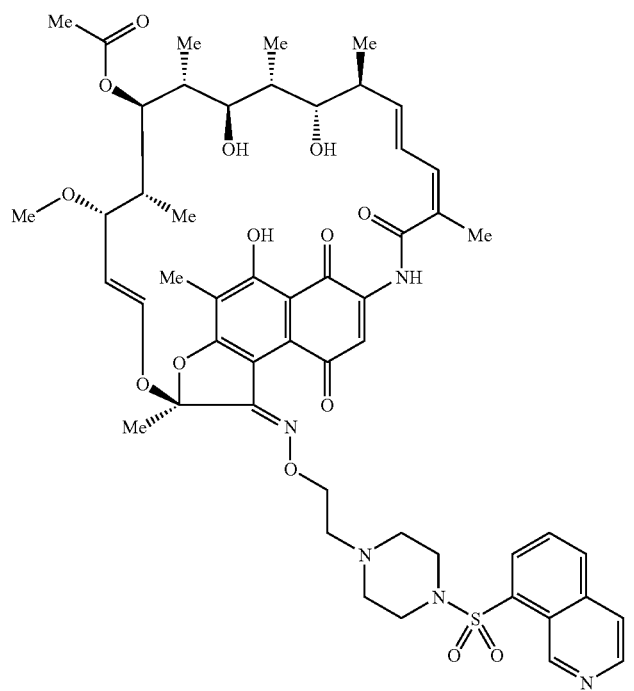
,
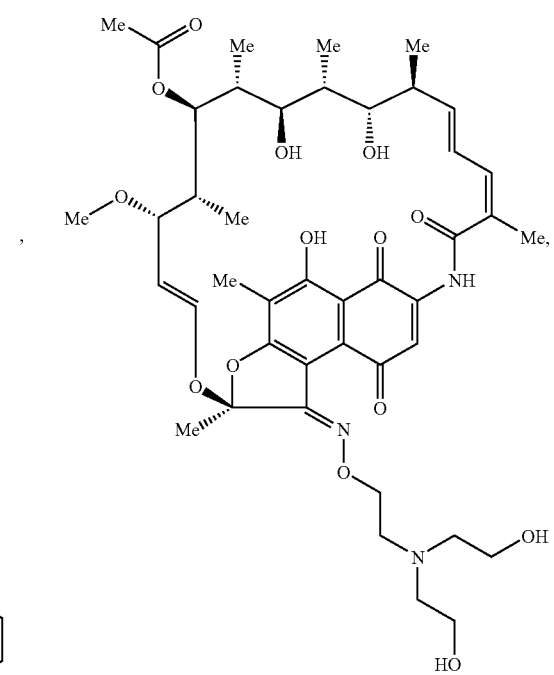

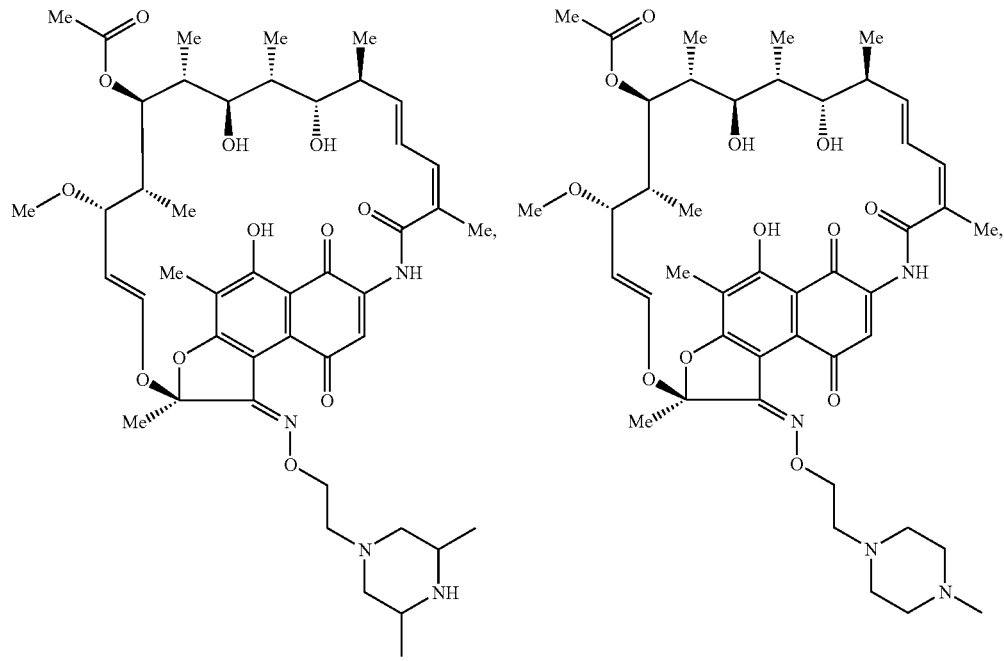
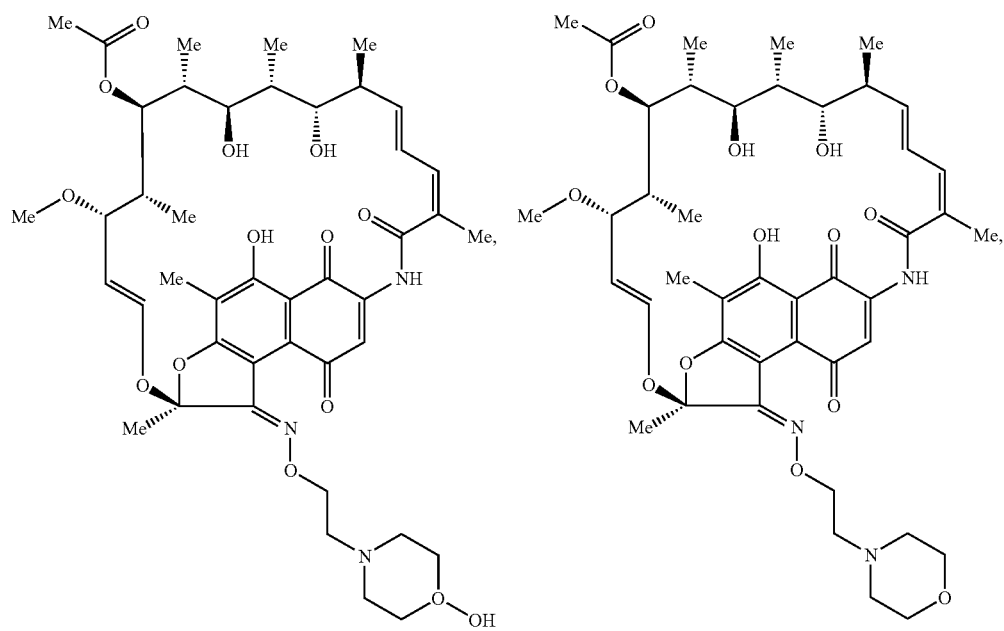

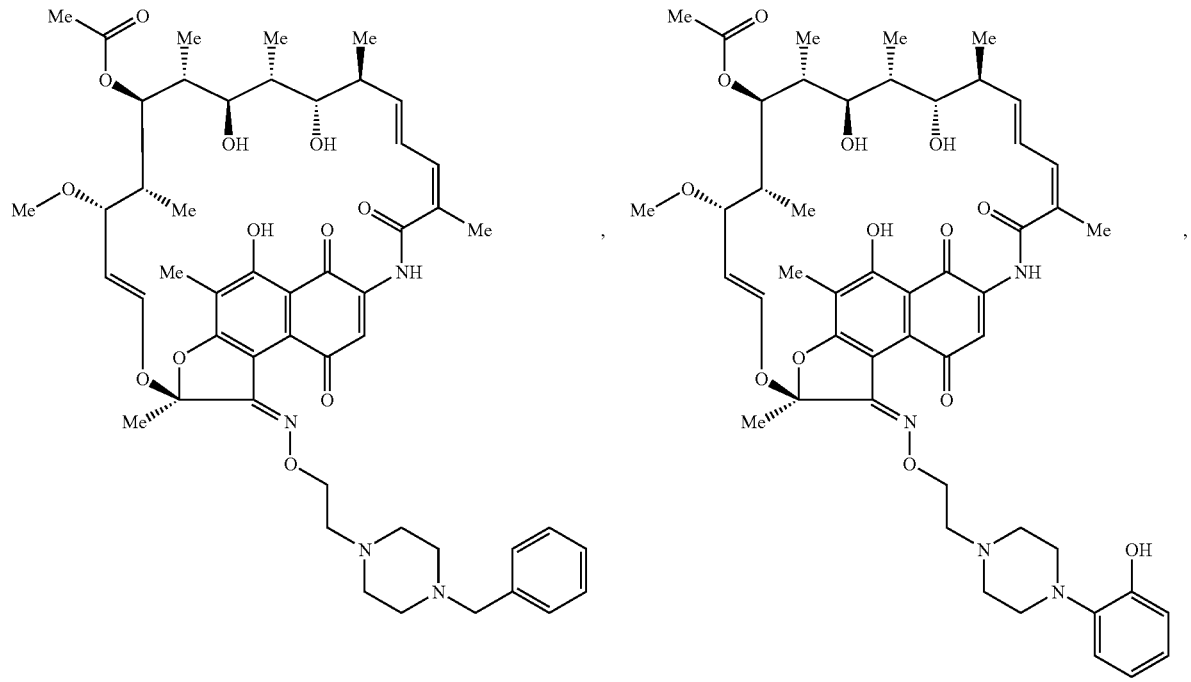
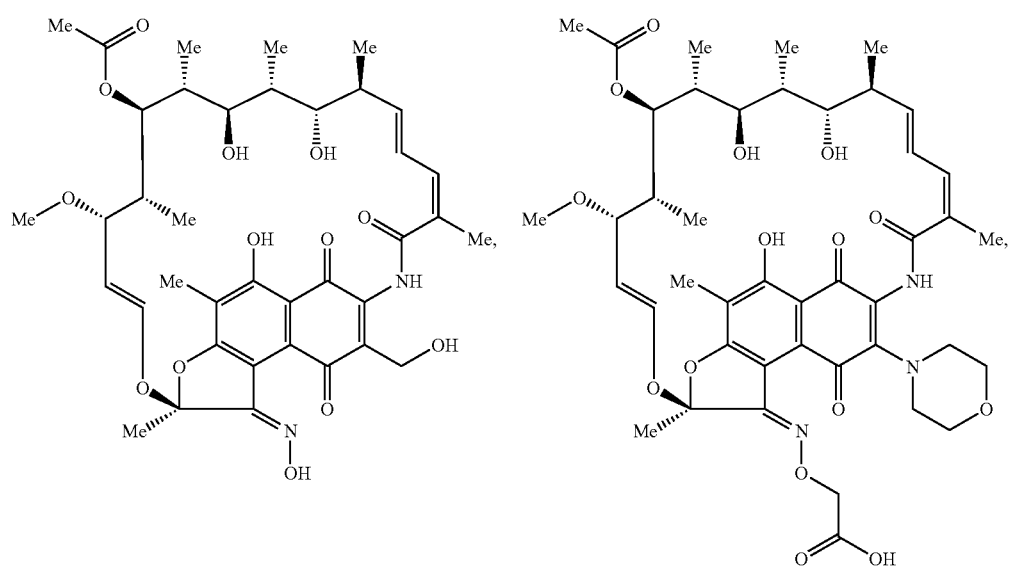

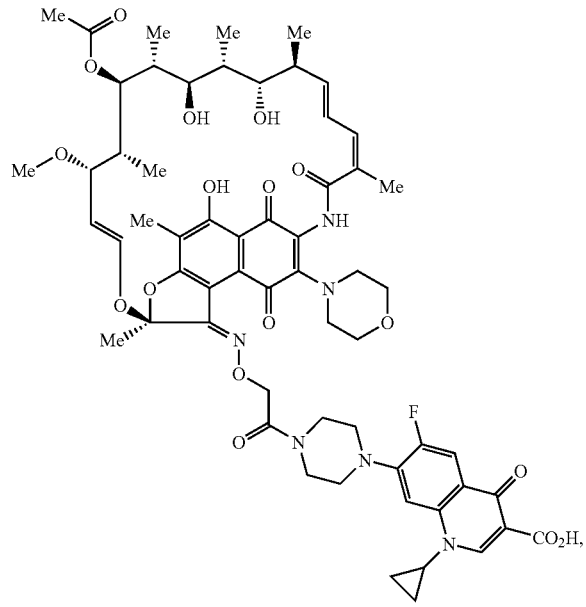
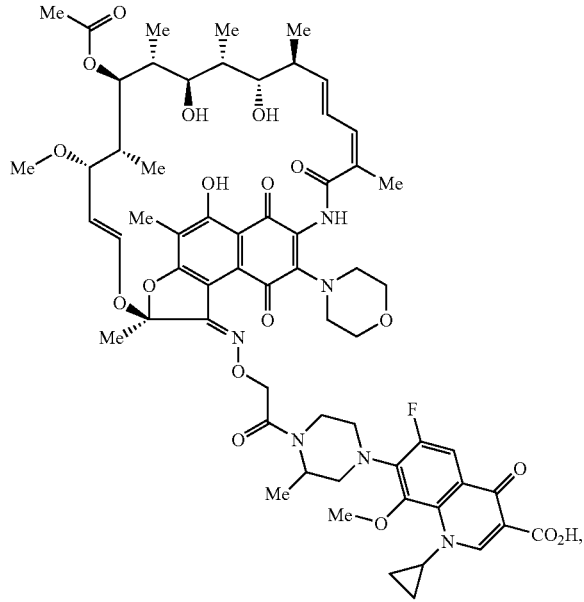
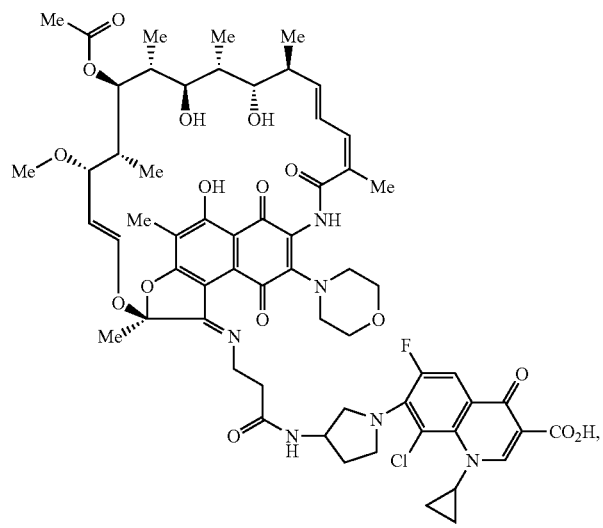
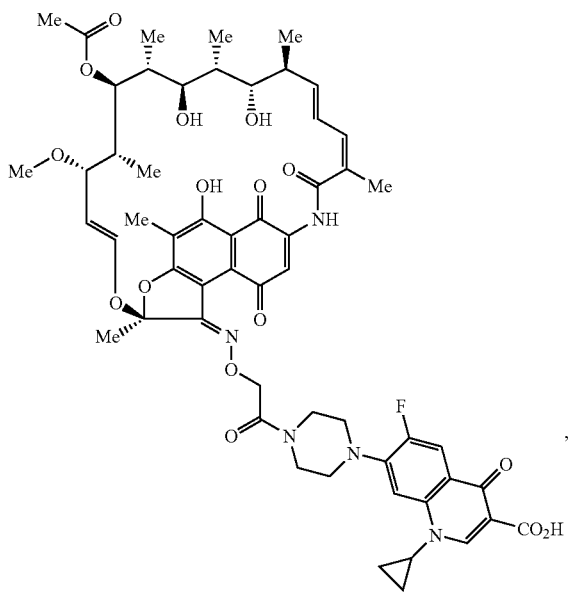

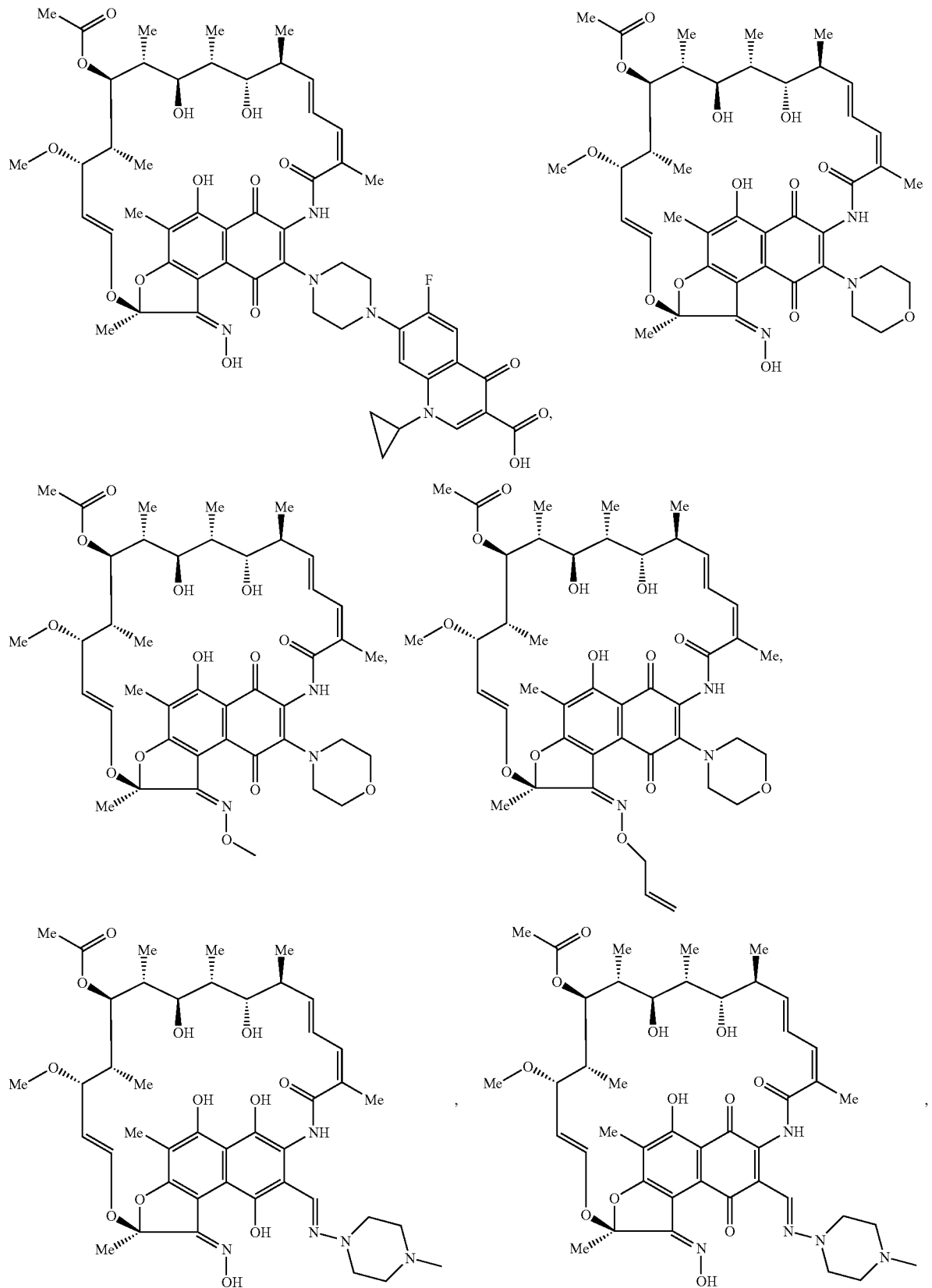

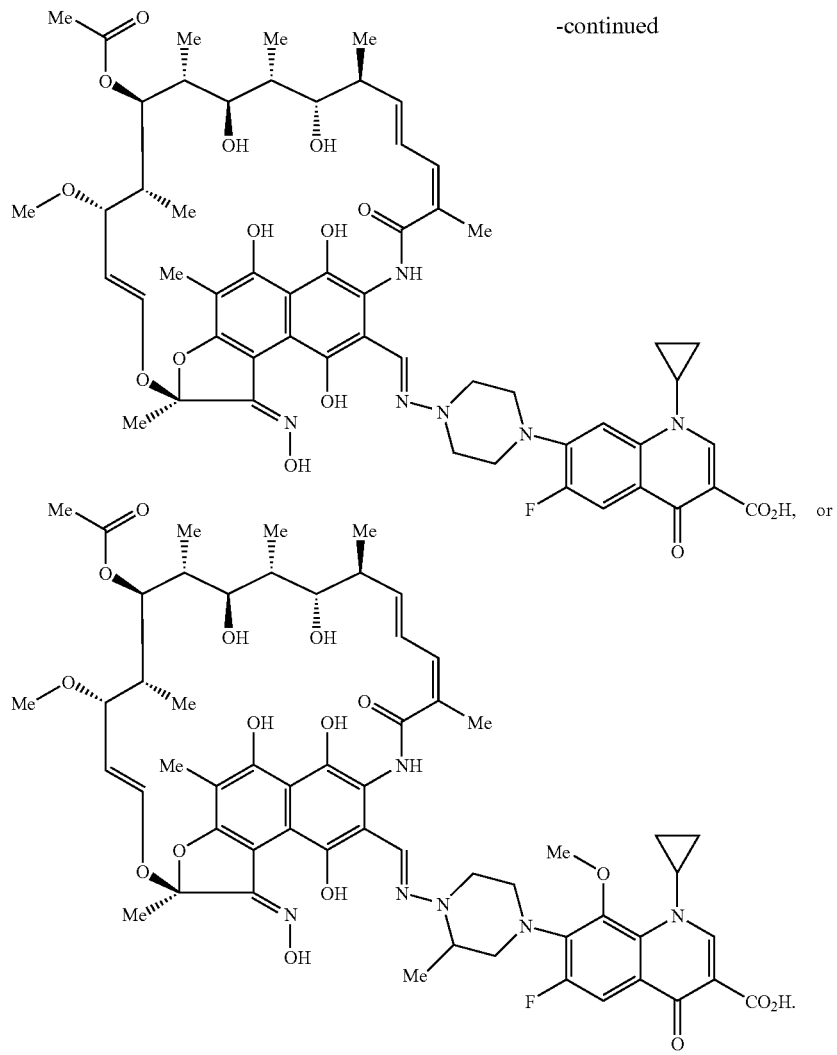

-continued

4. A method of treating a bacterial infection in a subject, comprising administering to the subject an effective amount of the compound of claim 1.

5. The method of claim 4, wherein the bacterial infection is caused by a drug-resistant bacterium.

6. A compound of the formula 4, 11-Dideoxy-4,11-dihydroxyiminorifamycin S

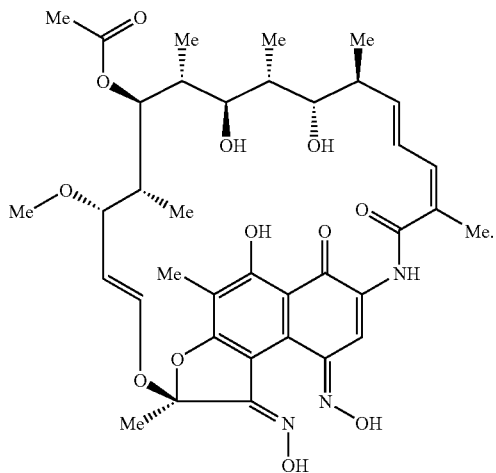

7. A compound of the formula 4, 11-Dideoxy-4, 11-dimethoxyiminorifamycin S

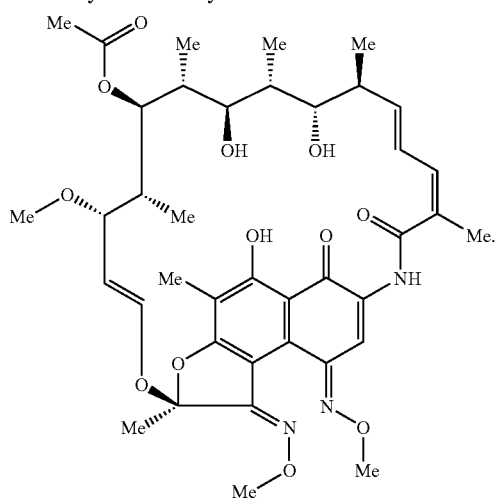

8. A compound of the formula 4, 11-Dideoxy-4, 11-dimethoxyethoxymethoxyiminorifamycin S (A) or 4, 11-Dideoxy-4-methoxyethoxymethoxyimino-11-hydroxyiminorifamycin S (B):

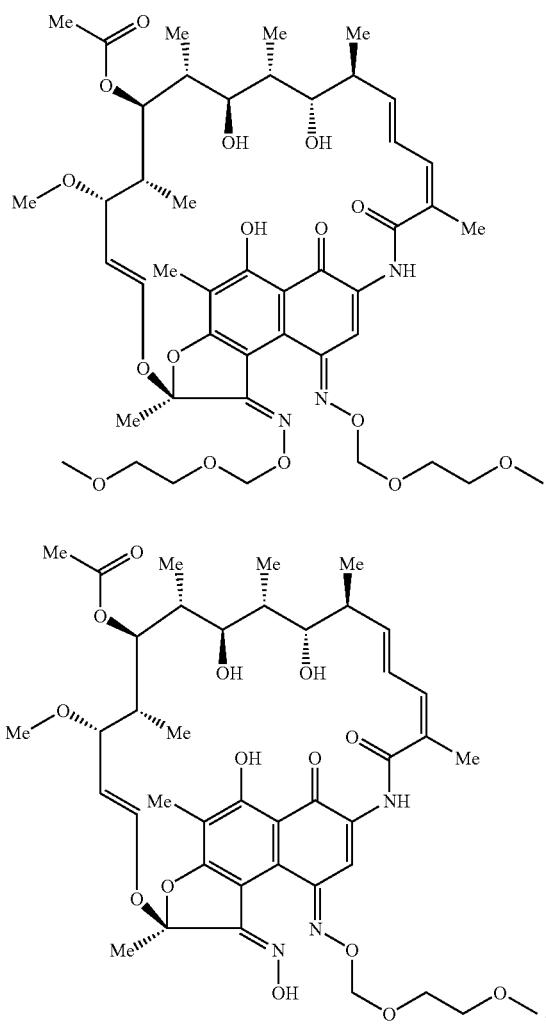
9. A compound of the formula 11-Deoxy-11-hydroxyiminorifamycin S
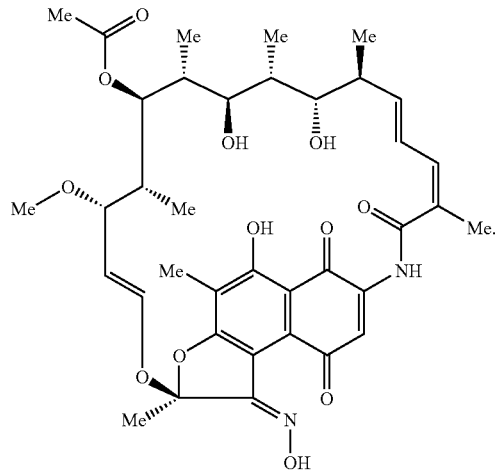
10. A compound of the formula 11-Deoxy-11-(4-pyridylcarboxy)iminorifamycin S
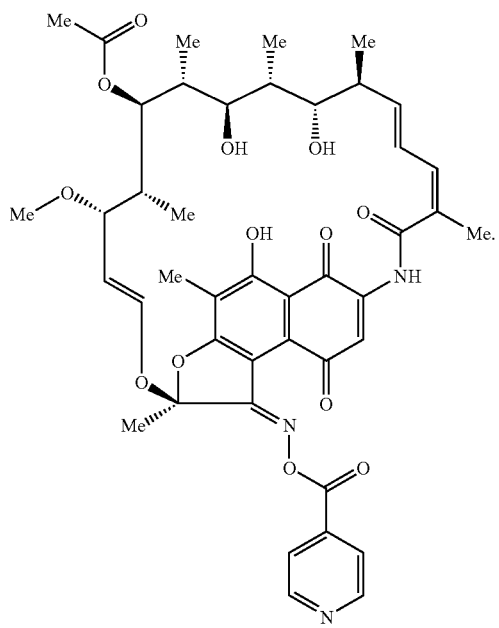
11. A compound of the formula 11-Deoxy-11-acetoxyiminorifamycin S
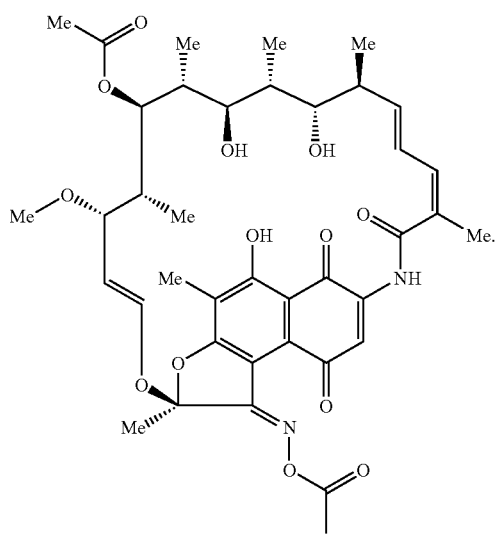

12. A compound of the formula 11-Deoxy-11-methoxy-ethoxymethoxyiminorifamycin S
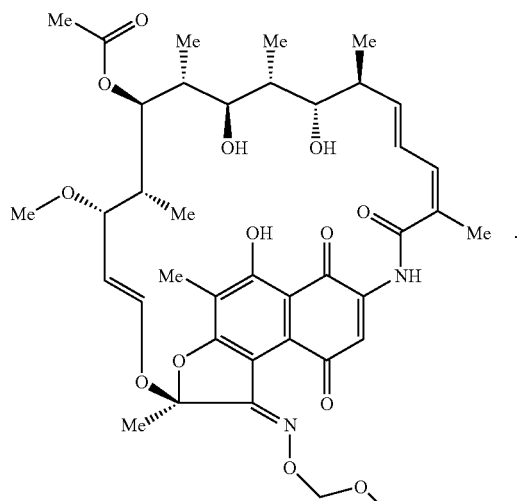
13. A compound of the formula 11-Deoxy-11-allyloxy-iminorifamycin S
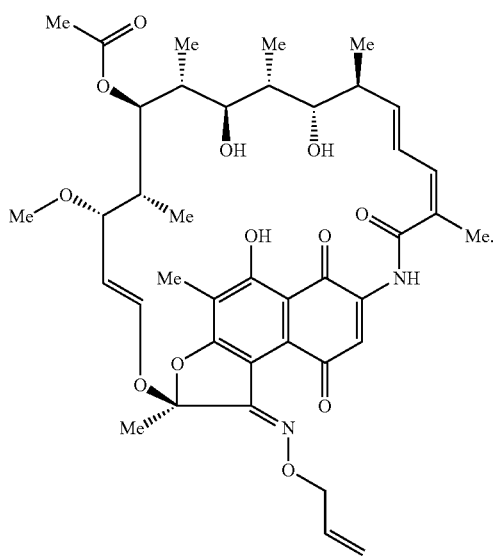
14. A compound of the formula 11-Deoxy-11-(2-bromo-ethoxyimino)rifamycin S
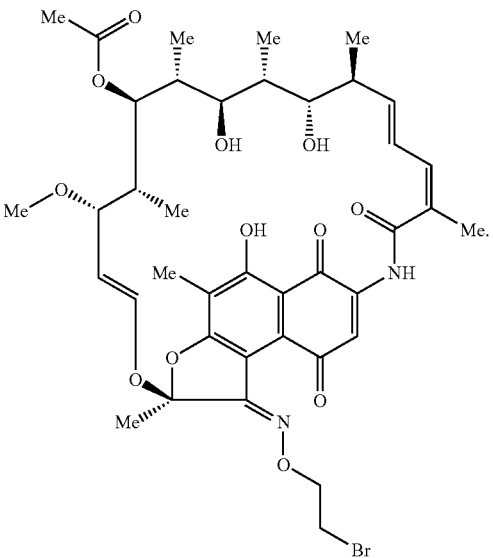
15. A compound of the formula (R/,S)-11-Deoxy-11-[{-{2-[4-(3-carboxy-1-cyclopropyl-6-fluoro-8-methoxy-4-oxo-1,4-dihydroquinolin-7-yl)-2-methylpiperazin-1-yl] ethoxyimino]}rifamycin S
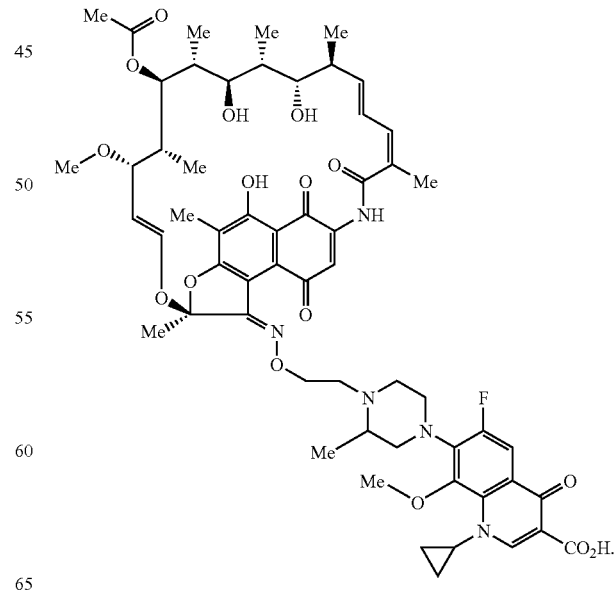

16. A compound of the formula 11-Deoxy-11-[{-{2-[4-(3-carboxy-1-cyclopropylcyclopropl-6-fluoro-4-oxo-1,4-dihydroquinolin-7-yl)piperazin-1-yl]ethoxyimino]}rifamycin S

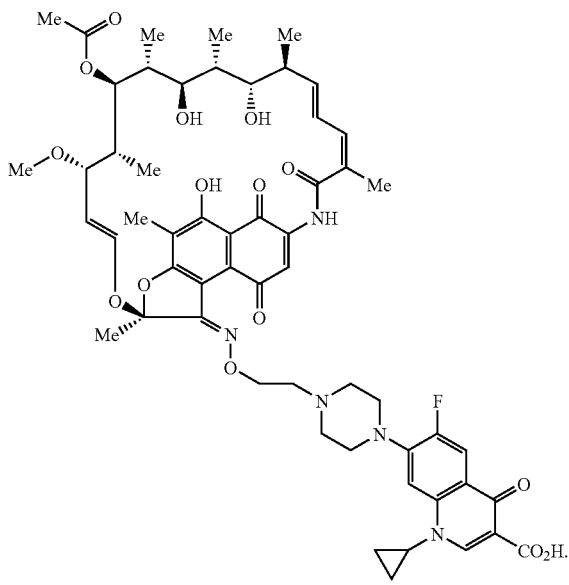

17. A compound of the formula 11-Deoxy-11-[{-{2-[6-(3-carboxy-1-cyclopropylcyclopropyl-6-fluoro-8-methoxy-4-oxo-1,4-dihydro-quinolin-7-yl) octahydro-pyrrolo[3,4-b]pyridin-1-yl]ethoxyimino]}rifamycin S

18. A compound of the formula 11-Deoxy-11-[{-{2-[4-{4-[5-(acetylamino-methyl)-2-oxo-oxazolidin-3-yl]-2-fluoro-phenyl}-piperazin-1-yl]ethoxyimino]}rifamycin S

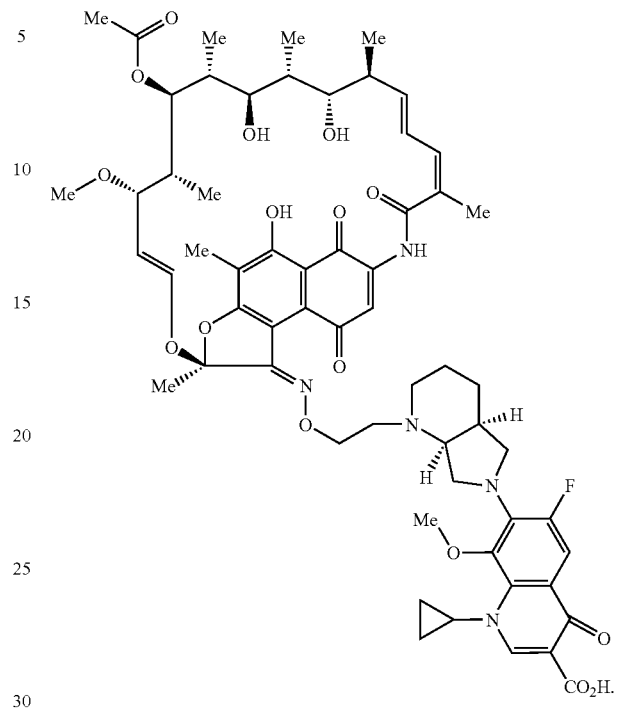

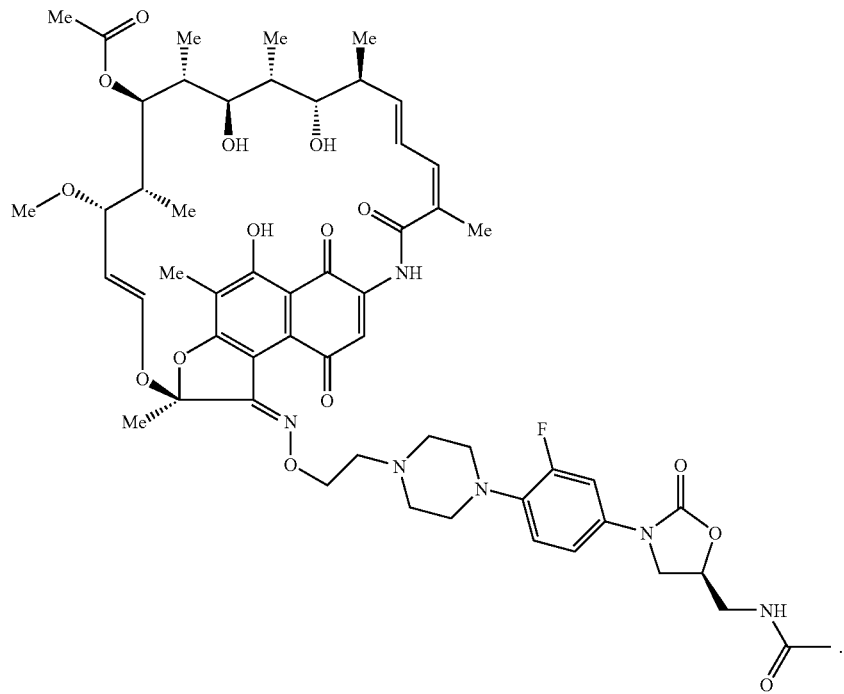

19. A compound of the formula 11-Deoxy-11-{2-[4-(pyridin-2-yl)piperazin-1-yl]ethoxyimino}rifamycin S
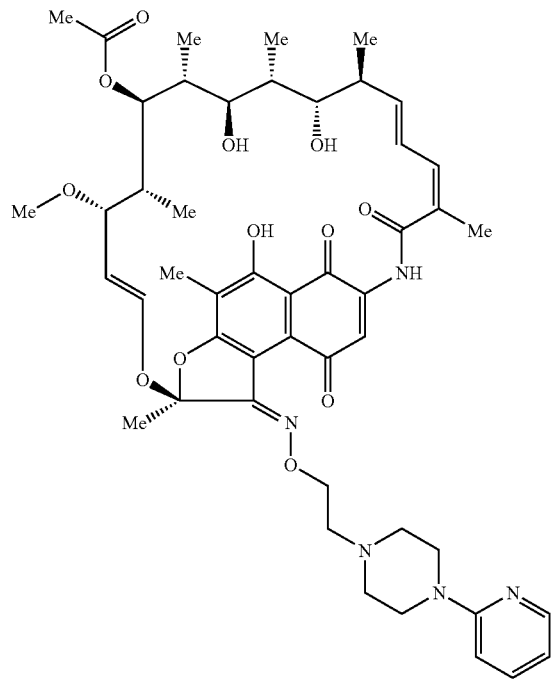
20. A compound of the formula 11-Deoxy-11-{2-[4-(3-trifluoromethyl-phenyl)-piperazin-1-yl]ethoxyimino}rifamycin S
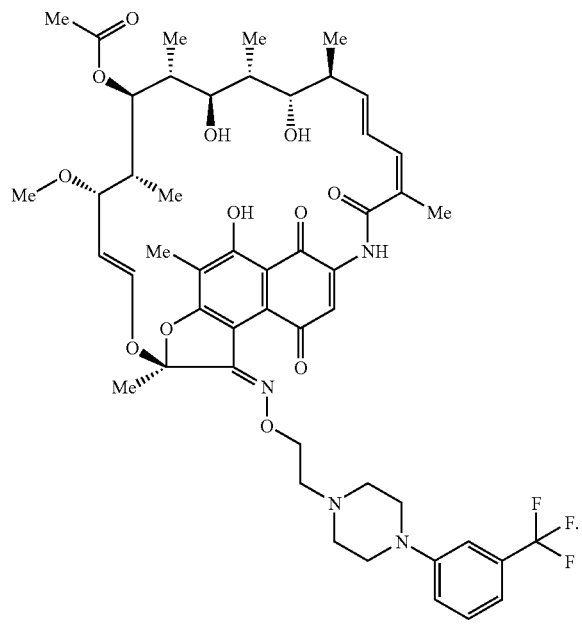
21. A compound of the formula 11-Deoxy-11-{2-[4-(isoquinoline-8-sulfonyl)-piperazin-1-yl]-ethoxyimino}rifamycin S
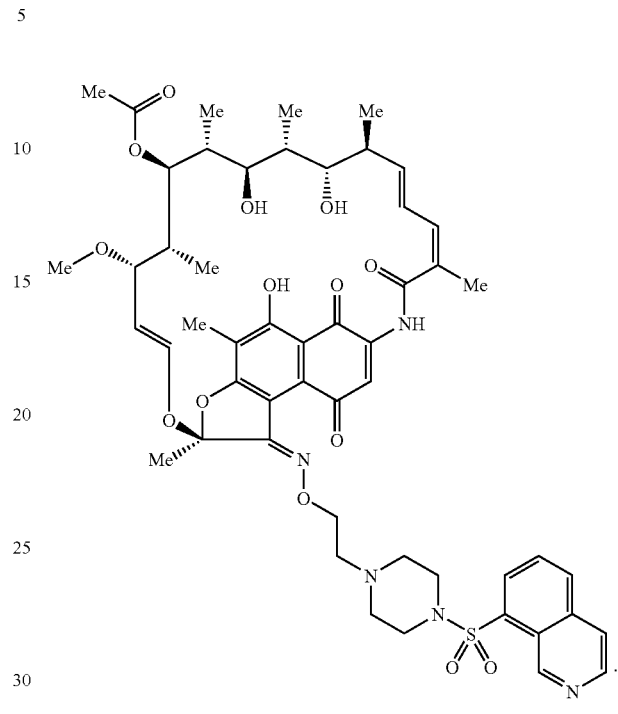
22. A compound of the formula 11-Deoxy-11-{2-[bis-(2-hydroxy-ethyl)-amino]ethoxyimino}rifamycin S
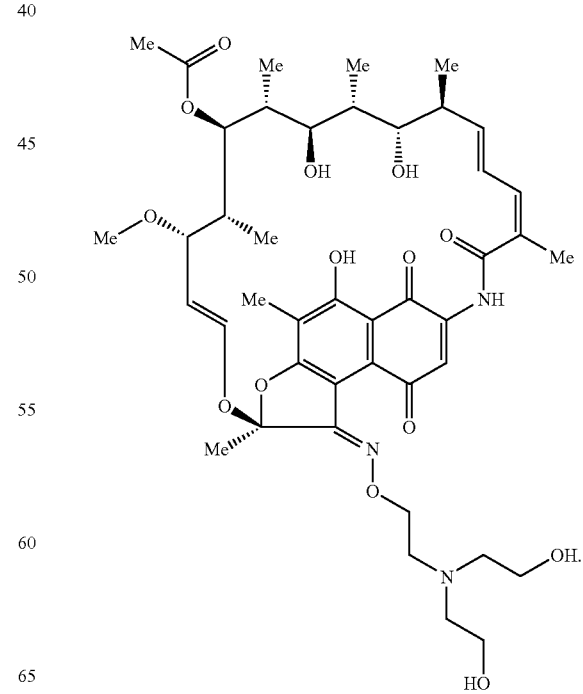

23. A compound of the formula 11-Deoxy-11-[2-(3,5-dimethyl-piperazin-1-yl)ethoxyimino]rifamycin S
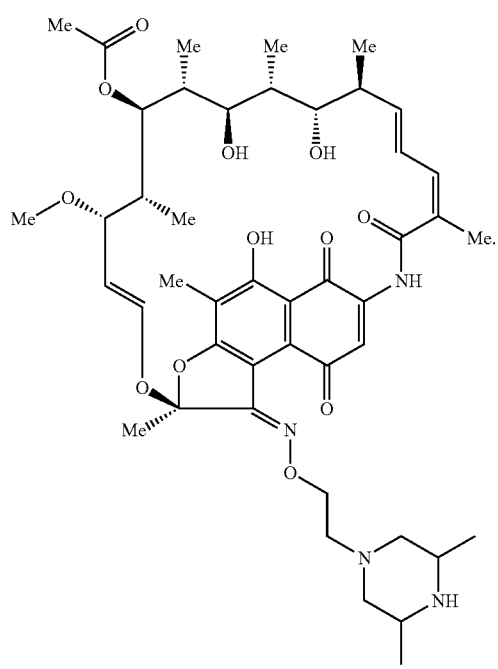
24. A compound of the formula 11-Deoxy-11-[2-(4-methylpiperazin-1-yl)ethoxyimino]rifamycin S
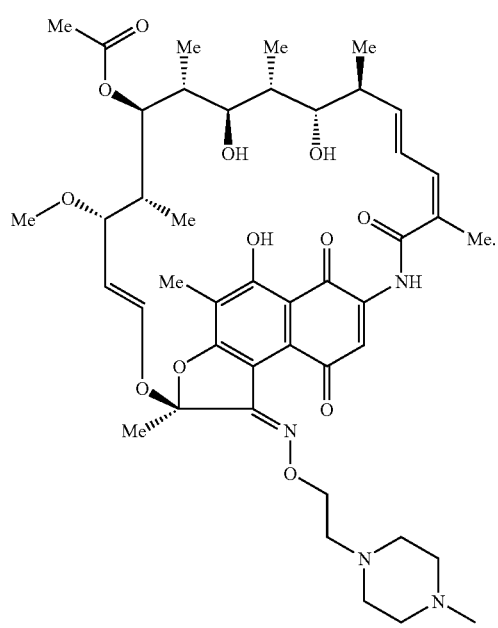
25. A compound of the formula 11-Deoxy-11-[2-(4-hydroxypiperadin-1-yl)ethoxyimino]rifamycin S
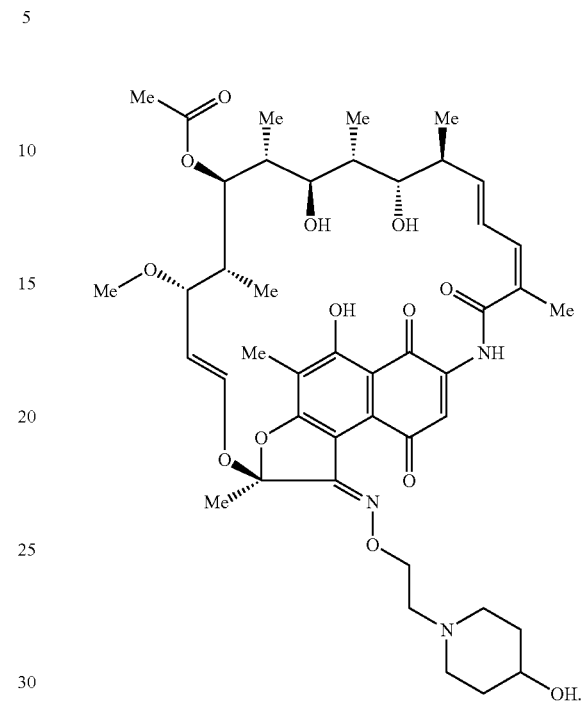
26. A compound of the formula 11-Deoxy-11-[2-morpholin-4-yl)ethoxyimino]rifamycin S
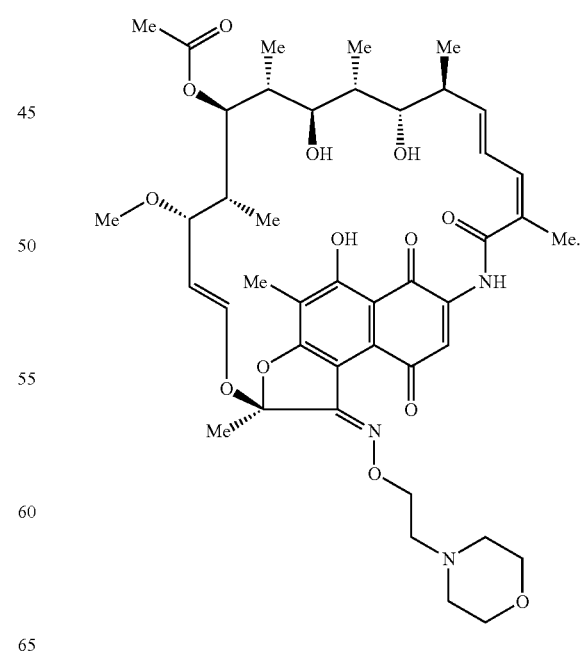

27. A compound of the formula 11-Deoxy-11-[2-(4-benzylpiperazin-1-yl)ethoxyimino]rifamycin S

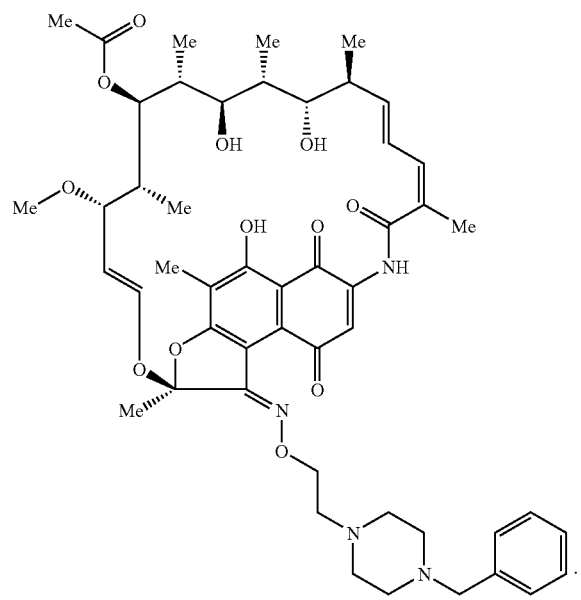

28. A compound of the formula 11-Deoxy-11-{2-[4-(2-hydroxy-phenyl)piperazin-1-yl]ethoxyimino}rifamycin S

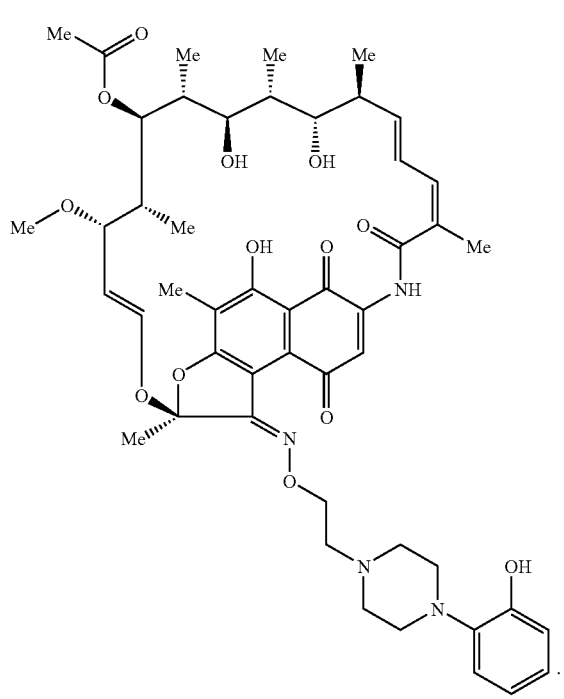

29. A compound of the formula 11-Deoxy-3-hydroxymethyl-11-(4-carboxymethoxyimino)-rifamycin S 30. A compound of the formula 11-Deoxy-3-(morpholin-4-yl)-11-(4-carboxymethoxyimino)-rifamycin S

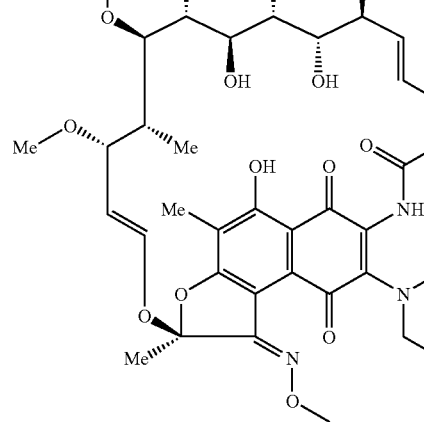

31. A compound of the formula 11-Deoxy-3-(morpholin-4-yl)-11-{2-oxo-2-[4-(3-carboxy-1-cyclopropl-6-fluoro-4- oxo-1,4-dihydroquinolin-7-yl)piperazin-1-yl]ethoxyimino}rifamycin S

33. A compound of the formula (R/S)-11-Deoxy-3-(morpholin-4-yl)-11-{2-oxo-2-[4-(3-carboxy-1-cyclopropyl-6-chloro-8-oxo-1,4-dihydroquinolin-7-yl)-3-aminopyrrolidin-1-yl]ethoxyimino}rifamycin S

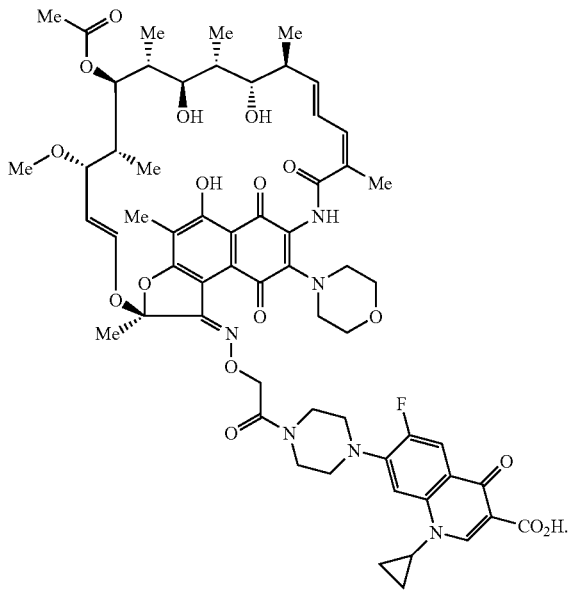

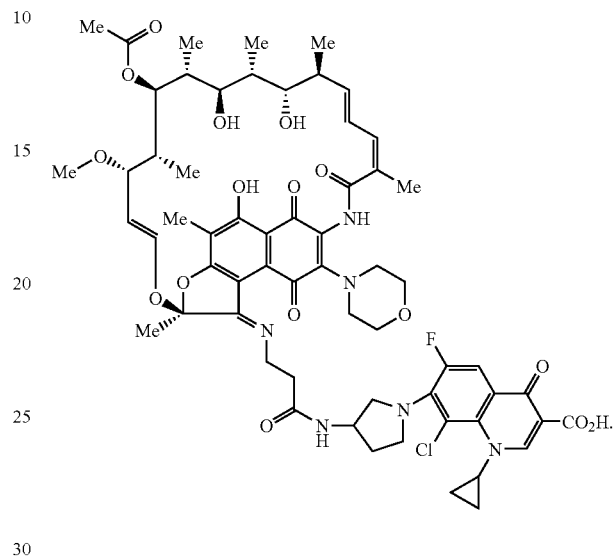

32. A compound of the formula 11-Deoxy-3-(morpholin-4-yl)-11-{2-oxo-2-[4-(3-carboxy-1-cyclopropyl-6-fluoro-8-methoxy-4-oxo-1,4-dihydroquinolin-7-yl)-2-methylpiperazin-1-yl]ethoxyimino}rifamycin S

34. A compound of the formula 11-Deoxy-11-{2-oxo-2-[4-(3-carboxy-1-cyclopropl-6-fluoro-4-oxo 1,4-dihydroquinolin-7-yl)piperazin-1-yl]ethoxyimino}rifamycin S

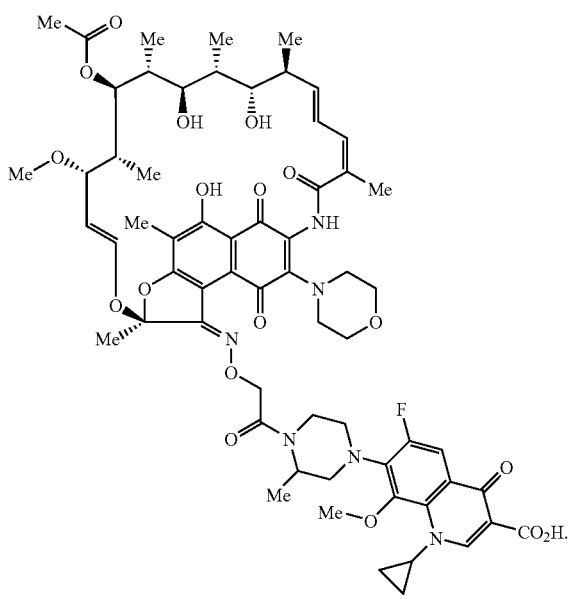

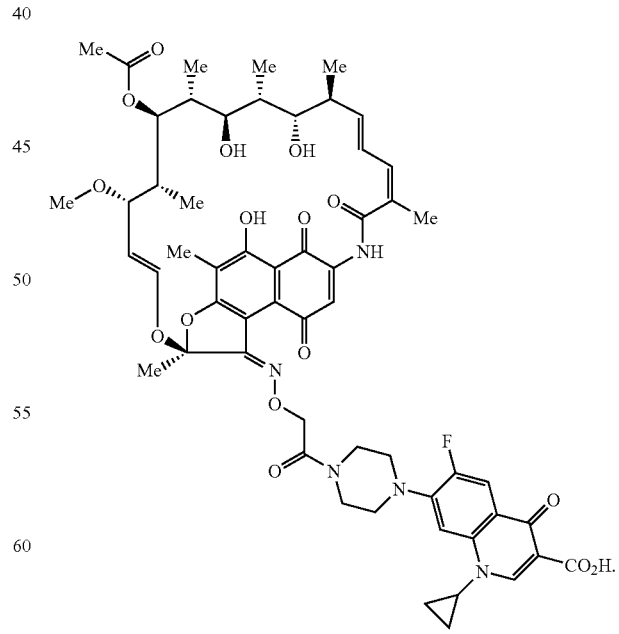

35. A compound of the formula 11-Deoxy-3-[4-(3-carboxy-1-cyclopropyl-6-fluoro-4-oxo-1,4-dihydroquinolin-7-yl)piperazin-1-yl]-11-hydroxyiminorifamycin S

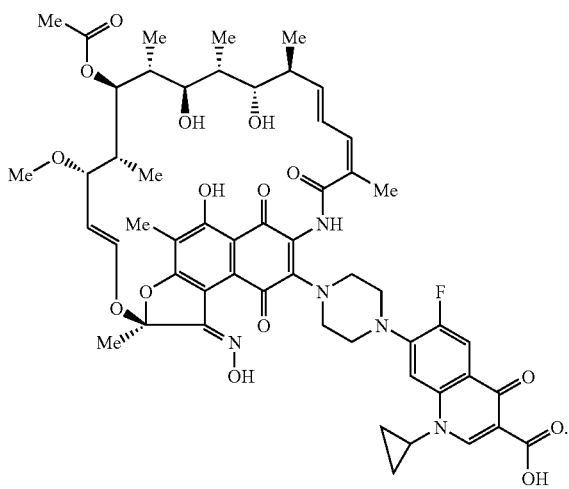

36. A compound of the formula 11-Deoxy-3-(morpholin-4-yl)-11-allyloxyiminorifamycin S

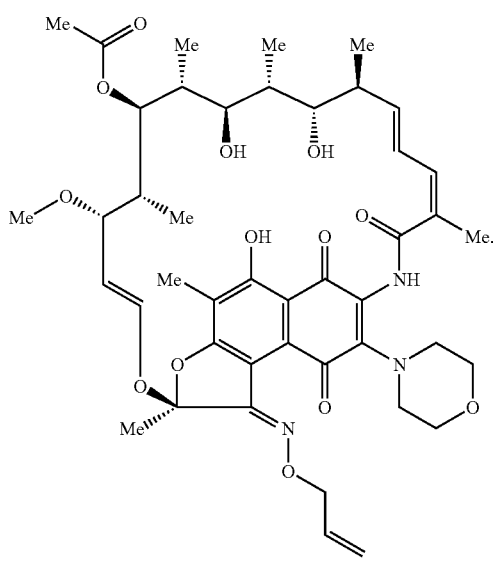

37. A compound of the formula 11-Deoxy-11-hydroxyimino-3-(4-methylpiperazin-1-yl)aminomethenylrifamycin SV:

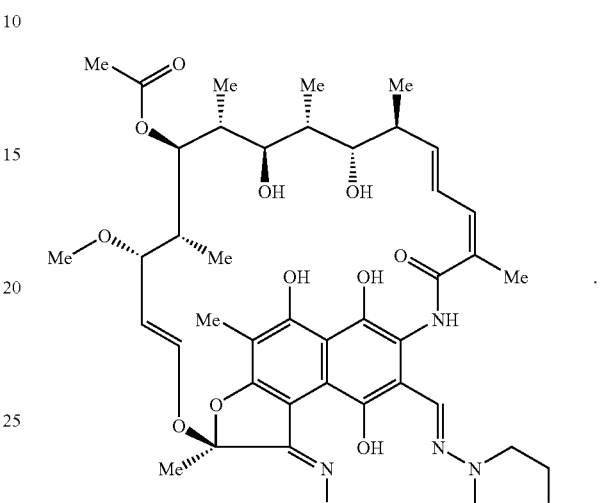

38. A compound of the formula 11-Deoxy-11-hydroxyimino-3-(4-methylpiperazin-1-yl)aminomethenylrifamycin S

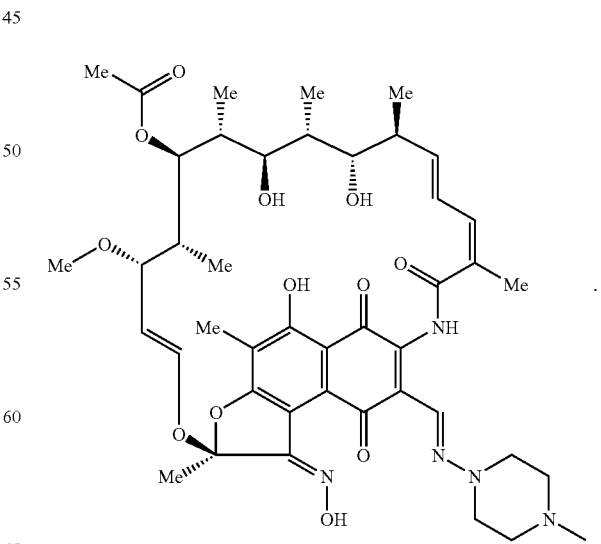

39. A compound of the formula 11-Deoxy-3-(morpholin-4-yl)-11-hydroxyiminorifamycin S
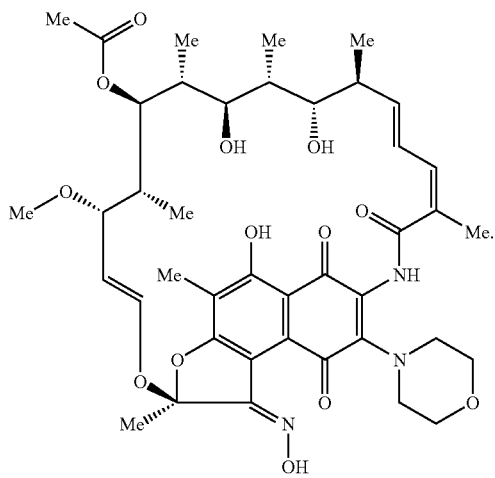
40. A compound of the formula 11-Deoxy-3-(morpholin-4-yl)-11-methoxyiminorifamycin S
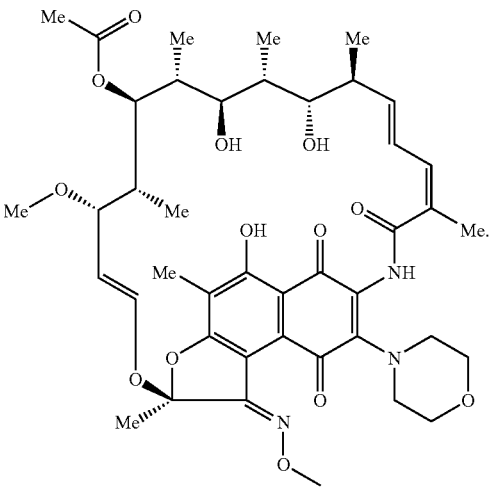
41. A compound of the formula 3-[4-(3-Carboxy-1-cyclopropl-6-fluoro-4-oxo-1,4-dihydroquinolin-7-yl)piperazin-1-yl-aminomethylenyl]-11-deoxy-11-hydroxyiminorifamycin SV:
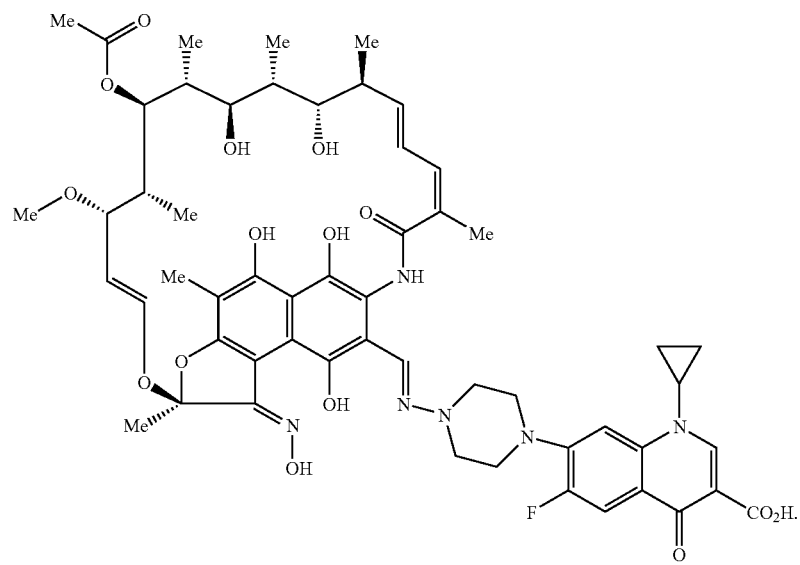

42. A compound of the formula (R/S)-3-[4-(3-Carboxy-1-cyclopropyl-6-fluoro-8-methoxy-4-oxo-1,4-dihydro-quinolin-7-yl)-2-methyl-piperazin-1-yl-aminomethylenyl]-11-deoxy-11-hydroxyiminorifamycin SV:

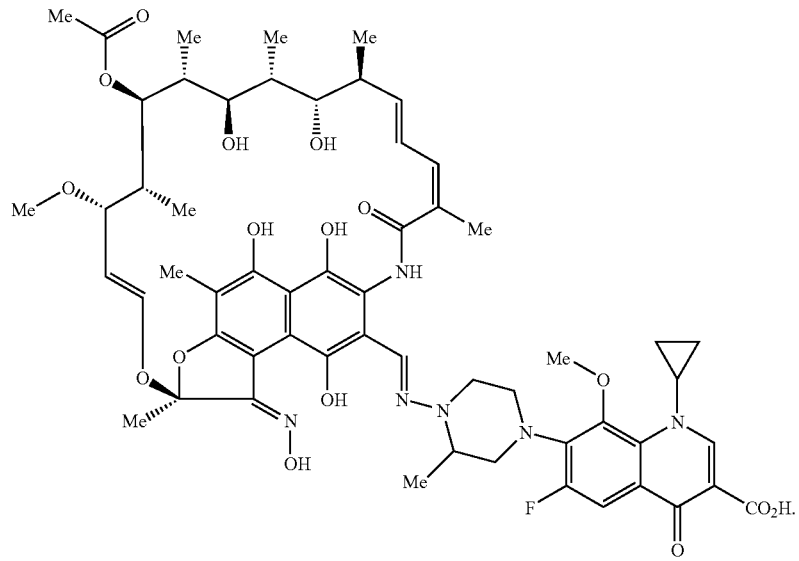

43. The compound of claim 1, wherein the compound is Formula II, and Y is —OH, —NHR$_4$, or —OR$_5$.

44. A pharmaceutical composition, useful as a medicament for the treatment or prevention of bacterial infections, comprising a therapeutically effective amount of a compound of claim 1 in combination with a pharmaceutically acceptable carrier.

45. A pharmaceutical composition, useful as a medicament for the treatment or prevention of bacterial infections, comprising a therapeutically effective amount of a compound of claim 3 in combination with a pharmaceutically acceptable carrier.

* * * * *